(12) United States Patent
Mason et al.

(10) Patent No.: US 12,037,621 B2
(45) Date of Patent: Jul. 16, 2024

(54) THREONINE PRODUCTION STRAIN HAVING ATTENUATED EXPRESSION OF THE YAFV GENE

(71) Applicant: Archer Daniels Midland Company, Decatur, IL (US)

(72) Inventors: Benjamin Mason, Decatur, IL (US); Jason Helvey, Decatur, IL (US)

(73) Assignee: ARCHER-DANIELS-MIDLAND COMPANY, Decatur, IL (US)

(*) Notice: Subject to any disclaimer, the term of this patent is extended or adjusted under 35 U.S.C. 154(b) by 45 days.

(21) Appl. No.: 17/476,162

(22) Filed: Sep. 15, 2021

(65) Prior Publication Data

US 2023/0085302 A1     Mar. 16, 2023

(51) Int. Cl.
| | | |
|---|---|---|
| C12P 13/08 | (2006.01) | |
| C07K 14/245 | (2006.01) | |
| C12N 1/20 | (2006.01) | |
| C12N 9/00 | (2006.01) | |
| C12N 9/80 | (2006.01) | |
| C12N 9/88 | (2006.01) | |
| C12R 1/19 | (2006.01) | |

(52) U.S. Cl.
CPC ............ *C12P 13/08* (2013.01); *C07K 14/245* (2013.01); *C12N 1/205* (2021.05); *C12N 9/80* (2013.01); *C12N 9/88* (2013.01); *C12N 9/93* (2013.01); *C12R 2001/19* (2021.05); *C12Y 305/01003* (2013.01); *C12Y 403/01019* (2013.01); *C12Y 604/01001* (2013.01)

(58) Field of Classification Search
CPC ....... C12P 13/08; C07K 14/245; C12N 1/205; C12N 9/80; C12N 9/88; C12N 9/93; C12Y 305/01003; C12Y 403/01019; C12Y 604/01001
See application file for complete search history.

(56) References Cited

U.S. PATENT DOCUMENTS

| | | |
|---|---|---|
| 7,723,097 B2 | 5/2010 | D'Elia et al. |
| 8,101,386 B2 | 1/2012 | Liaw et al. |
| 2005/0255568 A1 | 11/2005 | Bailey et al. |
| 2006/0210537 A1 | 9/2006 | Audonnet et al. |
| 2008/0009041 A1 | 1/2008 | Mizoguchi et al. |
| 2020/0080118 A1 | 3/2020 | Rieping |
| 2020/0115705 A1 | 4/2020 | Mason et al. |
| 2020/0370058 A1 | 11/2020 | Davis et al. |

FOREIGN PATENT DOCUMENTS

| | | |
|---|---|---|
| WO | 2021060438 | 4/2021 |

OTHER PUBLICATIONS

International Search Report for PCT/US2022/076502; Sep. 15, 2022 for Archer Daniels Midland Company; entire document.
Written Opinion of the International Searching Authority for PCT/US2022/076502 filed Sep. 15, 2022 for Archer Daniels Midland Company; entire document.

*Primary Examiner* — Iqbal H Chowdhury
(74) *Attorney, Agent, or Firm* — Andrew F. Nilles

(57) ABSTRACT

Improved production of threonine from *E. coli* by fermentation is accomplished by attenuation but not elimination of the expression of either or both of the yajV gene encoding omega-amidase (a.k.a. 2-oxoglutaramate amidase) and the ilvA gene encoding threonine dehydratase (a.k.a threonine deaminase). In cases where there is attenuated expression of the ilvA gene, there is no need to express an exogenous cimA gene. In examples of both cases, attenuation is accomplished by engineering these genes to contain a weaker ribosome site. Further improvements in threonine production are made by expression of a heterologous pyruvate carboxylase gene exemplified by expression of the *Corynebacterium glutamicum* pyc gene under control of an *E. coli* promoter, to provide expression of pyruvate carboxylase that is not naturally expressed in *E. coli*.

25 Claims, 5 Drawing Sheets

Specification includes a Sequence Listing.

A. Yields (g/g at 36hr)

B. Productivity (g/L/hr)

C. Titers at 36 hr

| SEQ ID NO: | Genetic Edit | Primer name | Primer sequence primer with gene edit underlined |
|---|---|---|---|
| 39 | PxapR-rhtC | rev_right_arm_pcr | CCAACCTTACCAGAGGGCGCCCCAG TTCCAGCGCGATGACCT |
| 40 | PxapR-rhtC | fwd_right_arm_pcr | TCGTATTAAATTATCATGCATAAAGTATTCCACCACCAGATATCCG ACATACATTTGACTCGCGGGG |
| 41 | PxapR-rhtC | fwd_left_arm_pcr | ACTTCCCGTCAGAGCCAACCGTTT CGCCGCTGGTGCAAT |
| 42 | PxapR-rhtC | rev_left_arm_pcr | TTTATGCCATGATAATTTAATACGATGTATTATTATATGGAGCACTTAAT ATGTTGATGTTATTTCTCACCGTC |
| 43 | T1-pR_RBS-ilvA | rev_right_arm_pcr | GCAGGGCTTCCCAACCTTACCAGAGGGCGCCCCAG GCCTTTTTCTTCCGGAATGGTC |
| 44 | T1-pR_RBS-ilvA | fwd_right_arm_pcr | GGGCGGGGCCCCTTGCTTTCAATGGTTGCATGTACTAAGGAGGTTGT ATGGCTGACTCGCAACCC |
| 45 | T1-pR_RBS-ilvA | rev_left_arm_pcr | TACATGCAACCATTGAAAAGCAAGAGAGGCCGCCCCGGAAGGTTGGG TATTAACCCCCCAGTTTGATTTATCG |
| 46 | T1-pR_RBS-ilvA | fwd_left_arm_pcr | AGGTAAGTCAACTTCCTCCGTCAGAGCCAACCGTTT CATGACGCTGGATATCGCGA |
| 47 | T1acsRBS-yafV | fwd_left_arm_pcr | ACTCCTCCGTCAGAGCCAACCGTTTG AAACCACTGGCACGTGGAGAATAAG |
| 48 | T1acsRBS-yafV | rev_right_arm_pcr | CCAACCTTACCAGAGGGCGCCCCAG CTGCAAAACTTCCCGAACCGCG |
| 49 | T1acsRBS-yafV | rev_left_arm_pcr | GGCCCCTTGCTTTCAATTAACATCTACAAGGAGAACAAAAG CGTGCCTGGTTTGAAGATTACGCTTTGC |
| 50 | T1acsRBS-yafV | fwd_right_arm_pcr | GGATGTTAATTGAAAAGCAAGAGGGCCCGCCCCGAAGGTTCGG GCTGATATTGGAAATATCTGATTTGCAAATTATCGTGTTATC |
| 51 | rbs5-rhtC | fwd_right_arm_pcr | TTAACCTCCTTAGTTTATTCAATT ACATTTGACTCGCGGGGAAACG |
| 52 | rbs5-rhtC | fwd_left_arm_pcr | ACTTCCCGTCAGAGCCAACCGTTT CGCCGCTGGTGCAATTGACC |
| 53 | rbs5-rhtC | rev_right_arm_pcr | CCAACCTTACCAGAGGGCGCCCCAG ATTCCAGCGCGATGACCTGCA |
| 54 | rbs5-rhtC | rev_left_arm_pcr | CGTTTCCCCGCGAGTCAAATGTAATTGAATAAACTAAGGAGGTTAAAGT ATGTTGATGTTATTTCTCACCGTCGCCA |
| 55 | PfocA-Cgl_pyc | fwd_left_arm_pcr | AGTCAACTTCCTCCGTCAGAGCCAACCGTTT GTTTATGCTGGATGGCCCGC |
| 56 | PfocA-Cgl_pyc | rev_left_arm_pcr | ACGAGATACTAACACAAAGCATTATAGATGAGAAATTGATATAGATCATATC GAGATCTGCCTTTGCCGGATG |
| 57 | PfocA-Cgl_pyc | fwd_insert_pcr | CTATAATGCTTTGTTAGTATCGTCGTCGCCGACTTAATAAAGAGAGAGTTAGT ATGTCGACTCACACATCTTC |
| 58 | PfocA-Cgl_pyc | rev_insert_pcr | AAGCCCGACACTGTCAGGTGCGGGCTTTTCTGTGTTTCC TTAGGAAACGACGACGATCAAG |
| 59 | PfocA-Cgl_pyc | fwd_nginc_arm_pc | AGCCCGCACCTGACAGTGTGGGGCTTTTTTTTTCGACCAAAGG AGCGATAGCGCCGGCTTAGTC |
| 60 | PfocA-Cgl_pyc | rev_right_arm_pcr | CCTTACCAGAGGGCGCCCCAGGTTT CGTCAATCCGGAAGTGGCCCTG |

Figure 4

SEQUENCE LISTING

<160> NUMBER OF SEQ ID NOS: 60

<210> SEQ ID NO 1
<211> LENGTH: 3423
<212> TYPE: DNA
<213> ORGANISM: Artificial Sequence
<220> FEATURE:
<223> OTHER INFORMATION: Pyc  C. glutamicum_cg0791

<400> SEQUENCE: 1

```
atgtcgactc acacatcttc aacgcttcca gcattcaaaa agatcttggt agcaaaccgc      60
ggcgaaatcg cggtccgtgc tttccgtgca gcactcgaaa ccggtgcagc cacggtagct     120
atttaccccc gtgaagatcg gggatcattc caccgctctt ttgcttctga agctgtccgc     180
attggtactg aaggctcacc agtcaaggcg tacctggaca tcgatgaaat tatcggtgca     240
gctaaaaaag ttaaagcaga tgctatttac ccgggatatg gcttcctgtc tgaaaatgcc     300
cagcttgccc gcgagtgcgc ggaaaacggc attactttta ttggcccaac cccagaggtt     360
cttgatctca ccggtgataa gtctcgtgcg gtaaccgccg cgaagaaggc tggtctgcca     420 gttttggcg aatccacccc gagcaaaaac atcgatgaca tcgttaaaag cgctgaaggc     480
cagacttacc ccatctttgt aaaggcagtt gccggtggtg gcggacgcgg tatgcgcttt     540
gtttcttcac ctgatgagct ccgcaaattg gcaacagaag catctcgtga agctgaagcg     600
gcattcggcg acggttcggt atatgtcgaa cgtgctgtga ttaaccccca gcacattgaa     660
gtgcagatcc ttgcgatcg cactggagaa gttgtacacc tttatgaacg tgactgctca     720
ctgcagcgtc gtcaccaaaa agttgtcgaa attgcgccag cacagcattt ggatccagaa     780
ctgcgtgatc gcatttgtgc ggatgcagta aagttctgcc gctccattgg ttaccaggqc     840 gcgggaaccg tggaattctt ggtcgatgaa aagggcaacc acgttttcat cgaaatgaac     900
ccacgtatcc aggttgagca caccgtgact gaagaagtca ccgaggtgga cctggtgaag     960
gcgcagatgc gcttggctgc tggtgcaacc ttgaaggaat tgggtctgac caagataag    1020 atcaagaccc acggtgcagc actgcagtgc cgcatcacca cggaagatcc aaacaacggc    1080
ttccgcccag ataccggaac tatcaccgcg taccgctcac caggcggagc tggcgttcgt    1140
cttgacggtg cagctcagct cggtggcgaa atcaccgcac actttgactc catgctggtg    1200
aaaatgacct gccgtggttc cgactttgaa actgctgttg ctcgtgcaca gcgcgcgttg    1260
```

-continued

```
gctgagttca ccgtgtctgg tgttgcaacc aacattggtt tcttgcgtgc gttgctgcgg    1320
gaagaggact tcacttccaa gcgcatcgcc accggattta tcggcgatca cccacacctc    1380
cttcaggctc cacctgcgga tgatgagcag ggacgcatcc tggattactt ggcagatgtc    1440
accgtgaaca agcctcatgg tgtgcgtcca aaggatgttg cagcaccaat cgataagctg    1500
cccaacatca aggatctgcc actgccacgc ggttcccgtg accgcctgaa gcagcttggc    1560
ccagccgcgt ttgctcgtga tctccgtgag caggacgcac tggcagttac tgataccacc    1620
ttccgcgatg cacaccagtc tttgcttgcg acccgagtcc gctcattcgc actgaagcct    1680
gcggcagagg ccgtcgcaaa gctgactcct gagcttttgt ccgtggaggc ctggggcggc    1740
gcgacctacg atgtggcgat gcgtttcctc tttgaggatc cgtgggacag gctcgacgag    1800
ctgcgcgagg cgatgccgaa tgtaaacatt cagatgctgc ttcgcggccg caacaccgtg    1860
ggatacaccc cgtacccaga ctccgtctgc cgcgcgtttg ttaaggaagc tgccacctcc    1920
ggcgtggaca tcttccgcat cttcgacgcg cttaacgacg tctcccagat gcgtccagca    1980
atcgacgcag tcctggagac caacaccgcg gtagccgagg tggctatggc ttattctggt    2040
gatctctctg atccaaatga aaagctctac accctggatt actacctaaa gatggcagag    2100
gagatcgtca agtctggcgc tcacattctg gccattaagg atatggctgg tctgcttcgc    2160
ccagctgcgg taaccaagct ggtcaccgca ctgcgccgtg aattcgatct gccagtgcac    2220
gtgcacaccc acgacactgc gggtggccag ttggctacct actttgctgc agctcaagct    2280
ggtgcagatg ctgttgacgg tgcttccgca ccactgtctg gcaccacctc ccagccatcc    2340
ctgtctgcca ttgttgctgc attcgcgcac acccgtcgcg ataccggttt gagcctcgag    2400
gctgtttctg acctcgagcc gtactgggaa gctgtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgctg atcgcttcga gctcatcgaa    2580
gacaactacg cagccgttaa tgagatgctg ggacgcccaa ccaaggtcac cccatcctcc    2640
aaggttgttg cgacctcgc actccacctg gttggtgcgg gtgtagatcc agcagacttt    2700
gctgcagacc cacaaaagta cgacatccca gactctgtca tcgcgttcct gcgcggcgag    2760
cttggtaacc ctccaggtgg ctggccagaa ccactgcgca cccgcgcact ggaaggccgc    2820
tccgaaggca aggcacctct gacggaagtt cctgaggaag agcaggcgca cctcgacgct    2880
gatgattcca aggaacgtcg caacagcctc aaccgcctgc tgttcccgaa gccaaccgaa    2940
gagttcctcg agcaccgtcg ccgcttcggc aaccctctg cgctggatga tcgtgaattc    3000
ttctacggac tggtcgaggg ccgcgagact ttgatccgcc tgccagatgt gcgcacccca    3060
ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ctgtgactgt tgctgaaggt gatgaggtca aggctggaga tgcagtcgca    3300
atcatcgagg ctatgaagat ggaagcaaca atcactgctt ctgttgacgg caagattgaa    3360
cgcgttgtgg ttcctgctgc aacgaaggtg gaaggtggcg acttgatcgt cgtcgtttcc    3420
taa                                                                  3423
```

<210> SEQ ID NO 2
<211> LENGTH: 1140
<212> TYPE: PRT

<213> ORGANISM: Artificial Sequence
<220> FEATURE:
<223> OTHER INFORMATION: Pyc C. glutamicum _ cg0791

<400> SEQUENCE: 2

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
```

-continued

```
            385                 390                 395                 400
        Lys Met Thr Cys Arg Gly Ser Asp Phe Glu Thr Ala Val Ala Arg Ala
                            405                 410                 415
        Gln Arg Ala Leu Ala Glu Phe Thr Val Ser Gly Val Ala Thr Asn Ile
                            420                 425                 430
        Gly Phe Leu Arg Ala Leu Leu Arg Glu Glu Asp Phe Thr Ser Lys Arg
                    435                 440                 445
        Ile Ala Thr Gly Phe Ile Ala Asp His Pro His Leu Leu Gln Ala Pro
                    450                 455                 460
        Pro Ala Asp Asp Glu Gln Gly Arg Ile Leu Asp Tyr Leu Ala Asp Val
        465                 470                 475                 480
        Thr Val Asn Lys Pro His Gly Val Arg Pro Lys Asp Val Ala Ala Pro
                            485                 490                 495
        Ile Asp Lys Leu Pro Asn Ile Lys Asp Leu Pro Leu Pro Arg Gly Ser
                        500                 505                 510
        Arg Asp Arg Leu Lys Gln Leu Gly Pro Ala Ala Phe Ala Arg Asp Leu
                        515                 520                 525
        Arg Glu Gln Asp Ala Leu Ala Val Thr Asp Thr Thr Phe Arg Asp Ala
        530                 535                 540
        His Gln Ser Leu Leu Ala Thr Arg Val Arg Ser Phe Ala Leu Lys Pro
        545                 550                 555                 560
        Ala Ala Glu Ala Val Ala Lys Leu Thr Pro Glu Leu Leu Ser Val Glu
                        565                 570                 575
        Ala Trp Gly Gly Ala Thr Tyr Asp Val Ala Met Arg Phe Leu Phe Glu
                        580                 585                 590
        Asp Pro Trp Asp Arg Leu Asp Glu Leu Arg Glu Ala Met Pro Asn Val
                    595                 600                 605
        Asn Ile Gln Met Leu Leu Arg Gly Arg Asn Thr Val Gly Tyr Thr Pro
                    610                 615                 620
        Tyr Pro Asp Ser Val Cys Arg Ala Phe Val Lys Glu Ala Ala Ser Ser
        625                 630                 635                 640
        Gly Val Asp Ile Phe Arg Ile Phe Asp Ala Leu Asn Asp Val Ser Gln
                        645                 650                 655
        Met Arg Pro Ala Ile Asp Ala Val Leu Glu Thr Asn Thr Ala Val Ala
                        660                 665                 670
        Glu Val Ala Met Ala Tyr Ser Gly Asp Leu Ser Asp Pro Asn Glu Lys
                    675                 680                 685
        Leu Tyr Thr Leu Asp Tyr Tyr Leu Lys Met Ala Glu Glu Ile Val Lys
                    690                 695                 700
        Ser Gly Ala His Ile Leu Ala Ile Lys Asp Met Ala Gly Leu Leu Arg
        705                 710                 715                 720
        Pro Ala Ala Val Thr Lys Leu Val Thr Ala Leu Arg Arg Glu Phe Asp
                        725                 730                 735
        Leu Pro Val His Val His Thr His Asp Thr Ala Gly Gly Gln Leu Ala
                        740                 745                 750
        Thr Tyr Phe Ala Ala Gln Ala Gly Ala Asp Ala Val Asp Gly Ala
                    755                 760                 765
        Ser Ala Pro Leu Ser Gly Thr Thr Ser Gln Pro Ser Leu Ser Ala Ile
                    770                 775                 780
        Val Ala Ala Phe Ala His Thr Arg Arg Asp Thr Gly Leu Ser Leu Glu
        785                 790                 795                 800
        Ala Val Ser Asp Leu Glu Pro Tyr Trp Glu Ala Val Arg Gly Leu Tyr
                        805                 810                 815
```

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
            850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
            930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe  Phe Tyr Gly Leu Val  Glu Gly Arg
                995                 1000                 1005

Glu Thr  Leu Ile Arg Leu Pro  Asp Val Arg Thr Pro  Leu Leu Val
        1010                 1015                 1020

Arg Leu Asp Ala Ile Ser Glu  Pro Asp Asp Lys Gly  Met Arg Asn
        1025                 1030                 1035

Val Val  Ala Asn Val Asn Gly  Gln Ile Arg Pro Met  Arg Val Arg
        1040                 1045                 1050

Asp Arg  Ser Val Glu Ser Val  Thr Ala Thr Ala Glu  Lys Ala Asp
        1055                 1060                 1065

Ser Ser  Asn Lys Gly His Val  Ala Ala Pro Phe Ala  Gly Val Val
        1070                 1075                 1080

Thr Val  Thr Val Ala Glu Gly  Asp Glu Val Lys Ala  Gly Asp Ala
        1085                 1090                 1095

Val Ala  Ile Ile Glu Ala Met  Lys Met Glu Ala Thr  Ile Thr Ala
        1100                 1105                 1110

Ser Val  Asp Gly Lys Ile Asp  Arg Val Val Pro Ala  Ala Thr
        1115                 1120                 1125

Lys Val  Glu Gly Gly Asp Leu  Ile Val Val Ser
        1130                 1135                 1140

<210> SEQ ID NO 3
<211> LENGTH: 1000
<212> TYPE: DNA
<213> ORGANISM: Artificial Sequence
<220> FEATURE:
<223> OTHER INFORMATION: AslB upstream homology arm

<400> SEQUENCE: 3
gtttatcgct ggatggcccg cctgagatcc acaatcaata tcgcgtgact aaaggtggca     60
gacccacgca taagctggtg atgcgtgccc tgacgctcct gcaaaaacat catgtcgact    120
ataacgtgct ggtctgcgtt aatcgcacca gcgcgcagca accgttgcag gtatatgatt    180

```
ttttgtgcga tgcgggagtc gaattcatcc agtttattcc ggtggtcgag cgcctggctg    240
atgaaacaac tgcccgcgat ggacttaagt tacatgcgcc tggtgatatt cagggtgagc    300
taacggaatg gtcggtgcgc cccgaggagt tcggtgagtt tctggtggcg atattcgacc    360
actggatcaa acgcgacgtc ggcaagattt tcgtgatgaa tatcgaatgg gcgtttgcca    420
attttgtcgg tgcgccgggt gcggtttgcc atcatcagcc aacctgtggg cgctcggtga    480
ttgttgagca caacgcgac gtttacgcct gtgatcacta tgtttatccg caatatcggc    540
tggggaatat gcaccagcaa acaattgcag aaatgatcga ttccccgcaa cagcaggcgt    600
ttggtgaaga taaatttaag cagttaccgg cgcagtgtcg cagttgtaac gtgttaaaag    660
cgtgctgggg aggctgcccg aaacaccgct tcatgctcga tgccagcggc aaaccgggac    720
tgaattattt gtgtgccggg tatcagcgtt atttccgcca tctaccgcca tatcttaaag    780
caatggctga tttgctggcg cacggtcgcc cggccagcga cattatgcat gcgcatttgc    840
tggtggtgag taagtagaaa tcggcggccg cctgcggttg attgccggat gcggcgtaaa    900
cgccttatcc ggcctacatg atcgtgcaaa ttcaataaat tgcagcgttc tgtaggctgg    960
ataagatgcg tcagcatcgc atccggcaaa ggcagatctc                         1000

<210> SEQ ID NO 4
<211> LENGTH: 1000
<212> TYPE: DNA
<213> ORGANISM: Artificial Sequence
<220> FEATURE:
<223> OTHER INFORMATION: AslA downstream homology arm

<400> SEQUENCE: 4
agcgatagcg ccggcttagt cagatttaat ctgcgcgcgt ggtggatatt ttttcaggat     60
ctccatatac gcgtgcattt cggtctgtag cggtacaccc atcggaatat ggcgcacgcc    120
gatggagtcg cttccctgcg gatcggtgta gaggttaaac accgacgatc cgccgtttg    180 cattactgtg ccggtgaatc caccctgata tccgctctgg gtataagcgt aaggttgctg    240
aatcaggacg tgatacttga actcatccat acgcacagca gcgagtttac cgttgaggaa    300
gtagtgctcg gccttacggt tagactgacc atttgttccc aggaagaagg atgtctggtc    360
cacaccatcg ataaaggtgg ttttcggcac taaattcgcc actttcgctc caggatgccc    420
tgccagatcc agcgcggtag ggaagagatc tgccagatcg acaataccgt cagatttacg    480
cggttggatc atccctttcc agtaaacgaa agtcggtacg cgaacgccgc cttcccaggt    540
cgaacctttc gcaccacgga acggggtgcg tccgtgcggc ggtacttcgg cttccggtcc    600
gttatcggag gtaaagacga tcagcgtgtt atcaagctga ccgtttttct ccagtgtttt    660
atacagatta gcgaacacat cgttcatctc caccatgcag tcgccatacg aggtgcgtgc    720
cggagagcta cccgcatatt tcgcatttgg gtagttatcg aagtggcagc cacgagtgcc    780
gtagtagagg aagaatggtt tatcgctctt cgccatcttg tcgaggaact taacgccata    840
gtccatccag cgttgatcca gatcttccat atatttcggc gtaatgtcgg caatggcctg    900
ttgttcgccg ccgcgcaccg catgaacgtc atctttgctg aacggtaatt gcttgatgta    960
ttcagaacgg tccggactca gggccacttc cggattgacg                         1000

<210> SEQ ID NO 5
<211> LENGTH: 5557
<212> TYPE: DNA
<213> ORGANISM: Artificial Sequence
<220> FEATURE:
```

<223> OTHER INFORMATION: AslB upstream homology arm-PfocA promoter-pyc-aslA downstream homology arm

<400> SEQUENCE: 5

```
gtttatcgct ggatggcccg cctgagatcc acaatcaata tcgcgtgact aaaggtggca    60
gacccacgca taagctggtg atgcgtgccc tgacgctcct gcaaaaacat catgtcgact   120
ataacgtgct ggtctgcgtt aatcgcacca gcgcgcagca accgttgcag gtatatgatt   180
ttttgtgcga tgcgggagtc gaattcatcc agtttattcc ggtggtcgag cgcctggctg   240
atgaaacaac tgcccgcgat ggacttaagt tacatgcgcc tggtgatatt cagggtgagc   300
taacggaatg gtcggtgcgc cccgaggagt tcggtgagtt tctggtggcg atattcgacc   360
actggatcaa acgcgacgtc ggcaagattt tcgtgatgaa tatcgaatgg gcgtttgcca   420
attttgtcgg tgcgccgggt gcggtttgcc atcatcagcc aacctgtggg cgctcggtga   480
ttgttgagca caacggcgac gtttacgcct gtgatcacta tgtttatccg caatatcggc   540
tggggaatat gcaccagcaa acaattgcag aaatgatcga ttccccgcaa cagcaggcgt   600
ttggtgaaga taaatttaag cagttaccgg cgcagtgtcg cagttgtaac gtgttaaaag   660
cgtgctgggg aggctgcccg aaacaccgct tcatgctcga tgccagcggc aaaccgggac   720
tgaattattt gtgtgccggg tatcagcgtt atttccgcca tctaccgcca tatcttaaag   780
caatggctga tttgctggcg cacggtcgcc cggccagcga cattatgcat gcgcatttgc   840
tggtggtgag taagtagaaa tcggcggccg cctgcggttg attgccggat gcggcgtaaa   900
cgccttatcc ggcctacatg atcgtgcaaa ttcaataaat tgcagcgttc tgtaggctgg   960
ataagatgcg tcagcatcgc atccggcaaa ggcagatctc gatatgatct atatcaattt  1020
ctcatctata atgctttgtt agtatctcgt cgccgactta ataaagagag agttagtatg  1080
tcgactcaca catcttcaac gcttccagca ttcaaaaaga tcttggtagc aaaccgcggc  1140
gaaatcgcgg tccgtgcttt ccgtgcagca ctcgaaaccg gtgcagccac ggtagctatt  1200
taccccgtg aagatcgggg atcattccac cgctcttttg cttctgaagc tgtccgcatt  1260
ggtactgaag gctcaccagt caaggcgtac ctggacatcg atgaaattat cggtgcagct  1320
aaaaaagtta agcagatgc tatttacccg ggatatggct tcctgtctga aaatgcccag  1380
cttgcccgcg agtgcgcgga aaacggcatt acttttattg gcccaacccc agaggttctt  1440
gatctcaccg gtgataagtc tcgtgcggta accgccgcga agaaggctgg tctgccagtt  1500
ttggcggaat ccaccccgag caaaaacatc gatgacatcg ttaaaagcgc tgaaggccag  1560
acttacccca tctttgtaaa ggcagttgcc ggtggtggcg gacgcggtat gcgctttgtt  1620
tcttcacctg atgagctccg caaattggca acagaagcat ctcgtgaagc tgaagcggca  1680
ttcggcgacg gttcggtata tgtcgaacgt gctgtgatta ccccccagca cattgaagtg  1740
cagatccttg gcgatcgcac tggagaagtt gtacaccttt atgaacgtga ctgctcactg  1800
cagcgtcgtc accaaaaagt tgtcgaaatt gcgccagcac agcatttgga tccagaactg  1860
cgtgatcgca tttgtgcgga tgcagtaaag ttctgccgct ccattggtta ccagggcgcg  1920
ggaaccgtgg aattcttggt cgatgaaaag ggcaaccacg ttttcatcga aatgaaccca  1980
cgtatccagg ttgagcacac cgtgactgaa gaagtcaccg aggtggacct ggtgaaggcg  2040
cagatgcgct ggctgctgg tgcaaccttg aaggaattgg gtctgaccca agataagatc  2100
aagacccacg gtgcagcact gcagtgccgc atcaccacgg aagatccaaa caacggcttc  2160
cgcccagata ccggaactat caccgcgtac cgctcaccag gcgagctgg cgttcgtctt  2220
```

```
gacggtgcag ctcagctcgg tggcgaaatc accgcacact ttgactccat gctggtgaaa    2280
atgacctgcc gtggttccga ctttgaaact gctgttgctc gtgcacagcg cgcgttggct    2340
gagttcaccg tgtctggtgt tgcaaccaac attggtttct tgcgtgcgtt gctgcgggaa    2400
gaggacttca cttccaagcg catcgccacc ggatttatcg gcgatcaccc cacctccttt    2460
caggctccac ctgcggatga tgagcaggga cgcatcctgg attacttggc agatgtcacc    2520
gtgaacaagc tcatggtgt gcgtccaaag gatgttgcag caccaatcga taagctgccc     2580
aacatcaagg atctgccact gccacgcggt tcccgtgacc gcctgaagca gcttggccca    2640
gccgcgtttg ctcgtgatct ccgtgagcag gacgcactgg cagttactga taccaccttc    2700
cgcgatgcac accagtcttt gcttgcgacc cgagtccgct cattcgcact gaagcctgcg    2760
gcagaggccg tcgcaaagct gactcctgag cttttgtccg tggaggcctg gggcggcgcg    2820
acctacgatg tggcgatgcg tttcctcttt gaggatccgt gggacaggct cgacgagctg    2880
cgcgaggcga tgccgaatgt aaacattcag atgctgcttc gcggccgcaa caccgtggga    2940
tacacccgt acccagactc cgtctgccgc gcgtttgtta aggaagctgc cacctccggc     3000
gtggacatct tccgcatctt cgacgcgctt aacgacgtct cccagatgcg tccagcaatc    3060
gacgcagtcc tggagaccaa caccgcggta gccgaggtgg ctatggctta ttctggtgat    3120
ctctctgatc caaatgaaaa gctctacacc ctggattact acctaaagat ggcagaggag    3180
atcgtcaagt ctggcgctca cattctggcc attaaggata tggctggtct gcttcgccca    3240
gctgcggtaa ccaagctggt caccgcactg cgccgtgaat tcgatctgcc agtgcacgtg    3300
cacacccacg acactgcggg tggccagttg gctacctact ttgctgcagc tcaagctggt    3360
gcagatgctg ttgacggtgc ttccgcacca ctgtctggca ccacctccca gccatccctg    3420
tctgccattg ttgctgcatt cgcgcacacc cgtcgcgata ccggtttgag cctcgaggct    3480
gtttctgacc tcgagccgta ctgggaagct gtgcgcggac tgtacctgcc atttgagtct    3540
ggaaccccag gccaaccgg tcgcgtctac cgccacgaaa tcccaggcgg acagttgtcc     3600
aacctgcgtg cacaggccac cgcactgggc cttgctgatc gcttcgagct catcgaagac    3660
aactacgcag ccgttaatga gatgctggga cgcccaacca aggtcacccc atcctccaag    3720
gttgttggcg acctcgcact ccacctggtt ggtgcgggtg tagatccagc agactttgct    3780
gcagacccac aaaagtacga catcccagac tctgtcatcg cgttcctgcg cggcgagctt    3840
ggtaaccctc caggtggctg ccagaaccca ctgcgcaccc gcgcactgga aggccgctcc    3900
gaaggcaagg cacctctgac ggaagttcct gaggaagagc aggcgcacct cgacgctgat    3960
gattccaagg aacgtcgcaa cagcctcaac cgcctgctgt cccgaagcc aaccgaagag     4020
ttcctcgagc accgtcgccg cttcggcaac acctctgcgc tggatgatcg tgaattcttc    4080
tacggactgg tcgagggccg cgagactttg atccgcctgc cagatgtgcg caccccactg    4140
cttgttcgcc tggatgcgat ctctgagcca gacgataagg gtatgcgcaa tgttgtggcc    4200
aacgtcaacg gccagatccg cccaatgcgt gtgcgtgacc gctccgttga gtctgtcacc    4260
gcaaccgcag aaaaggcaga ttcctccaac aagggccatg ttgctgcacc attcgctggt    4320
gttgtcactg tgactgttgc tgaaggtgat gaggtcaagg ctggagatgc agtcgcaatc    4380
atcgaggcta tgaagatgga agcaacaatc actgcttctg ttgacggcaa gattgaacgc    4440
gttgtggttc ctgctgcaac gaaggtggaa ggtggcgact tgatcgtcgt cgtttcctaa    4500
ggaaacacag aaaaaagccc gcacctgaca gtgcgggctt ttttttcga ccaaaggagc     4560
gatagcgccg gcttagtcag atttaatctg cgcgcgtggt ggatatttt tcaggatctc     4620
```

-continued

```
catatacgcg tgcatttcgg tctgtagcgg tacacccatc ggaatatgac gcacgccgat    4680
ggagtcgctt tcctgcggat cggtgtagag gttaaacacc gacgatcccg ccgtttgcat    4740
tactgtgccg gtgaatccac cctgatatcc gctctgggta taagcgtaag gttgctgaat    4800
caggacgtga tacttgaact catccatacg cacagcagcg agtttaccgt tgaggaagta    4860
gtgctcggcc ttacggttag actgaccatt tgttcccagg aagaaggatg tctggtccac    4920
accatcgata aggtggttt tcggcactaa attcgccact ttcgctccag gatgccctgc     4980
cagatccagc gcggtaggga agagatctgc cagatcgaca ataccgtcag atttacgcgg    5040
ttggatcatc cctttccagt aaacgaaagt cggtacgcga acgccgcctt cccaggtcga    5100
acctttcgca ccacggaacg gggtgcgtcc gtgcggcggt acttcggctt ccggtccgtt    5160
atcggaggta aagacgatca gcgtgttatc aagctgaccg ttttctcca gtgttttata     5220 cagattagcg aacacatcgt tcatctccac catgcagtcg ccatacgagg tgcgtgccgg    5280
agagctaccc gcatatttcg catttgggta gttatcgaag tggcagccac gagtgccgta    5340
gtagaggaag aatggtttat cgctcttcgc catcttgtcg aggaacttaa cgccatagtc    5400
catccagcgt tgatccagat cttccatata tttcggcgta atgtcggcaa tggcctgttg    5460
ttcgccgccg cgcaccgcat gaacgtcatc tttgctgaac ggtaattgct tgatgtattc    5520
agaacggtcc ggactcaggg ccacttccgg attgacg                             5557

<210> SEQ ID NO 6
<211> LENGTH: 77
<212> TYPE: DNA
<213> ORGANISM: Artificial Sequence
<220> FEATURE:
<223> OTHER INFORMATION: Pfoc_E. coli_promoter

<400> SEQUENCE: 6
gatatgatct atatcaattt ctcatctata atgctttgtt agtatctcgt cgccgactta      60
ataaagagag agttagt                                                     77

<210> SEQ ID NO 7
<211> LENGTH: 3500
<212> TYPE: DNA
<213> ORGANISM: Artificial Sequence
<220> FEATURE:
<223> OTHER INFORMATION: Pfoc-pyc promoter-gene

<400> SEQUENCE: 7
gatatgatct atatcaattt ctcatctata atgctttgtt agtatctcgt cgccgactta      60
ataaagagag agttagtatg tcgactcaca catcttcaac gcttccagca ttcaaaagaa     120
tcttggtagc aaaccgcggc gaaatcgcgg tccgtgcttt ccgtcagca ctcgaaaccg      180 gtgcagccac ggtagctatt tacccccgtg aagatcgggg atcattccac cgctcttttg    240
cttctgaagc tgtccgcatt ggtactgaag gctcaccagt caaggcgtac ctggacatcg    300
atgaaattat cggtgcagct aaaaaagtta aagcagatgc tatttacccg ggatatggct    360
tcctgtctga aaatgcccag cttgcccgcg agtgcgcgga aaacggcatt acttttattg    420
gcccaacccc agaggttctt gatctcaccg gtgataagtc tcgtgcggta accgccgcga    480
agaaggctgg tctgccagtt ttggcggaat ccaccccgag caaaaacatc gatgacatcg    540
ttaaaagcgc tgaaggccag acttaccca tctttgtaaa ggcagttgcc ggtggtggcg     600
gacgcggtat gcgctttgtt tcttcacctg atgagctccg caattggca acagaagcat     660
```

```
ctcgtgaagc tgaagcggca ttcggcgacg gttcggtata tgtcgaacgt gctgtgatta      720
acccccagca cattgaagtg cagatccttg gcgatcgcac tggagaagtt gtacacctt       780 atgaacgtga ctgctcactg cagcgtcgtc accaaaaagt tgtcgaaatt gcgccagcac      840
agcatttgga tccagaactg cgtgatcgca tttgtgcgga tgcagtaaag ttctgccgct      900
ccattggtta ccagggcgcg ggaaccgtgg aattcttggt cgatgaaaag ggcaaccacg      960
ttttcatcga atgaaccca cgtatccagg ttgagcacac cgtgactgaa gaagtcaccg      1020
aggtggacct ggtgaaggcg cagatgcgct tggctgctgg tgcaaccttg aaggaattgg      1080
gtctgaccca agataagatc aagacccacg gtgcagcact gcagtgccgc atcaccacgg      1140
aagatccaaa caacggcttc cgcccagata ccggaactat caccgcgtac cgctcaccag      1200
gcggagctgg cgttcgtctt gacggtgcag ctcagctcgg tggcgaaatc accgcacact      1260
ttgactccat gctggtgaaa atgacctgcc gtggttccga ctttgaaact gctgttgctc      1320
gtgcacagcg cgccgttggc gagttcaccg tgtctggtgt tgcaaccaac attggtttct      1380
tgcgtgcgtt gctgcgggaa gaggacttca cttccaagcg catcgccacc ggatttatcg      1440
gcgatcaccc acacctcctt caggctccac ctgcggatga tgagcaggga cgcatcctgg      1500
attacttggc agatgtcacc gtgaacaagc ctcatggtgt gcgtccaaag gatgttgcag      1560
caccaatcga taagctgccc aacatcaagg atctgccact gccacgcggt tcccgtgacc      1620
gcctgaagca gcttggccca gccgcgtttg ctcgtgatct ccgtgagcag gacgcactgg      1680
cagttactga taccaccttc cgcgatgcac accagtcttt gcttgcgacc cgagtccgct      1740
cattcgcact gaagcctgcg gcagaggccg tcgcaaagct gactcctgag cttttgtccg      1800
tggaggcctg ggcggcgcg acctacgatg tggcgatgcg tttcctcttt gaggatccgt      1860
gggacaggct cgacgagctg cgcgaggcga tgccgaatgt aaacattcag atgctgcttc      1920
gcggccgcaa caccgtggga tacaccccgt acccagactc cgtctgccgc cgtttgtta       1980 aggaagctgc cacctccggc gtggacatct tcccgcatct tcgacgcgctt aacgacgtct      2040 cccagatgcg tccagcaatc gacgcagtcc tggagaccaa caccgcggta gccgaggtgg      2100
ctatggctta ttctggtgat ctctctgatc caaatgaaaa gctctacacc ctggattact      2160
acctaaagat ggcagaggag atcgtcaagt ctggcgctca cattctggcc attaaggata      2220
tggctggtct gcttcgccca gctgcggtaa ccaagctggt caccgcactg cgccgtgaat      2280
tcgatctgcc agtgcacgtg cacacccacg acactgcggg tggccagttg gctacctact      2340
ttgctgcagc tcaagctggt gcagatgctg ttgacggtgc ttccgcacca ctgtctggca      2400
ccacctccca gccatccctg tctgccattg ttgctgcatt cgcgcacacc cgtcgcgata      2460
ccggtttgag cctcgaggct gtttctgacc tcgagccgta ctgggaagct gtgcgcggac      2520
tgtacctgcc atttgagtct ggaaccccag gcccaaccgg tcgcgtctac cgccacgaaa      2580
tcccaggcgg acagttgtcc aacctgcgtg cacaggccac cgcactgggc cttgctgatc      2640
gcttcgagct catcgaagac aactacgcag ccgttaatga gatgctggga cgcccaacca      2700
aggtcacccc atcctccaag gttgttggcg acctcgcact ccacctggtt ggtgcgggtg      2760
tagatccagc agactttgct gcagacccac aaaagtacga catcccagac tctgtcatcg      2820
cgttcctgcg cggcgagctt ggtaaccctc aggtggctg gccagaacca ctgcgcaccc      2880
gcgcactgga aggccgctcc gaaggcaagg cacctctgac ggaagttcct gaggaagagc      2940
aggcgcacct cgacgctgat gattccaagg aacgtcgcaa cagcctcaac cgcctgctgt      3000
tcccgaagcc aaccgaagag ttcctcgagc accgtcgccg cttcggcaac acctctgcgc      3060
```

| | |
|---|---|
| tggatgatcg tgaattcttc tacggactgg tcgagggccg cgagactttg atccgcctgc | 3120 |
| cagatgtgcg caccccactg cttgttcgcc tggatgcgat ctctgagcca gacgataagg | 3180 |
| gtatgcgcaa tgttgtggcc aacgtcaacg gccagatccg cccaatgcgt gtgcgtgacc | 3240 |
| gctccgttga gtctgtcacc gcaaccgcag aaaaggcaga ttcctccaac aagggccatg | 3300 |
| ttgctgcacc attcgctggt gttgtcactg tgactgttgc tgaaggtgat gaggtcaagg | 3360 |
| ctggagatgc agtcgcaatc atcgaggcta tgaagatgga agcaacaatc actgcttctg | 3420 |
| ttgacggcaa gattgaacgc gttgtggttc ctgctgcaac gaaggtggaa ggtggcgact | 3480 |
| tgatcgtcgt cgtttcctaa | 3500 |

<210> SEQ ID NO 8
<211> LENGTH: 771
<212> TYPE: DNA
<213> ORGANISM: Artificial Sequence
<220> FEATURE:
<223> OTHER INFORMATION: YafV_E. coli

<400> SEQUENCE: 8

| | |
|---|---|
| gtgcctggtt tgaagattac gcttttgcag caaccactgg tgtggatgga tggtcctgcc | 60 |
| aacctgcgtc attttgatcg tcaactggaa ggtattaccg ggcgcgatgt gatcgttcta | 120 |
| ccggagatgt ttaccagcgg cttgtgccatg gaagcggcag cttcgtcgct agcacaagat | 180 |
| gacgtagtga actggatgac agctaaggcg cagcagtgca atgcgctgat tgcaggcagt | 240 |
| gttgcattac aaacggagtc tggttcggtt aaccgctttt tgctggttga gccgggcggc | 300 |
| acggtacatt tttatgataa gcgtcatctg ttccgcatgg cagatgagca tctacattat | 360 |
| aaagcgggca atgcgcgagt gattgtggaa tggcgcggct ggcgtatttt gccgctggtg | 420 |
| tgctacgact tacgttttcc tgtgtggtcg cgcaatctca acgattatga cctcgccctg | 480 |
| tacgtcgcca actggcctgc tccgcgctct ctgcactggc aggcattgct gacggcccgc | 540 |
| gcgattgaga atcaggcgta tgtggcggga tgcaatcgcg tcggcagcga tggcaacggc | 600 |
| tgccattatc gcggtgacag ccgggtgatt aatccgcaag agagattat cgctactgcc | 660 |
| gacgcgcatc aggcaacgcg cattgatgcg gagctgtcga tggcagcatt gcgggaatat | 720 |
| agagaaaagt ttccggcatg gcaggatgcg gatgagttta ggttgtggtg a | 771 |

<210> SEQ ID NO 9
<211> LENGTH: 1049
<212> TYPE: DNA
<213> ORGANISM: Artificial Sequence
<220> FEATURE:
<223> OTHER INFORMATION: YafV downstream homology arm

<400> SEQUENCE: 9

| | |
|---|---|
| aaaccactgg cacgtggaga ataagctgca caggcgtctg gacgtggtaa tgaatgaaga | 60 |
| cgactacaaa ataagaagag gaaacgcagc agaattattt tcaggatac ggcacattgc | 120 |
| tattaatatt ttgacgaatg agaaggtatt caaggcaggg ttaagacgta agatgcgaaa | 180 |
| agcagccatg gacagaaact acctggcgtc agtccttgcg gggagcgggc tttcgtagta | 240 |
| ataccccgac tctccccgtc cttaaacaca accccactc accacaacct aaactcatcc | 300 |
| gcatcctgcc atgccggaaa cttttctcta tattcccgca atgctgccat cgacagctcc | 360 |
| gcatcaatgc gcgttgcctg atgcgcgtcg gcagtagcga taatctctcc ttgcggatta | 420 |
| atcacccggc tgtcaccgcg ataatggcag ccgttgccat cgctgccgac gcgattgcat | 480 |

| | |
|---|---|
| cccgccacat acgcctgatt ctcaatcgcg cgggccgtca gcaatgcctg ccagtgcaga | 540 |
| gagcgcggag caggccagtt ggcgacgtac agggcgaggt cataatcgtt gagattgcgc | 600 |
| gaccacacag gaaaacgtaa gtcgtagcac accagcggca aaatacgcca gccgcgccat | 660 |
| tccacaatca ctcgcgcatt gcccgcttta taatgtagat gctcatctgc catgcggaac | 720 |
| agatgacgct tatcataaaa atgtaccgtg ccgcccggct caaccagcaa aaagcggtta | 780 |
| accgaaccag actccgtttg taatgcaaca ctgcctgcaa tcagcgcatt gcactgctgc | 840 |
| gccttagctg tcatccagtt cactacgtca tcttgtgcta gcgacgaagc tgccgcttcc | 900 |
| atggcaaagc cgctggtaaa catctccggt agaacgatca catcgcgccc ggtaatacct | 960 |
| tccagttgac gatcaaaatg acgcaggttg gcaggaccat ccatccacac cagtggttgc | 1020 |
| tgcaaaagcg taatcttcaa accaggcac | 1049 |

<210> SEQ ID NO 10
<211> LENGTH: 1049
<212> TYPE: DNA
<213> ORGANISM: Artificial Sequence
<220> FEATURE:
<223> OTHER INFORMATION: YafV upstream homology arm

<400> SEQUENCE: 10

| | |
|---|---|
| gctgatattg gaaatatctg atttgcaaat tatcgtgtta tcgccaggct ttaggaggtt | 60 |
| aataacatgg gcaggataag ctcgggagga atgatgttta aggcaataac gacagtcgcc | 120 |
| gctctggtca tcgccaccag tgcaatggcg caggatgatt taaccattag cagccttgca | 180 |
| aagggcgaaa ccaccaaagc tgcatttaat cagatggtac aagggcataa gctgcctgcc | 240 |
| tgggtgatga aggcggtac ttatactccc gcacaaaccg taacgttggg agatgagacg | 300 |
| tatcaggtga tgagcgcgtg caaaccgcat gactgtggct cgcaacgtat cgctgtgatg | 360 |
| tggtccgaga aatctaatca gatgacgggg ctgttctcga ctattgatga gaaaacgtcg | 420 |
| caagagaaac tcacctggct gaatgtgaac gatgcgcttt cgattgatgg taaaacggtg | 480 |
| ttgttcgcgg cgttgaccgg cagcctggaa aaccatccgg atggctttaa ttttaaataa | 540 |
| ttagcggata agaaacgga gcctttcggc tccgttattc atttacgcgg cttcaacttt | 600 |
| ccgcactttc tccggcaact ttaccggctt cgtcgccagc tcttccggat caaagtcatc | 660 |
| aacgttaata ctgcgcagac ggcttttcttc agctttcacc agaatagcgg cttcatcttt | 720 |
| atcaatcagc cccttcacca gcgcgttgtg cgccagttca tccagacggg taaacggcag | 780 |
| gttttacccc agctctttac agatccgctg atgaattggg tcggcggcaa tcacatccac | 840 |
| cagcgcctct tccagcaagc caaccggatt atgctcgctc ggcgtcaggt actgaccgcg | 900 |
| accaatgcgg gaacgggtgg cgttcggcac ttgtaaaatc ttcgccactt tatgatccag | 960 |
| cttgtcagaa ggtgccagat aatgacgtcc ggtcgggaag atcaccacat tcagcagccc | 1020 |
| ggcaaccacg cggttcggga gttttgca | 1049 |

<210> SEQ ID NO 11
<211> LENGTH: 2161
<212> TYPE: DNA
<213> ORGANISM: Artificial Sequence
<220> FEATURE:
<223> OTHER INFORMATION: YafV downstream homology arm-acs RBS E.coli-T1-
yafVupstream homology arm

<400> SEQUENCE: 11

| | |
|---|---|
| aaaccactgg cacgtggaga ataagctgca caggcgtctg gacgtggtaa tgaatgaaga | 60 |

-continued

```
cgactacaaa ataagaagag gaaacgcagc agaattattt tcagggatac ggcacattgc      120
tattaatatt ttgacgaatg agaaggtatt caaggcaggg ttaagacgta agatgcgaaa      180
agcagccatg gacagaaact acctggcgtc agtccttgcg gggagcgggc tttcgtagta      240
ataccccgac tctccccgtc cttaaacaca accccactc accacaacct aaactcatcc       300
gcatcctgcc atgccggaaa cttttctcta tattcccgca atgctgccat cgacagctcc      360
gcatcaatgc gcgttgcctg atgcgcgtcg gcagtagcga taatctctcc ttgcggatta      420
atcacccggc tgtcaccgcg ataatggcag ccgttgccat cgctgccgac gcgattgcat      480
cccgccacat acgcctgatt ctcaatcgcg cgggccgtca gcaatgcctg ccagtgcaga      540
gagcgcggag caggccagtt ggcgacgtac agggcgaggt cataatcgtt gagattgcgc      600
gaccacacag gaaaacgtaa gtcgtagcac accagcggca aaatacgcca gccgcgccat      660
tccacaatca ctcgcgcatt gcccgcttta taatgtagat gctcatctgc catgcggaac      720
agatgacgct tatcataaaa atgtaccgtg ccgcccggct caaccagcaa aaagcggtta      780
accgaaccag actccgtttg taatgcaaca ctgcctgcaa tcagcgcatt gcactgctgc      840
gccttagctg tcatccagtt cactacgtca tcttgtgcta gcgacgaagc tgccgcttcc      900
atggcaaagc cgctggtaaa catctccggt agaacgatca catcgcgccc ggtaatacct      960
tccagttgac gatcaaaatg acgcaggttg gcaggaccat ccatccacac cagtggttgc     1020
tgcaaaagcg taatcttcaa accaggcacg cttttgttct ccttgtagga tgttaattga     1080
aaagcaagag ggcccgcccc cgaaggttcg gggctgatat tggaaatatc tgatttgcaa     1140
attatcgtgt tatcgccagg ctttaggagg ttaataacat gggcaggata agctcgggag     1200
gaatgatgtt taaggcaata acgacagtcg ccgctctggt catcgccacc agtgcaatgg     1260
cgcaggatga tttaaccatt agcagccttg caaagggcga aaccaccaaa gctgcattta     1320
atcagatggt acaagggcat aagctgcctg cctgggtgat gaaaggcggt acttatactc     1380
ccgcacaaac cgtaacgttg ggagatgaga cgtatcaggt gatgagcgcg tgcaaaccgc     1440
atgactgtgg ctcgcaacgt atcgctgtga tgtggtccga gaaatctaat cagatgacgg     1500
ggctgttctc gactattgat gagaaaacgt cgcaagagaa actcacctgg ctgaatgtga     1560
acgatgcgct ttcgattgat ggtaaaacgg tgttgttcgc ggcgttgacc ggcagcctgg     1620
aaaaccatcc ggatggcttt aattttaaat aattagcgga taaagaaacg gagccttttcg    1680 gctccgttat tcatttacgc ggcttcaact ttccgcactt tctccggcaa ctttaccggc     1740
ttcgtcgcca gctcttccgg atcaaagtca tcaacgttaa tactgcgcag acggcttttct   1800 tcagctttca ccagaatagc ggcttcatct ttatcaatca gccccttcac cagcgcgttg     1860
tgcgccagtt catccagacg ggtaaacggc aggtttttac ccagctcttt acagatccgc     1920
tgatgaattg ggtcggcggc aatcacatcc accagcgcct cttccagcaa gccaaccgga     1980
ttatgctcgc tcggcgtcag gtactgaccg cgaccaatgc gggaacgggt ggcgttcggc     2040
acttgtaaaa tcttcgccac tttatgatcc agcttgtcag aaggtgccag ataatgacgt     2100
ccggtcggga agatcaccac attcagcagc ccggcaacca cgcggttcgg aagttttgc      2160 a                                                                     2161
```

<210> SEQ ID NO 12
<211> LENGTH: 37
<212> TYPE: DNA
<213> ORGANISM: Artificial Sequence
<220> FEATURE:
<223> OTHER INFORMATION: T1 terminator

<400> SEQUENCE: 12
cccgaacctt cggggcggg ccctcttgct tttcaat                          37

<210> SEQ ID NO 13
<211> LENGTH: 25
<212> TYPE: DNA
<213> ORGANISM: Artificial Sequence
<220> FEATURE:
<223> OTHER INFORMATION: Acs RBS_E.coli

<400> SEQUENCE: 13
taacatccta caaggagaac aaaag                                      25

<210> SEQ ID NO 14
<211> LENGTH: 62
<212> TYPE: DNA
<213> ORGANISM: Artificial Sequence
<220> FEATURE:
<223> OTHER INFORMATION: T1 terminator-acs RBS

<400> SEQUENCE: 14
cccgaacctt cggggcggg ccctcttgct tttcaattaa catcctacaa ggagaacaaa    60
ag                                                                 62

<210> SEQ ID NO 15
<211> LENGTH: 834
<212> TYPE: DNA
<213> ORGANISM: Artificial Sequence
<220> FEATURE:
<223> OTHER INFORMATION: T1-acs rbs-yafv

<400> SEQUENCE: 15
cccgaacctt cggggcggg ccctcttgct tttcaattaa catcctacaa ggagaacaaa    60
agcgtgcctg gtttgaagat tacgcttttg cagcaaccac tggtgtggat ggatggtcct  120
gccaacctgc gtcattttga tcgtcaactg gaaggtatta ccgggcgcga tgtgatcgtt  180
ctaccggaga tgtttaccag cggctttgcc atgaagcgg cagcttcgtc gctagcacaa   240
gatgacgtag tgaactggat gacagctaag gcgcagcagt gcaatgcgct gattgcaggc  300
agtgttgcat acaaacgga gtctggttcg gttaaccgct ttttgctggt tgagccgggc   360
ggcacggtac attttatga taagcgtcat ctgttccgca tggcagatga gcatctacat   420
tataaagcgg gcaatgcgcg agtgattgtg gaatggcgcg gctggcgtat tttgccgctg   480
gtgtgctacg acttacgttt tcctgtgtgg tcgcgcaatc tcaacgatta tgacctcgcc   540
ctgtacgtcg ccaactggcc tgctccgcgc tctctgcact ggcaggcatt gctgacggcc   600
cgcgcgattg agaatcaggc gtatgtggcg ggatgcaatc gcgtcggcag cgatggcaac  660
ggctgccatt atcgcggtga cagccgggtg attaatccgc aaggagagat tatcgctact   720
gccgacgcgc atcaggcaac gcgcattgat gcggagctgt cgatggcagc attgcgggaa   780
tatagagaaa agtttccggc atggcaggat gcggatgagt ttaggttgtg gtga         834

<210> SEQ ID NO 16
<211> LENGTH: 256
<212> TYPE: PRT
<213> ORGANISM: Artificial Sequence
<220> FEATURE:
<223> OTHER INFORMATION: YafV_E. coli

<400> SEQUENCE: 16

```
Met Pro Gly Leu Lys Ile Thr Leu Leu Gln Pro Leu Val Trp Met
1               5                   10                  15

Asp Gly Pro Ala Asn Leu Arg His Phe Asp Arg Gln Leu Glu Gly Ile
            20                  25                  30

Thr Gly Arg Asp Val Ile Val Leu Pro Glu Met Phe Thr Ser Gly Phe
        35                  40                  45

Ala Met Glu Ala Ala Ala Ser Ser Leu Ala Gln Asp Asp Val Val Asn
    50                  55                  60

Trp Met Thr Ala Lys Ala Gln Gln Cys Asn Ala Leu Ile Ala Gly Ser
65                  70                  75                  80

Val Ala Leu Gln Thr Glu Ser Gly Ser Val Asn Arg Phe Leu Leu Val
                85                  90                  95

Glu Pro Gly Gly Thr Val His Phe Tyr Asp Lys Arg His Leu Phe Arg
            100                 105                 110

Met Ala Asp Glu His Leu His Tyr Lys Ala Gly Asn Ala Arg Val Ile
        115                 120                 125

Val Glu Trp Arg Gly Trp Arg Ile Leu Pro Leu Val Cys Tyr Asp Leu
130                 135                 140

Arg Phe Pro Val Trp Ser Arg Asn Leu Asn Asp Tyr Asp Leu Ala Leu
145                 150                 155                 160

Tyr Val Ala Asn Trp Pro Ala Pro Arg Ser Leu His Trp Gln Ala Leu
                165                 170                 175

Leu Thr Ala Arg Ala Ile Glu Asn Gln Ala Tyr Val Ala Gly Cys Asn
            180                 185                 190

Arg Val Gly Ser Asp Gly Asn Gly Cys His Tyr Arg Gly Asp Ser Arg
        195                 200                 205

Val Ile Asn Pro Gln Gly Glu Ile Ile Ala Thr Ala Asp Ala His Gln
    210                 215                 220

Ala Thr Arg Ile Asp Ala Glu Leu Ser Met Ala Ala Leu Arg Glu Tyr
225                 230                 235                 240

Arg Glu Lys Phe Pro Ala Trp Gln Asp Ala Asp Glu Phe Arg Leu Trp
                245                 250                 255
```

<210> SEQ ID NO 17
<211> LENGTH: 621
<212> TYPE: DNA
<213> ORGANISM: Artificial Sequence
<220> FEATURE:
<223> OTHER INFORMATION: RhtC_E.coli

<400> SEQUENCE: 17

```
atgttgatgt tatttctcac cgtcgccatg gtgcacattg tggcgcttat gagccccggt      60
ccgatttct tttttgtctc tcagaccgct gtcagtcgtt cccgtaaaga agcgatgatg      120
ggcgtgctgg gcattacctg cggcgtaatg gtttgggctg ggattgcgct gcttggcctg      180
catttgatta tcgaaaaaat ggcctggctg catacgctga ttatggtggg cggtggcctg      240
tatctctgct ggatgggtta ccagatgcta cgtggtgcac tgaaaaaaga ggcggtttct      300
gcacctgcgc acaggtcga gctggcgaaa agtgggcgca gtttcctgaa aggtttactg      360
accaatctcg ctaatccgaa agcgattatc tactttggct cggtgttctc attgtttgtc      420
ggtgataacg ttggcactac cgcgcgctgg ggcattttg cgctgatcat tgtcgaaacg      480
ctggcgtggt ttaccgtcgt tgccagcctg tttgccctgc cgcaaatgcg ccgtggttat      540
caacgtctgg cgaagtggat tgatggtttt gccggggcgt tatttgccgg atttggcatt      600
catttgatta tttcgcggtg a                                                621
```

<210> SEQ ID NO 18
<211> LENGTH: 771
<212> TYPE: DNA
<213> ORGANISM: Artificial Sequence
<220> FEATURE:
<223> OTHER INFORMATION: PrhtC-rhtC_E.coli

<400> SEQUENCE: 18

| | | | | | | |
|---|---|---|---|---|---|---|
| ggcgttggga | tgcgcaagct | ggaacgcttt | ggcaaaccgt | ttatggcgct | gattcgtgcg | 60 |
| catgttgatg | gcgatgacga | agagtagtca | gcagcataaa | aaagtgccag | tatgaagact | 120 |
| ccgtaaacgt | ttcccccgcg | agtcaaatgt | atgttgatgt | tatttctcac | cgtcgccatg | 180 |
| gtgcacattg | tggcgcttat | gagccccggt | cccgatttct | tttttgtctc | tcagaccgct | 240 |
| gtcagtcgtt | cccgtaaaga | agcgatgatg | ggcgtgctgg | gcattacctg | cggcgtaatg | 300 |
| gtttgggctg | ggattgcgct | gcttggcctg | catttgatta | tcgaaaaaat | ggcctggctg | 360 |
| catacgctga | ttatggtggg | cggtggcctg | tatctctgct | ggatgggtta | ccagatgcta | 420 |
| cgtggtgcac | tgaaaaaaga | ggcggtttct | gcacctgcgc | cacaggtcga | gctggcgaaa | 480 |
| agtgggcgca | gtttcctgaa | aggtttactg | accaatctcg | ctaatccgaa | agcgattatc | 540 |
| tactttggct | cggtgttctc | attgtttgtc | ggtgataacg | ttggcactac | cgcgcgctgg | 600 |
| ggcattttg | cgctgatcat | tgtcgaaacg | ctggcgtggt | ttaccgtcgt | tgccagcctg | 660 |
| tttgccctgc | cgcaaatgcg | ccgtggttat | caacgtctgg | cgaagtggat | tgatggtttt | 720 |
| gccggggcgt | tatttgccgg | atttggcatt | catttgatta | tttcgcggtg | a | 771 |

<210> SEQ ID NO 19
<211> LENGTH: 1051
<212> TYPE: DNA
<213> ORGANISM: Artificial Sequence
<220> FEATURE:
<223> OTHER INFORMATION: RhtC upstream homology arm_E.coli

<400> SEQUENCE: 19

| | | | | | | |
|---|---|---|---|---|---|---|
| attccagcgc | gatgacctgc | aaattgtggt | ggcgacggtg | gcgttcggca | tgggcatcaa | 60 |
| taaaccaaac | gttcgcttcg | tggtccactt | tgatattccg | cgcaatatcg | aatcctatta | 120 |
| tcaggaaacc | ggacgcgccg | ggcgtgatgg | cctgcccgcg | gaagcgatgc | tgttttacga | 180 |
| tccggctgat | atggcgtggc | tgcgccgttg | tctggaagag | aagccgcagg | ggcagttgca | 240 |
| ggatatcgag | cgccacaaac | tcaatgcgat | gggcgcgttt | gccgaagcgc | aaacttgccg | 300 |
| tcgtctggta | ttgctgaact | attttggcga | agggcgtcag | gagccgtgcg | ggaactgcga | 360 |
| tatctgcctc | gatccgccga | aacagtacga | cggttcaacc | gatgctcaga | ttgcccttc | 420 |
| caccattggt | cgtgtgaatc | agcggtttgg | gatgggttat | gtggtggaag | tgattcgtgg | 480 |
| tgctaataac | cagcgtatcc | gcgactatgg | tcatgacaaa | ctgaaagtct | atggcatggg | 540 |
| ccgtgataaa | agccatgaac | attgggtgag | cgtgatccgc | cagctgattc | acctcggcct | 600 |
| ggtgacgcaa | atattgccc | agcattctgc | cctacaactg | acagaggccg | cgcgcccggt | 660 |
| gctgcgcggc | gaatcctctt | tgcaacttgc | cgtgccgcgt | atcgtggcgc | tcaaaccgaa | 720 |
| agcgatgcag | aaatcgttcg | gcggcaacta | tgatcgcaaa | ctgttcgcca | aattacgcaa | 780 |
| actgcgtaaa | tcgatagccg | atgaaagtaa | tgtcccgccg | tacgtggtgt | taacgacgc | 840 |
| aaccttgatt | gagatggctg | aacagatgcc | gatcaccgcc | agcgaaatgc | tcagcgttaa | 900 |
| cggcgttggg | atgcgcaagc | tggaacgctt | tggcaaaccg | tttatggcgc | tgattcgtgc | 960 |

```
gcatgttgat ggcgatgacg aagagtagtc agcagcataa aaaagtgcca gtatgaagac   1020
tccgtaaacg tttcccccgc gagtcaaatg t                                  1051

<210> SEQ ID NO 20
<211> LENGTH: 1028
<212> TYPE: DNA
<213> ORGANISM: Artificial Sequence
<220> FEATURE:
<223> OTHER INFORMATION: Rhtc downstream homology arm_e.coli

<400> SEQUENCE: 20
atgttgatgt tatttctcac cgtcgccatg gtgcacattg tggcgcttat gagccccggt     60
cccgatttct tttttgtctc tcagaccgct gtcagtcgtt cccgtaaaga agcgatgatg    120
ggcgtgctgg gcattacctg cggcgtaatg gtttgggctg ggattgcgct gcttggcctg    180
catttgatta tcgaaaaaat ggcctggctg catacgctga ttatggtggg cggtggcctg    240
tatctctgct ggatgggtta ccagatgcta cgtggtgcac tgaaaaaaga gcggttttct    300
gcacctgcgc acaggtcga gctggcgaaa agtgggcgca gtttcctgaa aggtttactg    360
accaatctcg ctaatccgaa agcgattatc tactttggct cggtgttctc attgtttgtc    420
ggtgataacg ttggcactac cgcgcgctgg ggcattttttg cgctgatcat tgtcgaaacg    480
ctggcgtggt ttaccgtcgt tgccagcctg tttgccctgc gcaaatgcg ccgtggttat    540 caacgtctgg cgaagtggat tgatggtttt gccggggcgt tatttgccgg atttggcatt    600
catttgatta tttcgcggtg atgccagacg cgtcttcaga gtaagtcgga taaggcgttt    660
acgccgcatc cgacattatt tttcacgcat gcctcgccga tgctaacagc gctcccacca    720
gcataaacaa cgagccgaaa atcttattca gcgccttcat ctgctttggt cctttaatcc    780
atagagcaat ccgttgagca agggtggcgt aaccgatcat cacaataata tcgaccacaa    840
tagtggtgac gccgagcacg atatactgca tcagttgcgg ctgttgcggc atgatgaatt    900
gcggaaatag cgccgccaga aacacaatac ttttgggatt ggtgagattc acaaaaactg    960
cgcgctggaa caaatgtcga cgcgattgag tagaggccag cgatttaagg tcaattgcac   1020
cagcggcg                                                           1028

<210> SEQ ID NO 21
<211> LENGTH: 2106
<212> TYPE: DNA
<213> ORGANISM: Artificial Sequence
<220> FEATURE:
<223> OTHER INFORMATION: RhtC upstream homology arm-synthetic RBS-rhtC
      downstream homology arm

<400> SEQUENCE: 21
attccagcgc gatgacctgc aaattgtggt ggcgacggtg gcgttcggca tgggcatcaa     60
taaaccaaac gttcgcttcg tggtccactt tgatattccg cgcaatatcg aatcctatta    120
tcaggaaacc ggacgcgccg ggcgtgatgg cctgcccgcg aagcgatgc tgttttacga    180 tccggctgat atggcgtggc tgcgccgttg tctggaagag aagccgcagg ggcagttgca    240
ggatatcgag cgccacaaac tcaatgcgat gggcgcgttt gccgaagcgc aaacttgccg    300
tcgtctggta ttgctgaact attttggcga agggcgtcag gagccgtgcg gaactgcga    360 tatctgcctc gatccgccga aacagtacga cggttcaacc gatgctcaga ttgcccttc    420 caccattggt cgtgtgaatc agcggttttg gatgggttat gtggtggaag tgattcgtgg    480
tgctaataac cagcgtatcc gcgactatgg tcatgacaaa ctgaaagtct atggcatggg    540
```

```
ccgtgataaa agccatgaac attgggtgag cgtgatccgc cagctgattc acctcggcct      600
ggtgacgcaa atattgccc agcattctgc cctacaactg acagaggccg cgcgcccggt       660
gctgcgcggc gaatcctctt tgcaacttgc cgtgccgcgt atcgtggcgc tcaaaccgaa      720
agcgatgcag aaatcgttcg gcggcaacta tgatcgcaaa ctgttcgcca aattacgcaa      780
actgcgtaaa tcgatagccg atgaaagtaa tgtcccgccg tacgtggtgt taacgacgc       840 aaccttgatt gagatggctg aacagatgcc gatcaccgcc agcgaaatgc tcagcgttaa      900
cggcgttggg atgcgcaagc tggaacgctt tggcaaaccg tttatggcgc tgattcgtgc      960
gcatgttgat ggcgatgacg aagagtagtc agcagcataa aaaagtgcca gtatgaagac      1020
tccgtaaacg tttcccccgc gagtcaaatg taattgaata aactaaggag gttaaagtat      1080
gttgatgtta tttctcaccg tcgccatggt gcacattgtg gcgcttatga gccccggtcc      1140
cgatttcttt tttgtctctc agaccgctgt cagtcgttcc cgtaaagaag cgatgatggg      1200
cgtgctgggc attacctgcg gcgtaatggt ttgggctggg attgcgctgc ttggcctgca      1260
tttgattatc gaaaaaatgg cctggctgca tacgctgatt atggtgggcg gtggcctgta      1320
tctctgctgg atgggttacc agatgctacg tggtgcactg aaaaaagagg cggtttctgc      1380
acctgcgcca caggtcgagc tggcgaaaag tgggcgcagt ttcctgaaag gtttactgac      1440
caatctcgct aatccgaaag cgattatcta ctttggctcg gtgttctcat tgtttgtcgg      1500
tgataacgtt ggcactaccg cgcgctgggg catttttgcg ctgatcattg tcgaaacgct      1560
ggcgtggttt accgtcgttg ccagcctgtt tgccctgccg caaatgcgcc gtggttatca      1620
acgtctggcg aagtggattg atggttttgc cggggcgtta tttgccggat ttggcattca      1680
tttgattatt tcgcggtgat gccagacgcg tcttcagagt aagtcggata aggcgtttac      1740
gccgcatccg acattatttt tcacgcatgc ctcgccgatg ctaacagcgc tcccaccagc      1800
ataaacaacg agccgaaaat cttattcagc gccttcatct gctttggtcc tttaatccat      1860
agagcaatcc gttgagcaag ggtggcgtaa ccgatcatca caataatatc gaccacaata      1920
gtggtgacgc cgagcacgat atactgcatc agttgcggct gttgcggcat gatgaattgc      1980
ggaaatagcg ccgccagaaa cacaatactt tgggattgg tgagattcac aaaaactgcg       2040
cgctggaaca aatgtcgacg cgattgagta gaggccagca atttaaggtc aattgcacca      2100
gcggcg                                                                2106

<210> SEQ ID NO 22
<211> LENGTH: 150
<212> TYPE: DNA
<213> ORGANISM: Artificial Sequence
<220> FEATURE:
<223> OTHER INFORMATION: PrhtC_E.coli_promoter

<400> SEQUENCE: 22
ggcgttggga tgcgcaagct ggaacgcttt ggcaaaccgt ttatggcgct gattcgtgcg       60
catgttgatg gcgatgacga agagtagtca gcagcataaa aaagtgccag tatgaagact      120
ccgtaaacgt ttcccccgcg agtcaaatgt                                      150

<210> SEQ ID NO 23
<211> LENGTH: 27
<212> TYPE: DNA
<213> ORGANISM: Artificial Sequence
<220> FEATURE:
<223> OTHER INFORMATION: Synthetic RBS

<400> SEQUENCE: 23
```

```
aattgaataa actaaggagg ttaaagt                                           27
```

<210> SEQ ID NO 24
<211> LENGTH: 798
<212> TYPE: DNA
<213> ORGANISM: Artificial Sequence
<220> FEATURE:
<223> OTHER INFORMATION: PrhtC-synthetic RBS-rhtC

<400> SEQUENCE: 24

```
ggcgttggga tgcgcaagct ggaacgcttt ggcaaaccgt ttatggcgct gattcgtgcg        60
catgttgatg gcgatgacga agagtagtca gcagcataaa aaagtgccag tatgaagact       120
ccgtaaacgt ttcccccgcg agtcaaatgt aattgaataa actaaggagg ttaaagtatg       180
ttgatgttat ttctcaccgt cgccatggtg cacattgtgg cgcttatgag ccccggtccc       240
gatttctttt ttgtctctca gaccgctgtc agtcgttccc gtaaagaagc gatgatgggc       300
gtgctgggca ttacctgcgg cgtaatggtt tgggctggga ttgcgctgct ggcctgcat        360
ttgattatcg aaaaaatggc ctggctgcat acgctgatta tggtgggcgg tggcctgtat       420
ctctgctgga tgggttacca gatgctacgt ggtgcactga aaaagaggc ggtttctgca        480
cctgcgccac aggtcgagct ggcgaaaagt gggcgcagtt tcctgaaagg tttactgacc       540
aatctcgcta atccgaaagc gattatctac tttggctcgg tgttctcatt gtttgtcggt       600
gataacgttg gcactaccgc gcgctggggc attttgcgc tgatcattgt cgaaacgctg        660
gcgtggtta ccgtcgttgc cagcctgttt gccctgccgc aaatgcgccg tggttatcaa        720
cgtctggcga agtggattga tggttttgcc ggggcgttat ttgccggatt tggcattcat       780
ttgattattt cgcggtga                                                     798
```

<210> SEQ ID NO 25
<211> LENGTH: 206
<212> TYPE: PRT
<213> ORGANISM: Artificial Sequence
<220> FEATURE:
<223> OTHER INFORMATION: RhtC_E.coli

<400> SEQUENCE: 25

```
Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Leu Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
                100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
```

| | | 145 | | | 150 | | | | 155 | | | | 160 | |
|---|---|---|---|---|---|---|---|---|---|---|---|---|---|---|

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

```
<210> SEQ ID NO 26
<211> LENGTH: 1545
<212> TYPE: DNA
<213> ORGANISM: Artificial Sequence
<220> FEATURE:
<223> OTHER INFORMATION: IlvA_E. coli

<400> SEQUENCE: 26
atggctgact cgcaacccct gtccggtgct ccggaaggtg ccgaatattt aagagcagtg      60
ctgcgcgcgc cggtttacga ggcggcgcag gttacgccgc tacaaaaaat ggaaaaactg     120
tcgtcgcgtc ttgataacgt cattctggtg aagcgcgaag atcgccagcc agtgcacagc     180
tttaagctgc gcggcgcata cgccatgatg gcgggcctga cggaagaaca gaaagcgcac     240
ggcgtgatca ctgcttctgc gggtaaccac gcgcagggcg tcgcgttttc ttctgcgcgg     300
ttaggcgtga aggccctgat cgttatgcca accgccaccg ccgacatcaa gtcgacgcg      360
gtgcgcggct cggcggcga agtgctgctc cacggcgcga ctttgatga agcgaaagcc      420
aaagcgatcg aactgtcaca gcagcagggg ttcacctggg tgccgccgtt cgaccatccg     480
atggtgattg ccgggcaagg cacgctggcg ctggaactgc tccagcagga cgcccatctc     540
gaccgcgtat ttgtgccagt cggcggcggc ggtctggctg ctggcgtggc ggtgctgatc     600
aaacaactga tgccgcaaat caaagtgatc gccgtagaag cggaagactc cgcctgcctg     660
aaagcagcgc tggatgcggg tcatccggtt gatctgccgc gcgtagggct atttgctgaa     720
ggcgtagcgg taaaacgcat cggtgacgaa accttccgtt atgccagga gtatctcgac     780
gacatcatca ccgtcgatag cgatgcgatc tgtgcggcga tgaaggattt attcgaagat     840
gtgcgcgcgg tggcggaacc tctggcgcg ctggcgctgg cgggaatgaa aaaatatatc     900
gccctgcaca acattcgcgg cgaacggctg cgcatattc tttccggtgc caacgtgaac     960
ttccacggcc tgcgctacgt ctcagaacgc tgcgaactgg cgaacagcg tgaagcgttg    1020
ttggcggtga ccattccgga agaaaaaggc agcttcctca aattctgcca actgcttggc    1080
gggcgttcgg tcaccgagtt caactaccgt tttgccgatg ccaaaaacgc tgcatctttt    1140
gtcggtgtgc gcctgagccg cggcctcgaa gagcgcaaag aaattttgca gatgctcaac    1200
gacgcgggct acagcgtggt tgatctctcc gacgacgaaa tggcgaagct acacgtgcgc    1260
tatatggtcg gcggacgtcc atcgcatccg ttgcaggaac gcctctacag cttcgaattc    1320
ccggaatcac cggcgcgct gctgcgcttc tcaacacgc tgggtacgta ctggaacatt    1380
tctttgttcc actatcgcag ccatggcacc gactacgggc gcgtactggc ggcgttcgaa    1440
cttggcgacc atgaaccgga tttcgaaacc cggctgaatg agctgggcta cgattgccac    1500
gacgaaacca ataacccggc gttcaggttc tttttggcgg gttag                   1545

<210> SEQ ID NO 27
<211> LENGTH: 514
<212> TYPE: PRT
<213> ORGANISM: Artificial Sequence
<220> FEATURE:
```

<223> OTHER INFORMATION: IlvA_E. coli

<400> SEQUENCE: 27

```
Met Ala Asp Ser Gln Pro Leu Ser Gly Ala Pro Glu Gly Ala Glu Tyr
  1               5                  10                  15

Leu Arg Ala Val Leu Arg Ala Pro Val Tyr Glu Ala Ala Gln Val Thr
             20                  25                  30

Pro Leu Gln Lys Met Glu Lys Leu Ser Ser Arg Leu Asp Asn Val Ile
             35                  40                  45

Leu Val Lys Arg Glu Asp Arg Gln Pro Val His Ser Phe Lys Leu Arg
         50                  55                  60

Gly Ala Tyr Ala Met Met Ala Gly Leu Thr Glu Glu Gln Lys Ala His
 65                  70                  75                  80

Gly Val Ile Thr Ala Ser Ala Gly Asn His Ala Gln Gly Val Ala Phe
                 85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
            115                 120                 125

Leu Leu His Gly Ala Asn Phe Asp Glu Ala Lys Ala Lys Ala Ile Glu
        130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
        195                 200                 205

Val Ile Ala Val Glu Ala Glu Asp Ser Ala Cys Leu Lys Ala Ala Leu
210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
            260                 265                 270

Ala Met Lys Asp Leu Phe Glu Asp Val Arg Ala Val Ala Glu Pro Ser
        275                 280                 285

Gly Ala Leu Ala Leu Ala Gly Met Lys Lys Tyr Ile Ala Leu His Asn
    290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
            340                 345                 350

Leu Lys Phe Cys Gln Leu Leu Gly Gly Arg Ser Val Thr Glu Phe Asn
        355                 360                 365

Tyr Arg Phe Ala Asp Ala Lys Asn Ala Cys Ile Phe Val Gly Val Arg
    370                 375                 380

Leu Ser Arg Gly Leu Glu Glu Arg Lys Glu Ile Leu Gln Met Leu Asn
385                 390                 395                 400
```

```
Asp Gly Gly Tyr Ser Val Val Asp Leu Ser Asp Glu Met Ala Lys
                405                 410                 415

Leu His Val Arg Tyr Met Val Gly Gly Arg Pro Ser His Pro Leu Gln
            420                 425                 430

Glu Arg Leu Tyr Ser Phe Glu Phe Pro Glu Ser Pro Gly Ala Leu Leu
        435                 440                 445

Arg Phe Leu Asn Thr Leu Gly Thr Tyr Trp Asn Ile Ser Leu Phe His
    450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Asn Asn Pro Ala Phe Arg Phe Phe Leu
            500                 505                 510

Ala Gly

<210> SEQ ID NO 28
<211> LENGTH: 1050
<212> TYPE: DNA
<213> ORGANISM: Artificial Sequence
<220> FEATURE:
<223> OTHER INFORMATION: IlvA upstream homology arm_E.coli

<400> SEQUENCE: 28
```

| | | | | | |
|---|---|---|---|---|---|
| catgacgctg | gatatcgcga | tgggtggatc | gactaacacc | gtacttcacc | tgctggcggc      60 |
| ggcgcaggaa | gcggaaatcg | acttcaccat | gagtgatatc | gataagcttt | cccgcaaggt     120 |
| tccacagctg | tgtaaagttg | cgccgagcac | ccagaaatac | catatggaag | atgttcaccg     180 |
| tgctggtggt | gttatcggta | ttctcggcga | actggatcgc | gcggggttac | tgaaccgtga     240 |
| tgtgaaaaac | gtacttggcc | tgacgttgcc | gcaaacgctg | aacaatacg | acgttatgct     300 |
| gacccaggat | gacgcggtaa | aaatatgtt | ccgcgcaggt | cctgcaggca | ttcgtaccac     360 |
| acaggcattc | tcgcaagatt | gccgttggga | tacgctggac | gacgatcgcg | ccaatggctg     420 |
| tatccgctcg | ctggaacacg | cctacagcaa | agacggcggc | ctggcggtgc | tctacggtaa     480 |
| ctttgcggaa | aacggctgca | tcgtgaaaac | ggcaggcgtc | gatgacagca | tcctcaaatt     540 |
| caccggcccg | cgcaaagtgt | acgaaagcca | ggacgatgcg | gtagaagcga | ttctcggcgg     600 |
| taaagttgtc | gccggagatg | tggtagtaat | tcgctatgaa | ggcccgaaag | gcggtccggg     660 |
| gatgcaggaa | atgctctacc | caaccagctt | cctgaaatca | atgggtctcg | gcaaagcctg     720 |
| tgcgctgatc | accgacggtc | gtttctctgg | tggcacctct | ggtctttcca | tcggccacgt     780 |
| ctcaccggaa | gcggcaagcg | gcggcagcat | tggcctgatt | gaagatggtg | acctgatcgc     840 |
| tatcgacatc | ccgaaccgtg | gcattcagtt | acaggtaagc | gatgccgaac | tggcggcgcg     900 |
| tcgtgaagcg | caggacgctc | gaggtgacaa | agcctggacg | ccgaaaaatc | gtgaacgtca     960 |
| ggtctccttt | gccctgcgtg | cttatgccag | cctggcaacc | agcgccgaca | aaggcgcggt    1020 |
| gcgcgataaa | tcgaaactgg | ggggttaata | | |            1050 |

```
<210> SEQ ID NO 29
<211> LENGTH: 1048
<212> TYPE: DNA
<213> ORGANISM: Artificial Sequence
<220> FEATURE:
<223> OTHER INFORMATION: Ilva downstream homology arm_e.coli

<400> SEQUENCE: 29
```

| | |
|---|---|
| ggctgactcg caacccctgt ccggtgctcc ggaaggtgcc gaatatttaa gagcagtgct | 60 |
| gcgcgcgccg gtttacgagg cggcgcaggt tacgccgcta caaaaaatgg aaaaactgtc | 120 |
| gtcgcgtctt gataacgtca ttctggtgaa gcgcgaagat cgccagccag tgcacagctt | 180 |
| taagctgcgc ggcgcatacg ccatgatggc gggcctgacg gaagaacaga aagcgcacgg | 240 |
| cgtgatcact gcttctgcgg gtaaccacgc gcagggcgtc gcgttttctt ctgcgcggtt | 300 |
| aggcgtgaag gccctgatcg ttatgccaac cgccaccgcc gacatcaaag tcgacgcggt | 360 |
| gcgcggcttc ggcggcgaag tgctgctcca cggcgcgaac tttgatgaag cgaaagccaa | 420 |
| agcgatcgaa ctgtcacagc agcagggggtt cacctgggtg ccgccgttcg accatccgat | 480 |
| ggtgattgcc gggcaaggca cgctggcgct ggaactgctc cagcaggacg cccatctcga | 540 |
| ccgcgtattt gtgccagtcg gcggcggcgg tctggctgct ggcgtggcgg tgctgatcaa | 600 |
| acaactgatg ccgcaaatca aagtgatcgc cgtagaagcg gaagactccg cctgcctgaa | 660 |
| agcagcgctg gatgcgggtc atccggttga tctgccgcgc gtagggctat ttgctgaagg | 720 |
| cgtagcggta aaacgcatcg gtgacgaaac cttccgttta tgccaggagt atctcgacga | 780 |
| catcatcacc gtcgatagcg atgcgatctg tgcggcgatg aaggatttat tcgaagatgt | 840 |
| gcgcgcggtg gcggaaccct ctggcgcgct ggcgctggcg ggaatgaaaa aatatatcgc | 900 |
| cctgcacaac attcgcggcg aacggctggc gcatattctt tccggtgcca acgtgaactt | 960 |
| ccacggcctg cgctacgtct cagaacgctg cgaactgggc gaacagcgtg aagcgttgtt | 1020 |
| ggcggtgacc attccggaag aaaaaggc | 1048 |

<210> SEQ ID NO 30
<211> LENGTH: 2161
<212> TYPE: DNA
<213> ORGANISM: Artificial Sequence
<220> FEATURE:
<223> OTHER INFORMATION: IlvA upstream homology arm- T1-cro RBS-ilvA
      downstream homology arm

<400> SEQUENCE: 30

| | |
|---|---|
| catgacgctg gatatcgcga tgggtggatc gactaacacc gtacttcacc tgctggcggc | 60 |
| ggcgcaggaa gcggaaatcg acttcaccat gagtgatatc gataagcttt cccgcaaggt | 120 |
| tccacagctg tgtaaagttg cgccgagcac ccagaaatac catatggaag atgttcaccg | 180 |
| tgctggtggt gttatcggta ttctcggcga actggatcgc gcggggttac tgaaccgtga | 240 |
| tgtgaaaaac gtacttggcc tgacgttgcc gcaaacgctg aacaatacg acgttatgct | 300 |
| gacccaggat gacgcggtaa aaatatgtt ccgcgcaggt cctgcaggca ttcgtaccac | 360 |
| acaggcattc tcgcaagatt gccgttggga tacgctggac gacgatcgcg ccaatggctg | 420 |
| tatccgctcg ctggaacacg cctacagcaa agacggcggc ctggcggtgc tctacgtaa | 480 |
| ctttgcggaa aacggctgca tcgtgaaaac ggcaggcgtc gatgacagca tcctcaaatt | 540 |
| caccggcccg gcgaaagtgt acgaaagcca ggacgatgcg gtagaagcga ttctcggcgg | 600 |
| taaagttgtc gccggagatg tggtagtaat tcgctatgaa ggcccgaaag cggtccggg | 660 |
| gatgcaggaa atgctctacc caaccagctt cctgaaatca atgggtctcg gcaaagcctg | 720 |
| tgcgctgatc accgacggtc gtttctctgg tggcacctct ggtctttcca tcggccacgt | 780 |
| ctcaccggaa gcggcaagcg gcggcagcat tggcctgatt gaagatggtg acctgatcgc | 840 |
| tatcgacatc ccgaaccgtg gcattcagtt acaggtaagc gatgccgaac tggcggcgcg | 900 |
| tcgtgaagcg caggacgctc gaggtgacaa agcctggacg ccgaaaaatc gtgaacgtca | 960 |

```
ggtctccttt gccctgcgtg cttatgccag cctggcaacc agcgccgaca aaggcgcggt    1020
gcgcgataaa tcgaaactgg ggggttaata cccgaacctt cggggcgggc cctcttgct    1080 tttcaatggt tgcatgtact aaggaggttg tatggctgac tcgcaacccc tgtccggtgc    1140
tccggaaggt gccgaatatt taagagcagt gctgcgcgcg ccggtttacg aggcggcgca    1200
ggttacgccg ctacaaaaaa tggaaaaact gtcgtcgcgt cttgataacg tcattctggt    1260
gaagcgcgaa gatcgccagc cagtgcacag ctttaagctg cgcggcgcat acgccatgat    1320
ggcgggcctg acggaagaac agaaagcgca cggcgtgatc actgcttctg cgggtaaacca   1380 cgcgcagggc gtcgcgtttt cttctgcgcg gttaggcgtg aaggccctga tcgttatgcc    1440
aaccgccacc gccgacatca agtcgacgc ggtgcgcggc ttcgcggcg aagtgctgct      1500 ccacggcgcg aactttgatg aagcgaaagc caaagcgatc gaactgtcac agcagcaggg    1560
gttcacctgg gtgccgccgt tcgaccatcc gatggtgatt gccgggcaag gcacgctggc    1620
gctggaactg ctccagcagg acgcccatct cgaccgcgta tttgtgccag tcggcggcgg    1680
cggtctggct gctggcgtgg cggtgctgat caaacaactg atgccgcaaa tcaaagtgat    1740
cgccgtagaa gcggaagact ccgcctgcct gaaagcagcg ctggatgcgg gtcatccggt    1800
tgatctgccg cgcgtagggc tatttgctga aggcgtagcg gtaaaacgca tcggtgacga    1860
aaccttccgt ttatgccagg agtatctcga cgacatcatc accgtcgata gcgatgcgat    1920
ctgtgcggcg atgaaggatt tattcgaaga tgtgcgcgcg gtggcggaac cctctggcgc    1980
gctggcgctg gcgggaatga aaaatatat cgccctgcac aacattgcg gcgaacggct      2040 ggcgcatatt ctttccggtg ccaacgtgaa cttccacggc ctgcgctacg tctcagaacg    2100
ctgcgaactg ggcgaacagc gtgaagcgtt gttggcggtg accattccgg aagaaaaagg    2160
c                                                                    2161

<210> SEQ ID NO 31
<211> LENGTH: 61
<212> TYPE: DNA
<213> ORGANISM: Artificial Sequence
<220> FEATURE:
<223> OTHER INFORMATION: T1 terminator-cro RBS

<400> SEQUENCE: 31
cccgaacctt cggggcgggc cctcttgct tttcaatggt tgcatgtact aaggaggttg     60
t                                                                    61

<210> SEQ ID NO 32
<211> LENGTH: 24
<212> TYPE: DNA
<213> ORGANISM: Artificial Sequence
<220> FEATURE:
<223> OTHER INFORMATION: Cro RBS_E.coli

<400> SEQUENCE: 32
ggttgcatgt actaaggagg ttgt                                           24

<210> SEQ ID NO 33
<211> LENGTH: 1606
<212> TYPE: DNA
<213> ORGANISM: Artificial Sequence
<220> FEATURE:
<223> OTHER INFORMATION: T1-cro RBS-ilvA

<400> SEQUENCE: 33
cccgaacctt cggggcgggc cctcttgct tttcaatggt tgcatgtact aaggaggttg     60
```

```
tatggctgac tcgcaacccc tgtccggtgc tccggaaggt gccgaatatt taagagcagt      120
gctgcgcgcg ccggtttacg aggcggcgca ggttacgccg ctacaaaaaa tggaaaaact      180
gtcgtcgcgt cttgataacg tcattctggt gaagcgcgaa gatcgccagc cagtgcacag      240 cttttaagctg cgcggcgcat acgccatgat ggcgggcctg acggaagaac agaaagcgca     300
cggcgtgatc actgcttctg cgggtaacca cgcgcagggc gtcgcgtttt cttctgcgcg      360
gttaggcgtg aaggccctga tcgttatgcc aaccgccacc gccgacatca agtcgacgc       420 ggtgcgcggc ttcggcggcg aagtgctgct ccacggcgcg aactttgatg aagcgaaagc      480
caaagcgatc gaactgtcac agcagcaggg gttcacctgg gtgccgccgt tcgaccatcc      540
gatggtgatt gccgggcaag gcacgctggc gctggaactg ctccagcagg acgcccatct      600
cgaccgcgta tttgtgccag tcggcggcgg cggtctggct gctggcgtgg cggtgctgat      660
caaacaactg atgccgcaaa tcaaagtgat cgccgtagaa gcggaagact ccgcctgcct      720
gaaagcagcg ctggatgcgg gtcatccggt tgatctgccg cgcgtagggc tatttgctga      780
aggcgtagcg gtaaaacgca tcggtgacga aaccttccgt ttatgccagg agtatctcga      840
cgacatcatc accgtcgata gcgatgcgat ctgtgcggcg atgaaggatt tattcgaaga      900
tgtgcgcgcg gtggcggaac cctctggcgc gctggcgctg gcgggaatga aaaaatatat      960
cgccctgcac aacattcgcg gcgaacggct ggcgcatatt ctttccggtg ccaacgtgaa     1020
cttccacggc ctgcgctacg tctcagaacg ctgcgaactg ggcgaacagc gtgaagcgtt     1080
gttggcggtg accattccgg aagaaaaagg cagcttcctc aaattctgcc aactgcttgg     1140
cgggcgttcg gtcaccgagt tcaactaccg ttttgccgat gccaaaaacg cctgcatctt     1200
tgtcggtgtg cgcctgagcc gcggcctcga agagcgcaaa gaaattttgc agatgctcaa     1260
cgacggcggc tacagcgtgg ttgatctctc cgacgacgaa atggcgaagc tacacgtgcg     1320
ctatatggtc ggcggacgtc catcgcatcc gttgcaggaa cgcctctaca gcttcgaatt     1380
cccggaatca ccgggcgcgc tgctgcgctt cctcaacacg ctgggtacgt actggaacat     1440
ttctttgttc cactatcgca gccatggcac cgactacggg cgcgtactgg cggcgttcga     1500
acttggcgac catgaaccgg atttcgaaac ccggctgaat gagctgggct acgattgcca     1560
cgacgaaacc aataacccgg cgttcaggtt cttttttggcg ggttag                   1606
```

<210> SEQ ID NO 34
<211> LENGTH: 7098
<212> TYPE: DNA
<213> ORGANISM: Artificial Sequence
<220> FEATURE:
<223> OTHER INFORMATION: Plasmid AV15

<400> SEQUENCE: 34

```
ctggggcgcc ctctggtaag gttgggaagc cctgcaaagt aaactggatg ccaggcatca       60
aataaaacga aaggctcagt cgaaagactg ggcctttcgt tttatctgtt gtttgtcggt      120
gaacgctctc gcactaggac ttgccgcgga tactgcccca ttacatgaat tgcagcctca      180
gggacgtcag tagatcatgg aggtagggca tatgtcctct gttgttaaaa tgtgagttct      240
caacgaagca cgaatcggtc agaacctaca ctaaggagat tggtaggtg cacggtttct       300 gtcgcatagaa ccagttcatt tcagatgtct ggcacgtaag aggttccaac tttcaccata     360
atgaaataag atcactaccg ggcgtatttt ttgagttatc gagattttca ggagctaagg      420
aagctaaaat gattgaacaa gatggattgc acgcaggttc tccggccgct tgggtggaga      480
```

```
ggctattcgg ctatgactgg gcacaacaga caatcggctg ctctgatgcc gccgtgttcc    540
ggctgtcagc gcaggggcgc ccggttctttt ttgtcaagac cgacctgtcc ggtgccctga    600
atgaactcca agacgaggca gcgcggctat cgtggctggc cacgacgggc gttccttgcg    660
cagctgtgct cgacgttgtc actgaagcgg gaagggactg gctgctattg ggcgaagtgc    720
cggggcagga tctcctgtca tctcaccttg ctcctgccga gaaagtatcc atcatggctg    780
atgcaatgcg gcggctgcat acgcttgatc cggctacctg cccattcgac caccaagcga    840
aacatcgcat cgagcgagca cgtactcgga tggaagccgg tcttgtcgat caggatgatc    900
tggacgaaga gcatcagggg ctcgcgccag ccgaactgtt cgccaggctc aaggcgcgga    960
tgcccgacgg cgaggatctc gtcgtgaccc atggcgatgc ctgcttgccg aatatcatgg   1020
tggaaaatgg ccgcttttct ggattcatcg actgtggccg gctgggtgtg gcggaccgct   1080
atcaggacat agcgttggct acccgtgata ttgctgaaga gcttggcggc gaatgggctg   1140
accgcttcct cgtgctttac ggtatcgccg ctcccgattc gcagcgcatc gccttctatc   1200
gccttcttga cgagttcttc tgatgatgaa tggcaaggcg gcgcgtagcc ccccaaccga   1260
agttgagggg atttttttgga ctatgagcac gtccgcgagg gcgtcccgga aaacgattcc   1320
gaagcccaac ctttcataga aggcggcggt ggaatcgaaa tctcgtgatg gcaggttggg   1380
cgtcgcttgg tcggtcattt cgctcggtac ccatcggcat tttcttttgc gttttatttt   1440
gttaactgtt aattgtcctt gttcaaggat gctgtctttg acaacagatg ttttcttgcc   1500
tttgatgttc agcaggaagc tcggcgcaaa cgttgattgt tgtctgcgt agaatcctct    1560 gtttgtcata tagcttgtaa tcacgacatt gttccttc gcttgaggta cagcgaagtg   1620
tgagtaagta aaggttacat cgttaggatc aagatccatt tttaacacaa ggccagtttt   1680
gttcagcggc ttgtatgggc cagttaaaga attagaaaca taaccaagca tgtaaatatc   1740
gttagacgta atgccgtcaa tcgtcatttt tgatccgcgg gagtcagtga acaggtacca   1800
tttgccgttc attttaaaga cgttcgcgcg ttcaatttca tctgttactg tgttagatgc   1860
aatcagcggt ttcatcactt ttttcagtgt gtaatcatcg tttagctcaa tcataccgag   1920
agcgccgttt gctaactcag ccgtgcgttt tttatcgctt tgcagaagtt tttgactttc   1980
ttgacggaag aatgatgtgc ttttgccata gtatgctttg ttaaataaag attcttcgcc   2040
ttggtagcca tcttcagttc cagtgtttgc ttcaaatact aagtatttgt ggcctttatc   2100
ttctacgtag tgaggatctc tcagcgtatg gttgtcgcct gagctgtagt tgccttcatc   2160
gatgaactgc tgtacatttt gatacgtttt tccgtcaccg tcaaagattg atttataatc   2220
ctctacaccg ttgatgttca aagagctgtc tgatgctgat acgttaactt gtgcagttgt   2280
cagtgtttgt ttgccgtaat gtttaccgga gaaatcagtg tagaataaac ggattttttcc   2340 gtcagatgta aatgtggctg aacctgacca ttcttgtgtt tggtctttta ggatagaatc   2400
atttgcatcg aatttgtcgc tgtctttaaa gacgcggcca gcgtttttcc agctgtcaat   2460
agaagtttcg ccgacttttt gatagaacat gtaaatcgat gtgtcatccg cattttttagg   2520 atctccggct aatgcaaaga cgatgtggta gccgtgatag tttgcgacag tgccgtcagc   2580
gttttgtaat ggccagctgt cccaaacgtc caggcctttt gcagaagaga tatttttaat   2640
tgtggacgaa tcaaattcag aaacttgata tttttcattt ttttgctgtt cagggatttg   2700
cagcatatca tggcgtgtaa tatgggaaat gccgtatgtt tccttatatg gcttttggtt   2760
cgtttctttc gcaaacgctt gagttgcgcc tcctgccagc agtgcggtag taaaggttaa   2820
tactgttgct tgttttgcaa acttttttgat gttcatactc ttccttttttc aatattattg   2880
```

```
aagcatttat cagggttatt gtctcatgag cggatacata tttgaatgta tttagaaaaa    2940
taaacaaata ggggttccgc gcacatttcc ccgaaaagtg ccacctgacg tctaagaaac    3000
cattattatc atgacattaa cctataaaaa taggcgtatc acgaggccct tcgtcttca     3060 agaattctca tgtttgacag cttatcatcg ataagcttta atgcggtagt ttatcacagt    3120
taaattgcta acgcagtcag gcaccgtgta tgtcgcatct tgcagaatta gtagcttcag    3180
cgaaggccgc gatttctcag gcgagtgacg tcgcagcact ggataatgta cgtgttgagt    3240
acctgggaaa gaagggacac cttactcttc aaatgacaac cctgcgcgaa ctgccgccgg    3300
aggaacgccc cgcagcagga gcggtaatca atgaggcaaa ggagcaagta caacaggcac    3360
tgaacgcccg taaggctgag ttggaatccg ccgcattaaa cgcgcgcctt gctgcggaaa    3420
ccattgatgt ctcgctgccc gggcgccgca ttgagaatgg aggcttacac ccagtgactc    3480
gtaccatcga ccgtatcgaa tctttctttg gcgaacttgg cttcactgtg caactggac     3540 cggagattga ggacgactac cacaatttcg atgccttgaa cattcccggt catcatcctg    3600
cacgcgccga tcatgataca ttctggtttg ataccacccg tttgcttcgt acccagacaa    3660
gcggtgtcca aatccgtacg atgaaggctc agcaaccacc gatccgtatc attgctccag    3720
ggcgcgtgta ccgtaacgat tatgaccaga cacatacacc gatgtttcac caaatggaag    3780
ggttgattgt ggatacgaat atctctttca cgaatctgaa gggcaccttta catgatttct    3840 tacgcaactt tttcgaggag gaccttcaaa ttcgctttcg tccatcgtac ttcccttttg    3900
cagaaccttc ggctgaagtg gatgtaatgg ggaaaaacgg taagtggctg gaggttttag    3960
gttgcgggat ggttcatcca aatgtgcttc gcaacgtcgg catcgacccc gaagtctaca    4020
gtggattcgg attcgggatg ggaatggaac gtctgactat gcttcgttac ggcgtaacgg    4080
atttgcgctc ctttttgag aacgatcttc gttttctgaa gcaattcaaa taagcatttt    4140
tagtacgtgc aataaccact ctggttttc cagggtggtt ttttgatgcc cttttggag     4200 tcttcaactg agcctcgccc taggaactta agagcctcgc agagcaggat tcccgttgag    4260
caccgccagg tgcgaataag ggacagtgaa gaaggaacac ccgctcgcgg gtgggcctac    4320
ttcacctatc ctgcccggct gacgccgttg gatacaccaa ggaaagtcta cacgaaccct    4380
ttggcaaaat cctgtatatc gtgcgaaaaa ggatggatat accgaaaaaa tcgctataat    4440
gaccccgaag cagggttatg cagcggaaaa gcggtccttt tcatcacgtg ctataaaaat    4500
aattataatt taaattttt aatataaata tataaattaa aaatagaaag taaaaaaga     4560 aattaaagaa aaaatagttt ttgttttccg aagatgtaaa agactctagg gggatcgcca    4620
acaaatacta ccttttatct tgctcttcct gctctcaggt attaatgccg aattgtttca    4680
tcttgtctgt gtagaagacc acacacgaaa atcctgtgat tttacatttt acttatcgtt    4740
aatcgaatgt atatctattt aatctgcttt tcttgtctaa taaatatata tgtaaagtac    4800 gcttttttgtt gaattttttt aaacctttgt ttattttttt tttcttcatt ccgtaactct    4860
tctaccttct ttatttactt tctaaaatcc aaatacaaaa cataaaaata aataaacaca    4920
gagtaaattc ccaaattatt ccatcattaa aagatacgag gcgcgtgtaa gttacaggca    4980
agcgatccgc gcgtttcggt gatgacggtg aaaacctctg acacatgcag ctcccggaga    5040
cggtcacagc ttgtctgtaa gcggatgccg ggagcagaca agcccgtcag ggcgcgtcag    5100
cgggtgttgg cgggtgtcgg ggctggctta actatgcggc atcagagcag attgtactga    5160
gagtgcacca taccacagcc ggaagaggag tagggaatat tactggctga aaataagtct    5220
```

| | | | | | |
|---|---|---|---|---|---|
| tgaatgaacg | tatacgcgta | tatttctacc | aatctctcaa | cactgagtaa | tggtagttat | 5280 |
| aagaaagaga | ccgagttagg | gacagttaga | ggcggtggag | atattcctta | tggcatgtct | 5340 |
| ggcgatgata | aaacttttca | aacggcagcc | ccgatctaaa | agagctgaca | gggaaatggt | 5400 |
| cagaaaaaga | aacgtgcacc | cgcccgtctg | gacgcgccgc | tcacccgcac | ggcagagacc | 5460 |
| aatcagtaaa | aatcaacggt | taacgacatt | actatatata | taatatagga | agcatttaat | 5520 |
| agaacagcat | cgtaatatat | gtgtactttg | cagttatgac | gccagatggc | agtagtggaa | 5580 |
| gatattcttt | attgaaaaat | agcttgtcac | cttacgtaca | atcttgatcc | ggagcttttc | 5640 |
| ttttttttgcc | gattaagaat | tcggtcgaaa | aagaaaagg | agagggccaa | gagggagggc | 5700 |
| attggtgact | attgagcacg | tgagtatacg | tgattaagca | cacaaaggca | gcttggagta | 5760 |
| tgtctgttat | taatttcaca | ggtagttctg | gtccattggt | gaaagtttgc | ggcttgcaga | 5820 |
| gcacagaggc | cgcagaatgt | gctctagatt | ccgatgctga | cttgctgggt | attatatgtg | 5880 |
| tgcccaatag | aaagaaaca | attgacccgg | ttattgcaag | gaaaatttca | agtcttgtaa | 5940 |
| aagcatataa | aaatagttca | ggcactccga | atacttggt | tggcgtgttt | cgtaatcaac | 6000 |
| ctaaggagga | tgttttggct | ctggtcaatg | attacggcat | tgatatcgtc | caactgcatg | 6060 |
| gagatgagtc | gtggcaagaa | taccaagagt | tcctcggttt | gccagttatt | aaaagactcg | 6120 |
| tatttccaaa | agactgcaac | atactactca | gtgcagcttc | acagaaacct | cattcgttta | 6180 |
| ttcccttgtt | tgattcagaa | gcaggtggga | caggtgaact | tttggattgg | aactcgattt | 6240 |
| ctgactgggt | tggaaggcaa | gagagccccg | aaagcttaca | ttttatgtta | gctggtggac | 6300 |
| tgacgccaga | aaatgttggt | gatgcgctta | gattaaatgg | cgttattggt | gttgatgtaa | 6360 |
| gcggaggtgt | ggagacaaat | ggtgtaaaag | actctaacaa | aatagcaaat | ttcgtcaaaa | 6420 |
| atgctaagaa | ataggttatt | actgagtagt | atttatttaa | gtattgtttg | tgcacttgcc | 6480 |
| tgcaggcctt | ttgaaaagca | agcataaaag | atctaaacat | aaaatctgta | aataacaag | 6540 |
| atgtaaagat | aatgctaaat | catttggctt | tttgattgat | tgtacaggcc | ctggcttgtt | 6600 |
| gtccacaacc | gttaaacctt | aaaagcttta | aaagcttat | atattctttt | ttttcttata | 6660 |
| aaacttaaaa | ccttagaggc | tatttaagtt | gctgatttat | attaatttta | ttgttcaaac | 6720 |
| atgagagctt | agtacgtgaa | acatgagagc | ttagtacgtt | agccatgagg | gtttagttcg | 6780 |
| ttagccatga | gggtttagtt | cgttaaacat | gagagcttag | tacgttaaac | atgagagctt | 6840 |
| agtacgtgaa | acatgagagc | ttagtacgta | ctatcaacag | gttgaactgc | tgatcttcta | 6900 |
| ttcacacgca | atcaacaggc | aggataatcg | ctggtaaggt | cagtgctttc | ttcaggtagt | 6960 |
| agagatacaa | tagttcccaa | cgataggtgg | cagatttcac | tttacagacc | gactggttca | 7020 |
| gaagcgtaga | taatagcccg | tgttttccaa | taagggatag | tgtaggtaag | tcaactcctc | 7080 |
| cgtcagagcc | aaccgttt | | | | | 7098 |

<210> SEQ ID NO 35
<211> LENGTH: 7162
<212> TYPE: DNA
<213> ORGANISM: Artificial Sequence
<220> FEATURE:
<223> OTHER INFORMATION: Plasmid AV18

<400> SEQUENCE: 35

| | | | | | |
|---|---|---|---|---|---|
| ctggggcgcc | ctctggtaag | gttgggaagc | cctgcaaagt | aaactggatg | ccaggcatca | 60 |
| aataaaacga | aggctcagt | cgaaagactg | ggcctttcgt | tttatctgtt | gtttgtcggt | 120 |
| gaacgctctc | tactagagtc | acactggctc | accttcgggt | gggcctttct | gcgtttatag | 180 |

```
cactaggact tgccgcggat actgccccat tacatgaatt gcagcctcag ggacgtcagt      240
agatcatgga ggtagggcat atgtcctctg ttgttaaaat gtgagttctc aacgaagcac      300
gaatcggtca gaacctacac taaggagatt tggtaggtgc acggtttctg tcgcatagac      360
cagttcattt cagatgtctg gcacgtaaga ggttccaact ttcaccataa tgaaataaga      420
tcactaccgg gcgtattttt tgagttatcg agattttcag gagctaagga agctaaaatg      480
attgaacaag atggattgca cgcaggttct ccggccgctt gggtggagag gctattcggc      540
tatgactggg cacaacagac aatcggctgc tctgatgccg ccgtgttccg gctgtcagcg      600
caggggcgcc cggttctttt tgtcaagacc gacctgtccg gtgccctgaa tgaactccaa      660
gacgaggcag cgcggctatc gtggctggcc acgacgggcg ttccttgcgc agctgtgctc      720
gacgttgtca ctgaagcggg aagggactgg ctgctattgg gcgaagtgcc ggggcaggat      780
ctcctgtcat ctcaccttgc tcctgccgag aaagtatcca tcatggctga tgcaatgcgg      840
cggctgcata cgcttgatcc ggctacctgc ccattcgacc accaagcgaa acatcgcatc      900
gagcgagcac gtactcggat ggaagccggt cttgtcgatc aggatgatct ggacgaagag      960
catcaggggc tcgcgccagc cgaactgttc gccaggctca aggcgcggat gcccgacggc     1020
gaggatctcg tcgtgaccca tggcgatgcc tgcttgccga atatcatggt ggaaaatggc     1080
cgcttttctg gattcatcga ctgtggccgg ctgggtgtgg cggaccgcta tcaggacata     1140
gcgttggcta cccgtgatat tgctgaagag cttggcggcg aatgggctga ccgcttcctc     1200
gtgctttacg gtatcgccgc tcccgattcg cagcgcatcg ccttctatcg ccttcttgac     1260
gagttcttct gatgatgaat ggcaaggcgg cgcgtagccc cccaaccgaa gttgagggga     1320 ttttttttgac aattaatcat ccggctcgta atttatgtgg atcttaatca tgctaaggag     1380
gttttctaat gatgaacatc aaaaagtttg caaaacaagc aacagtatta acctttacta     1440
ccgcactgct ggcaggaggc gcaactcaag cgtttgcgaa agaaacgaac caaaagccat     1500
ataaggaaac atacggcatt tcccatatta cacgccatga tatgctgcaa atccctgaac     1560
agcaaaaaaa tgaaaaatat caagtttctg aatttgattc gtccacaatt aaaaatatct     1620
cttctgcaaa aggcctggac gtttgggaca gctggccatt acaaaacgct gacggcactg     1680 tcgcaaaacta tcacggctac cacatcgtct ttgcattagc cggagatcct aaaaatgcgg     1740 atgcacatc gatttacatg ttctatcaaa aagtcggcga aacttctatt gacagctgga     1800
aaaacgctgg ccgcgtcttt aaagacagcg acaaattcga tgcaaatgat tctatcctaa     1860
aagaccaaac acaagaatgg tcaggttcag ccacatttac atctgacgga aaaatccgtt     1920
tattctacac tgatttctcc ggtaaacatt acggcaaaca aacactgaca actgcacaag     1980
ttaacgtatc agcatcagac agctctttga acatcaacgg tgtagaggat tataaatcaa     2040
tctttgacgg tgacggaaaa acgtatcaaa atgtacagca gttcatcgat gaaggcaact     2100
acagctcagg cgacaaccat acgctgagag atcctcacta cgtagaagat aaaggccaca     2160
aatacttagt atttgaagca aacactggaa ctgaagatgg ctaccaaggc gaagaatctt     2220
tatttaacaa agcatactat ggcaaaagca catcattctt ccgtcaagaa agtcaaaaac     2280
ttctgcaaag cgataaaaaa cgcacggctg agttagcaaa cggcgctctc ggtatgattg     2340
agctaaacga tgattacaca ctgaaaaaag tgatgaaacc gctgattgca tctaacacag     2400
taacagatga aattgaacgc gcgaacgtct ttaaaatgaa cggcaaatgg tacctgttca     2460
ctgactcccg cggatcaaaa atgacgattg acggcattac gtctaacgat atttacatgc     2520
```

```
ttggttatgt ttctaattct ttaactggcc catacaagcc gctgaacaaa actggccttg    2580
tgttaaaaat ggatcttgat cctaacgatg taacctttac ttactcacac ttcgctgtac    2640
ctcaagcgaa aggaaacaat gtcgtgatta caagctatat gacaaacaga ggattctacg    2700
cagacaaaca atcaacgttt gcgccgagct tcctgctgaa catcaaaggc aagaaaacat    2760
ctgttgtcaa agacagcatc cttgaacaag gacaattaac agttaacaaa taaaaacgca    2820
aaagaaaatg ccgatgggta ccgagcgaaa tgaccgacca agcgacgccc aacctgccat    2880
cacgagattt cgattccacc gccgccttct atgaaaggtt gggcttcgga atcgttttcc    2940
gggacgccct cgcggacgtg ctcatagtcc aggcggtgtt gacataaata ccactggcgg    3000
tgatactgag cacatcagca ggtcacacag gaaagtacta gatgtcgcat cttgcagaat    3060
tagtagcttc agcgaaggcc gcgatttctc aggcgagtga cgtcgcagca ctggataatg    3120
tacgtgttga gtacctggga agaagggac accttactct tcaaatgaca accctgcgcg    3180
aactgccgcc ggaggaacgc cccgcagcag gagcggtaat caatgaggca aaggagcaag    3240
tacaacaggc actgaacgcc cgtaaggctg agttggaatc cgccgcatta aacgcgcgcc    3300
ttgctgcgga aaccattgat gtctcgctgc ccgggcgccg cattgagaat ggaggcttac    3360
acccagtgac tcgtaccatc gaccgtatcg aatcttctt tggcgaactt ggcttcactg    3420
tggcaactgg accggagatt gaggacgact accacaattt cgatgccttg aacattcccg    3480
gtcatcatcc tgcacgcgcc gatcatgata cattctggtt tgataccacc cgtttgcttc    3540
gtacccagac aagcggtgtc caaatccgta cgatgaaggc tcagcaacca ccgatccgta    3600
tcattgctcc agggcgcgtg taccgtaacg attatgacca gacacataca ccgatgtttc    3660
accaaatgga agggttgatt gtggatacga atatctcttt cacgaatctg aagggcacct    3720
tacatgattt cttacgcaac ttttcgagg aggaccttca aattcgcttt cgtccatcgt    3780
acttcccttt tgcagaacct tcggctgaag tggatgtaat ggggaaaaac ggtaagtggc    3840
tggaggtttt aggttgcggg atggttcatc caaatgtgct tcgcaacgtc ggcatcgacc    3900
ccgaagtcta cagtggattc ggattcggga tgggaatgga acgtctgact atgcttcgtt    3960
acggcgtaac ggatttgcgc tcctttttg agaacgatct tcgttttctg aagcaattca    4020 ataagcatt tttagtacgt gcaataacca ctctggtttt tccagggtgg ttttttgatg    4080
ccctttttgg agtcttcaac tgagcctcgc agagcaggat tcccgttgag caccgccagg    4140
tgcgaataag ggacagtgaa gaaggaacac ccgctcgcgg gtgggcctac ttcacctatc    4200
ctgcccggct gacgccgttg gatacaccaa ggaaagtcta cacgaaccct ttggcaaaat    4260
cctgtatatc gtgcgaaaaa ggatggatat accgaaaaaa tcgctataat gaccccgaag    4320
cagggttatg cagcggaaaa gctcccgaa aagtgccacc tgggtccttt tcatcacgtg    4380
ctataaaaat aattataatt taaatttttt aatataaata tataaattaa aaatagaaag    4440
taaaaaaaga aattaaagaa aaaatagttt ttgttttccg aagatgtaaa agactctagg    4500
gggatcgcca acaaatacta cctttttatct tgctcttcct gctctcaggt attaatgccg    4560
aattgtttca tcttgtctgt gtagaagacc acacacgaaa atcctgtgat tttacatttt    4620
acttatcgtt aatcgaatgt atatctattt aatctgcttt tcttgtctaa taatatata    4680 tgtaaagtac gcttttttgtt gaaattttt aaacctttgt ttatttttt tttcttcatt    4740 ccgtaactct tctaccttct ttatttactt tctaaaatcc aaatacaaaa cataaaaata    4800
aataaacaca gagtaaattc ccaaattatt ccatcattaa aagatacgag gcgcgtgtaa    4860
gttacaggca agcgatccgt ctaagaaacc attattatca tgacattaac ctataaaaat    4920
```

```
aggcgtatca cgaggcccTT TCGTCTCGCG CGTTTCGGTG ATGACGGTGA AAACCTCTGA    4980
cacatgcagc tcccggagac ggtcacagct tgtctgtaag cggatgccgg gagcagacaa    5040
gcccgtcagg gcgcgtcagc gggtgttggc gggtgtcggg gctggcttaa ctatgcggca    5100
tcagagcaga ttgtactgag agtgcaccat accacagccg gaagaggagt agggaatatt    5160
actggctgaa ataagtctt gaatgaacgt atacgcgtat atttctacca atctctcaac    5220
actgagtaat ggtagttata agaaagagac cgagttaggg acagttagag gcggtggaga    5280
tattccttat ggcatgtctg gcgatgataa aacttttcaa acggcagccc cgatctaaaa    5340
gagctgacag ggaaatggtc agaaaaagaa acgtgcaccc gcccgtctgg acgcgccgct    5400
cacccgcacg gcagagacca atcagtaaaa atcaacggtt aacgacatta ctatatatat    5460
aatataggaa gcatttaata gaacagcatc gtaatatatg tgtactttgc agttatgacg    5520
ccagatggca gtagtggaag atattcttta ttgaaaaata gcttgtcacc ttacgtacaa    5580
tcttgatccg gagcttttct ttttttgccg attaagaatt cggtcgaaaa agaaaaagga    5640
gagggccaag agggagggca ttggtgacta ttgagcacgt gagtatacgt gattaagcac    5700
acaaaggcag cttggagtat gtctgttatt aatttcacag gtagttctgg tccattggtg    5760
aaagtttgcg gcttgcagag cacagaggcc gcagaatgtg ctctagattc cgatgctgac    5820
ttgctgggta ttatatgtgt gcccaataga aagagaacaa ttgacccggt tattgcaagg    5880
aaaatttcaa gtcttgtaaa agcatataaa aatagttcag gcactccgaa atacttggtt    5940
ggcgtgtttc gtaatcaacc taaggaggat gttttggctc tggtcaatga ttacggcatt    6000
gatatcgtcc aactgcatgg agatgagtcg tggcaagaat accaagagtt cctcggtttg    6060
ccagttatta aaagactcgt atttccaaaa gactgcaaca tactactcag tgcagcttca    6120
cagaaacctc attcgtttat tcccttgttt gattcagaag caggtgggac aggtgaactt    6180
ttggattgga actcgatttc tgactgggtt ggaaggcaag agagcccga aagcttacat     6240 tttatgttag ctggtggact gacgccagaa aatgttggtg atgcgcttag attaaatggc    6300
gttattggtg ttgatgtaag cggaggtgtg gagacaaatg gtgtaaaaga ctctaacaaa    6360
atagcaaatt tcgtcaaaaa tgctaagaaa taggttatta ctgagtagta tttatttaag    6420
tattgtttgt gcacttgcct gcaggccttt tgaaaagcaa gcataaaaga tctaaacata    6480
aaatctgtaa aataacaaga tgtaaagata atgctaaatc atttggcttt ttgattgatt    6540
gtacaggccc tggcttgttg tccacaaccg ttaaaccTTA aaagctttaa aagccttata    6600
tattcttttt tttcttataa aacttaaaac cttagaggct atttaagttg ctgatttata    6660
ttaattttat tgttcaaaca tgagagctta gtacgtgaaa catgagagct tagtacgtta    6720
gccatgaggt tttagttcgt tagccatgag ggtttagttc gttaaacatg agagcttagt    6780
acgttaaaca tgagagctta gtacgtgaaa catgagagct tagtacgtac tatcaacagg    6840
ttgaactgct gatcttcggc atcaaataaa acgaaaggct cagtcgaaag actgggcctt    6900
tcgttttatc tgttgtttgt cggtgaacgc tctcctgagt aggacaaatc cgccgcccta    6960
gatattcaca cgcaatcaac aggcaggata atcgctggta aggtcagtgc tttcttcagg    7020
tagtagagat acaatagttc ccaacgatag gtggcagatt tcactttaca gaccgactgg    7080
ttcagaagcg tagataatag cccgtgtttt ccaataaggg atagtgtagg taagtcaact    7140
cctccgtcag agccaaccgt tt                                            7162
```

<210> SEQ ID NO 36

<211> LENGTH: 2157
<212> TYPE: DNA
<213> ORGANISM: Artificial Sequence
<220> FEATURE:
<223> OTHER INFORMATION: RhtC upstream homology arm-PxapR-rhtC-downstream homology arm

<400> SEQUENCE: 36

| | | | | | |
|---|---|---|---|---|---|
| attccagcgc | gatgacctgc | aaattgtggt | ggcgacggtg | gcgttcggca | tgggcatcaa | 60 |
| taaaccaaac | gttcgcttcg | tggtccactt | tgatattccg | cgcaatatcg | aatcctatta | 120 |
| tcaggaaacc | ggacgcgccg | ggcgtgatgg | cctgcccgcg | gaagcgatgc | tgttttacga | 180 |
| tccggctgat | atggcgtggc | tgcgccgttg | tctggaagag | aagccgcagg | gcagttgca | 240 |
| ggatatcgag | cgccacaaac | tcaatgcgat | gggcgcgttt | gccgaagcgc | aaacttgccg | 300 |
| tcgtctggta | ttgctgaact | attttggcga | agggcgtcag | gagccgtgcg | ggaactgcga | 360 |
| tatctgcctc | gatccgccga | aacagtacga | cggttcaacc | gatgctcaga | ttgccctttc | 420 |
| caccattggt | cgtgtgaatc | agcggtttgg | gatgggttat | gtggtggaag | tgattcgtgg | 480 |
| tgctaataac | cagcgtatcc | gcgactatgg | tcatgacaaa | ctgaaagtct | atggcatggg | 540 |
| ccgtgataaa | agccatgaac | attgggtgag | cgtgatccgc | cagctgattc | acctcggcct | 600 |
| ggtgacgcaa | aatattgccc | agcattctgc | cctacaactg | acagaggccg | cgcgcccggt | 660 |
| gctgcgcggc | gaatcctctt | tgcaacttgc | cgtgccgcgt | atcgtggcgc | tcaaaccgaa | 720 |
| agcgatgcag | aaatcgttcg | gcggcaacta | tgatcgcaaa | ctgttcgcca | aattacgcaa | 780 |
| actgcgtaaa | tcgatagccg | atgaaagtaa | tgtcccgccg | tacgtggtgt | taacgacgc | 840 |
| aaccttgatt | gagatggctg | aacagatgcc | gatcaccgcc | agcgaaatgc | tcagcgttaa | 900 |
| cggcgttggg | atgcgcaagc | tggaacgctt | tggcaaaccg | tttatggcgc | tgattcgtgc | 960 |
| gcatgttgat | ggcgatgacg | aagagtagtc | agcagcataa | aaaagtgcca | gtatgaagac | 1020 |
| tccgtaaacg | tttcccccgc | gagtcaaatg | tatgtcggat | atctggtggt | gaaatacttt | 1080 |
| atgccatgat | aatttaatac | gatgtattta | ttatatggag | cacttaatta | tgttgatgtt | 1140 |
| atttctcacc | gtcgccatgg | tgcacattgt | ggcgcttatg | agcccggtc | ccgatttctt | 1200 |
| ttttgtctct | cagaccgctg | tcagtcgttc | ccgtaaagaa | gcgatgatgg | gcgtgctggg | 1260 |
| cattacctgc | ggcgtaatgg | tttgggctgg | gattgcgctg | cttggcctgc | atttgattat | 1320 |
| cgaaaaatg | gcctggctgc | atacgctgat | tatggtgggc | ggtggcctgt | atctctgctg | 1380 |
| gatgggttac | cagatgctac | gtggtgcact | gaaaaaagag | gcggtttctg | cacctgcgcc | 1440 |
| acaggtcgag | ctggcgaaaa | gtgggcgcag | tttcctgaaa | ggtttactga | ccaatctcgc | 1500 |
| taatccgaaa | gcgattatct | actttggctc | ggtgttctca | ttgtttgtcg | gtgataacgt | 1560 |
| tggcactacc | gcgcgctggg | gcatttttgc | gctgatcatt | gtcgaaacgc | tggcgtggtt | 1620 |
| taccgtcgtt | gccagcctgt | ttgccctgcc | gcaaatgcgc | cgtggttatc | aacgtctggc | 1680 |
| gaagtggatt | gatggttttg | ccggggcgtt | atttgccgga | tttggcattc | atttgattat | 1740 |
| ttcgcggtga | tgccagacgc | gtcttcagag | taagtcggat | aaggcgttta | cgccgcatcc | 1800 |
| gacattattt | ttcacgcatg | cctcgccgat | gctaacagcg | ctcccaccag | cataaacaac | 1860 |
| gagccgaaaa | tcttattcag | cgccttcatc | tgctttggtc | ctttaatcca | tagagcaatc | 1920 |
| cgttgagcaa | gggtggcgta | accgatcatc | acaataatat | cgaccacaat | agtggtgacg | 1980 |
| ccgagcacga | tatactgcat | cagttgcggc | tgttgcggca | tgatgaattg | cggaaatagc | 2040 |
| gccgccagaa | acacaatact | tttgggattg | gtgagattca | caaaaactgc | gcgctggaac | 2100 | aaatgtcgac gcgattgagt agaggccagc gatttaaggt caattgcacc agcggcg    2157

<210> SEQ ID NO 37
<211> LENGTH: 78
<212> TYPE: DNA
<213> ORGANISM: Artificial Sequence
<220> FEATURE:
<223> OTHER INFORMATION: PxapR promoter_E.coli

<400> SEQUENCE: 37
atgtcggata tctggtggtg aaatacttta tgccatgata atttaatacg atgtatttat    60
tatatggagc acttaatt    78

<210> SEQ ID NO 38
<211> LENGTH: 699
<212> TYPE: DNA
<213> ORGANISM: Artificial Sequence
<220> FEATURE:
<223> OTHER INFORMATION: PxapR-rhtC

<400> SEQUENCE: 38
atgtcggata tctggtggtg aaatacttta tgccatgata atttaatacg atgtatttat    60
tatatggagc acttaattat gttgatgtta tttctcaccg tcgccatggt gcacattgtg    120
gcgcttatga gccccggtcc cgatttcttt tttgtctctc agaccgctgt cagtcgttcc    180
cgtaaagaag cgatgatggg cgtgctgggc attacctgcg gcgtaatggt ttgggctggg    240
attgcgctgc ttggcctgca tttgattatc gaaaaaatgg cctggctgca tacgctgatt    300
atggtgggcg gtggcctgta tctctgctgg atgggttacc agatgctacg tggtgcactg    360
aaaaaagagg cggtttctgc acctgcgcca caggtcgagc tggcgaaaag tgggcgcagt    420
ttcctgaaag gtttactgac caatctcgct aatccgaaag cgattatcta ctttggctcg    480
gtgttctcat tgtttgtcgg tgataacgtt ggcactaccg cgcgctgggg catttttgcg    540
ctgatcattg tcgaaacgct ggcgtggttt accgtcgttg ccagcctgtt tgccctgccg    600
caaatgcgcc gtggttatca acgtctggcg aagtggattg atggttttgc cggggcgtta    660
tttgccggat ttggcattca tttgattatt tcgcggtga    699

<210> SEQ ID NO 39
<211> LENGTH: 42
<212> TYPE: DNA
<213> ORGANISM: Artificial Sequence
<220> FEATURE:
<223> OTHER INFORMATION: PxapR-rhtC (Rev_right_arm_pcr)

<400> SEQUENCE: 39
ccaaccttac cagagggcgc cccagttcca gcgcgatgac ct    42

<210> SEQ ID NO 40
<211> LENGTH: 68
<212> TYPE: DNA
<213> ORGANISM: Artificial Sequence
<220> FEATURE:
<223> OTHER INFORMATION: PxapR-rhtC (Fwd_right_arm_pcr)

<400> SEQUENCE: 40
tcgtattaaa ttatcatggc ataaagtatt tcaccaccag atatccgaca tacatttgac    60
tcgcgggg    68

<210> SEQ ID NO 41
<211> LENGTH: 40

```
<212> TYPE: DNA
<213> ORGANISM: Artificial Sequence
<220> FEATURE:
<223> OTHER INFORMATION: PxapR-rhtC (Fwd_left_arm_pcr)

<400> SEQUENCE: 41
actcctccgt cagagccaac cgtttcgccg ctggtgcaat                40

<210> SEQ ID NO 42
<211> LENGTH: 76
<212> TYPE: DNA
<213> ORGANISM: Artificial Sequence
<220> FEATURE:
<223> OTHER INFORMATION: PxapR-rhtC (rev_left_arm_pcr)

<400> SEQUENCE: 42
tttatgccat gataatttaa tacgatgtat ttattatatg gagcacttaa ttatgttgat    60
gttatttctc accgtc                                                   76

<210> SEQ ID NO 43
<211> LENGTH: 57
<212> TYPE: DNA
<213> ORGANISM: Artificial Sequence
<220> FEATURE:
<223> OTHER INFORMATION: T1-Pr_RBS-ilva (rev_right_arm_pcr)

<400> SEQUENCE: 43
gcagggcttc ccaaccttac cagagggcgc cccaggcctt tttcttccgg aatggtc       57

<210> SEQ ID NO 44
<211> LENGTH: 66
<212> TYPE: DNA
<213> ORGANISM: Artificial Sequence
<220> FEATURE:
<223> OTHER INFORMATION: T1-Pr_RBS-ilva (fwd_right_arm_pcr)

<400> SEQUENCE: 44
gggcgggccc tcttgctttt caatggttgc atgtactaag gaggttgtat ggctgactcg    60
caaccc                                                              66

<210> SEQ ID NO 45
<211> LENGTH: 75
<212> TYPE: DNA
<213> ORGANISM: Artificial Sequence
<220> FEATURE:
<223> OTHER INFORMATION: T1-Pr_RBS-ilva (rev_left_arm_pcr)

<400> SEQUENCE: 45
tacatgcaac cattgaaaag caagagggcc cgcccccgaa ggttcgggta ttaacccccc    60
agtttcgatt tatcg                                                    75

<210> SEQ ID NO 46
<211> LENGTH: 55
<212> TYPE: DNA
<213> ORGANISM: Artificial Sequence
<220> FEATURE:
<223> OTHER INFORMATION: T1-Pr_RBS-ilva (fwd_left_arm_pcr)

<400> SEQUENCE: 46
aggtaagtca actcctccgt cagagccaac cgtttcatga cgctggatat cgcga         55

<210> SEQ ID NO 47
<211> LENGTH: 51
<212> TYPE: DNA
```

```
<213> ORGANISM: Artificial Sequence
<220> FEATURE:
<223> OTHER INFORMATION: T1acsRBS-yafv (fwd_left_arm_pcr)

<400> SEQUENCE: 47
actcctccgt cagagccaac cgtttgaaac cactggcacg tggagaataa g         51

<210> SEQ ID NO 48
<211> LENGTH: 47
<212> TYPE: DNA
<213> ORGANISM: Artificial Sequence
<220> FEATURE:
<223> OTHER INFORMATION: T1acsRBS-yafv (rev_right_arm_pcr)

<400> SEQUENCE: 48
ccaaccttac cagagggcgc cccagctgca aaacttcccg aaccgcg              47

<210> SEQ ID NO 49
<211> LENGTH: 73
<212> TYPE: DNA
<213> ORGANISM: Artificial Sequence
<220> FEATURE:
<223> OTHER INFORMATION: T1acsRBS-yafv (rev_left_arm_pcr)

<400> SEQUENCE: 49
ggccctcttg cttttcaatt aacatcctac aaggagaaca aaagcgtgcc tggtttgaag   60
attacgcttt tgc                                                     73

<210> SEQ ID NO 50
<211> LENGTH: 87
<212> TYPE: DNA
<213> ORGANISM: Artificial Sequence
<220> FEATURE:
<223> OTHER INFORMATION: T1acsRBS-yafv (fwd_right_arm_pcr)

<400> SEQUENCE: 50
ggatgttaat tgaaaagcaa gagggcccgc ccccgaaggt tcggggctga tattggaaat   60
atctgatttg caaattatcg tgttatc                                      87

<210> SEQ ID NO 51
<211> LENGTH: 47
<212> TYPE: DNA
<213> ORGANISM: Artificial Sequence
<220> FEATURE:
<223> OTHER INFORMATION: Rbs5-rhtC (fwd_right_arm_pcr)

<400> SEQUENCE: 51
ttaacctcct tagtttattc aattacattt gactcgcggg ggaaacg               47

<210> SEQ ID NO 52
<211> LENGTH: 45
<212> TYPE: DNA
<213> ORGANISM: Artificial Sequence
<220> FEATURE:
<223> OTHER INFORMATION: Rbs5-rhtC (fwd_left_arm_pcr)

<400> SEQUENCE: 52
actcctccgt cagagccaac cgtttcgccg ctggtgcaat tgacc                 45

<210> SEQ ID NO 53
<211> LENGTH: 46
<212> TYPE: DNA
<213> ORGANISM: Artificial Sequence
<220> FEATURE:
<223> OTHER INFORMATION: Rbs5-rhtC (rvs_right_arm_pcr)
```

<400> SEQUENCE: 53
ccaaccttac cagagggcgc cccagattcc agcgcgatga cctgca                          46

<210> SEQ ID NO 54
<211> LENGTH: 78
<212> TYPE: DNA
<213> ORGANISM: Artificial Sequence
<220> FEATURE:
<223> OTHER INFORMATION: Rbs5-rhtC (rvs_left_arm_pcr)

<400> SEQUENCE: 54
cgtttccccc gcgagtcaaa tgtaattgaa taaactaagg aggttaaagt atgttgatgt           60
tatttctcac cgtcgcca                                                        78

<210> SEQ ID NO 55
<211> LENGTH: 51
<212> TYPE: DNA
<213> ORGANISM: Artificial Sequence
<220> FEATURE:
<223> OTHER INFORMATION: PfocA-Cgl_pyc (fwd_left_arm_pcr)

<400> SEQUENCE: 55
agtcaactcc tccgtcagag ccaaccgttt gtttatcgct ggatggcccg c                    51

<210> SEQ ID NO 56
<211> LENGTH: 71
<212> TYPE: DNA
<213> ORGANISM: Artificial Sequence
<220> FEATURE:
<223> OTHER INFORMATION: PfocA-Cgl_pyc (rvs_left_arm_pcr)

<400> SEQUENCE: 56
acgagatact aacaaagcat tatagatgag aaattgatat agatcatatc gagatctgcc           60
tttgccggat g                                                               71

<210> SEQ ID NO 57
<211> LENGTH: 72
<212> TYPE: DNA
<213> ORGANISM: Artificial Sequence
<220> FEATURE:
<223> OTHER INFORMATION: PfocA-Cgl_pyc (fwd_insert_pcr)

<400> SEQUENCE: 57
ctataatgct tgttagtat ctcgtcgccg acttaataaa gagagagtta gtatgtcgac            60
tcacacatct tc                                                              72

<210> SEQ ID NO 58
<211> LENGTH: 62
<212> TYPE: DNA
<213> ORGANISM: Artificial Sequence
<220> FEATURE:
<223> OTHER INFORMATION: PfocA-Cgl_pyc (rvs_insert_pcr)

<400> SEQUENCE: 58
aagcccgcac tgtcaggtgc gggctttttt ctgtgtttcc ttaggaaacg acgacgatca           60
ag                                                                         62

<210> SEQ ID NO 59
<211> LENGTH: 63
<212> TYPE: DNA
<213> ORGANISM: Artificial Sequence
<220> FEATURE:

```
<223> OTHER INFORMATION: PfocA-Cgl_pyc (fwd_right_arm_pcr)

<400> SEQUENCE: 59
agcccgcacc tgacagtgcg ggctttttt ttcgaccaaa ggagcgatag cgccggctta    60
gtc                                                                 63

<210> SEQ ID NO 60
<211> LENGTH: 47
<212> TYPE: DNA
<213> ORGANISM: Artificial Sequence
<220> FEATURE:
<223> OTHER INFORMATION: PfocA-Cgl_pyc (rev_right_arm_pct)

<400> SEQUENCE: 60
ccttaccaga gggcgccca ggtttcgtca atccggaagt ggccctg                  47
```

THREONINE PRODUCTION STRAIN HAVING ATTENUATED EXPRESSION OF THE YAFV GENE

BACKGROUND OF THE INVENTION

Threonine is one of the essential amino acids that must be supplied in the diet of most domesticated animals used for food production. Most commonly, threonine is sold directly as an animal feed supplement to domestic animal producers. The most efficient way to make threonine is by fermentation of dextrose or other carbohydrate by a threonine producing bacteria, most often by *E. coli*. Over the past 20 years or more, many efforts have been made to improve the threonine production properties of *E. coli* by genetic engineering techniques, initially directed to enhancing expression of enzymes directly involved in the threonine biosynthetic pathway, and later to modifying genes involved in other metabolic pathways or related to export of threonine from the cell.

U.S. Pat. No. 5,939,307 describes chromosomal integration of a genetic construct containing a copy of the entire *E. coli* threonine operon under control of a non-native promoter that overexpresses the biosynthetic genes in *E. coli*, resulting in a strain exemplified by one on deposit at the US. Department of Agriculture's national strains depository laboratory as NRRI. B-21953.

U.S. Pat. No. 8,101,386 describes random mutation and selection of strains carrying an overexpressed threonine operon to select strains with increased resistance to raffinate compounds present in fermentation media that inhibit strain growth.

U.S. Pat. No. 6,455,284, describes increased production of amino acids in *E. coli* by over expression of pyruvate carboxylase.

U.S. Pat. No. 6,919,190 describes expression of an exogenous phosphoenolpyruvate carboxylase gene that does not require acetyl CoA for activation and is desensitized to feedback inhibition by aspartic acid in *E. coli* and other bacteria for general improved of amino acid production.

U.S. Pat. No. 6,830,903 describes expression of a mutated *Corynebacterium glutamicum* phosphoglucose isomerase to increase NADPH levels in amino acid producing cells.

U.S. Pat. No. 7,300,777 describes introduction of a feedback resistant pyruvate carboxylase gene into bacteria that produce the aspartate based amino acids for improved production.

U.S. Pat. No. 7,723,097 describes *E. coli* strains for improved amino acid production in which an aspartate semialdehyde dehydrogenase gene is operably associated with at least one non-native promoter, non-native ribosome binding site, or both to overexpress the enzyme.

U.S. Pat. No. 8,187,842 describes microbial strains possessing improved properties for production of aspartate-derived amino acids that have altered expression of the aceBAK operon, the glcB gene, or both. Alteration of expression was accomplished through increased transcription, relief from native transcriptional control, and/or other means.

U.S. Pat. No. 9,394,346 describes an *E. coli* strain that has a non-native promoter increasing expression of the rhtC gene encoding a threonine transporter promoter or containing multiple copies of the gene for increased export of threonine or homoserine.

U.S. Pat. Pub. No. 20200248218 describes a recombinant *E. coli* in which the activity levels of threonine deaminase encoded by the ilvA gene is inactivated while simultaneously introducing a comma gene encoding citramalate synthase.

There remains still, a need in the art to use genetic engineering techniques to improve *E. coli* for the production of threonine and other amino acids.

SUMMARY OF THE INVENTION

Described herein are *E coli* strains useful for the production of threonine by fermentation, wherein the strain is engineered to have attenuated expression of at least one gene selected from the group consisting of the yafV and ilvA genes relative to a parent strain.

In certain embodiments the strain further includes an exogenous pyruvate carboxylase gene operably linked to a promoter to express pyruvate carboxylase in the strain. In some embodiments wherein the exogenous pyruvate carboxylase gene is from *Corynebacterium glutamicum* having an amino acid sequence according to SEQ ID NO: 2

In certain embodiments the *E. coli* strain is further engineered to overexpress a threonine exporter gene in the cell relative to a non-engineered threonine exporter gene. In some embodiments the overexpressed threonine exporter gene contains a non-native promoter operably linked to the gene. In exemplary embodiments the threonine exporter gene is an endogenous rhtC gene encoding a protein according to SEQ ID NO: 25. In specific exemplary embodiments the endogenous rhtC gene contains a non-native ribosome binding site that causes the overexpression of the gene. In one embodiment, the non-native ribosome binding site is according SEQ ID NO: 23.

In certain embodiments the ilvA gene has attenuated expression in the strain. In some embodiments the ilvA gene has a non-native ribosome binding site inserted upstream of the open reading frame of the gene. In some embodiments the ilvA gene includes a transcriptional terminator sequence inserted upstream of the translational start site of the gene. In exemplary embodiments the ilvA gene includes a transcriptional terminator sequence inserted upstream of the translational start site of the gene and a non-native ribosome binding site inserted upstream of the open reading frame of the gene In certain embodiments the yafV gene has attenuated expression in the strain. In some embodiments the yafV gene has a non-native ribosome binding site inserted upstream of the open reading frame of the gene. In some embodiments the yafV gene includes a transcriptional terminator sequence inserted upstream of the translational start site of the gene. In exemplary embodiments the yafV gene includes a transcriptional terminator sequence inserted upstream of the translational start site of the gene and a non-native ribosome binding site inserted upstream of the open reading frame of the gene.

In preferred embodiments, each of the ilvA gene and yafV gene have attenuated expression in the strain. In exemplary embodiments each of ilvA gene and the yafV gene has a non-native ribosome binding site inserted upstream of the open reading frame of the gene. In other embodiments each of the ilvA gene and the yafV genes have a transcriptional terminator sequence inserted upstream of the translational start site of the gene. In preferred embodiments each of the ilvA gene and the yafV genes have a transcriptional terminator sequence inserted upstream of the translational start site of the gene and a non-native ribosome binding site inserted upstream of the open reading frame of the gene.

In the most preferred embodiments each of an endogenous yafV gene and endogenous ilvA gene are engineered to have attenuated expression in the strain and the strain further includes (a) an exogenous pyruvate carboxylase gene operably linked to a promoter to express pyruvate carboxylase in the strain and; (b) a rhtC threonine exporter gene engineered to be overexpressed in the strain. In the most desirable embodiments, the rhtC threonine exporter gene is engineered to contain a non-native ribosome binding site that causes the overexpression in the strain.

In any of the forgoing embodiments, exemplary ribosome binding sites for attenuation of expression of yafV or ilvA include SEQ ID NO: 13 and SEQ ID NO: 32. An exemplary embodiment of a strong ribosome binding site is SEQ ID NO: 23 for overexpression of rthC. An exemplary embodiment of a transcriptional terminator for attenuating expression is SEQ ID NO: 12, which may be used alone, or in combination with a weak ribosome binding site such as exemplified by SEQ ID NO: 13 and SEQ ID NO: 31 An exemplary embodiment of a non-native promoter for overexpression is a SEQ ID NO: 37 and SEQ ID NO: 6.

In cases of the above, where only the ilvA gene is attenuated, the strain does not have an exogenous cimA gene encoding a citramalate synthase.

BRIEF DESCRIPTION OF THE DRAWINGS

FIG. 4 is a table showing primers used to target genetic construct elements to particular genetic sequences in the *E. coli* chromosome.

DETAILED DESCRIPTION OF THE INVENTION

Figure 1:
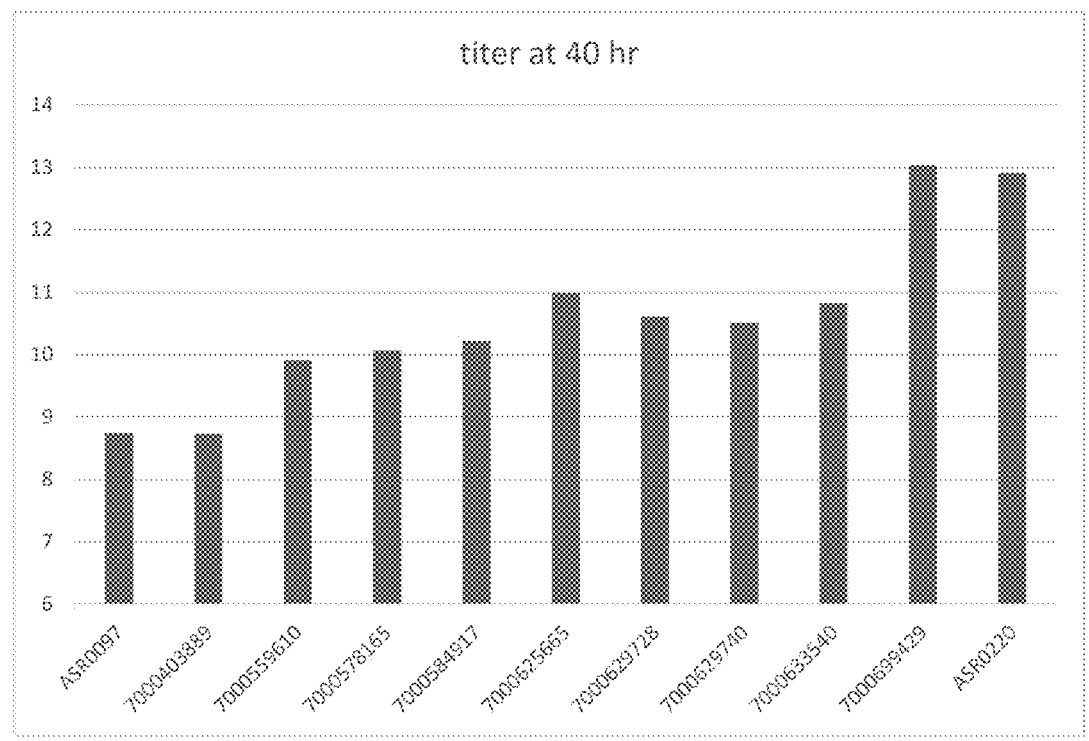
FIG. 1 is a bar graph showing stepwise improvement in threonine production for strains in the lineage of strains that contain attenuated expression of ivA and/or yafV genes as measured in microtiter dish assays.
Figure 2:
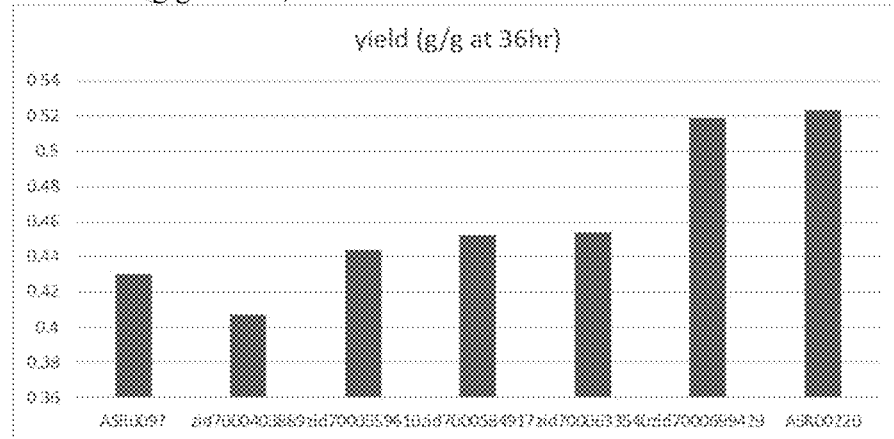
FIG. 2 are bar graphs showing stepwise improvement in threonine yield (A), productivity (B) or titer (C) for strains in the lineage of strains that contain attenuated expression of the ilvA and/or yafV genes as measured in 1 liter bench scale fermenters.
Figure 2:
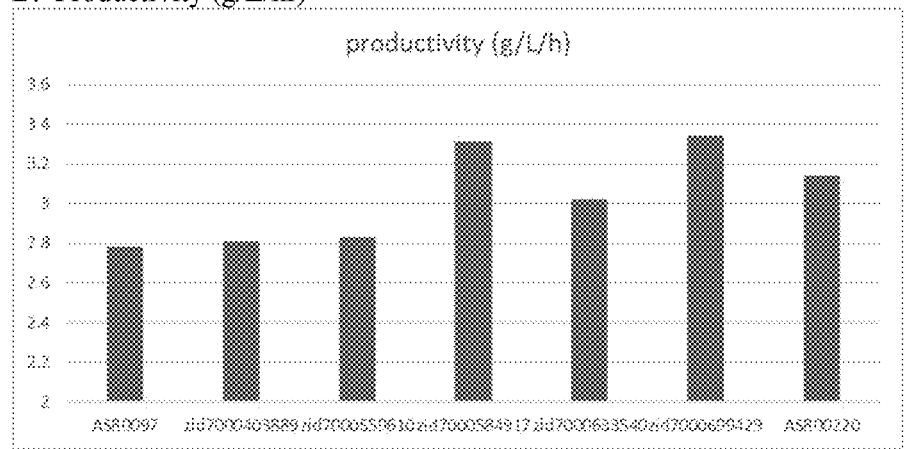
Figure 2:
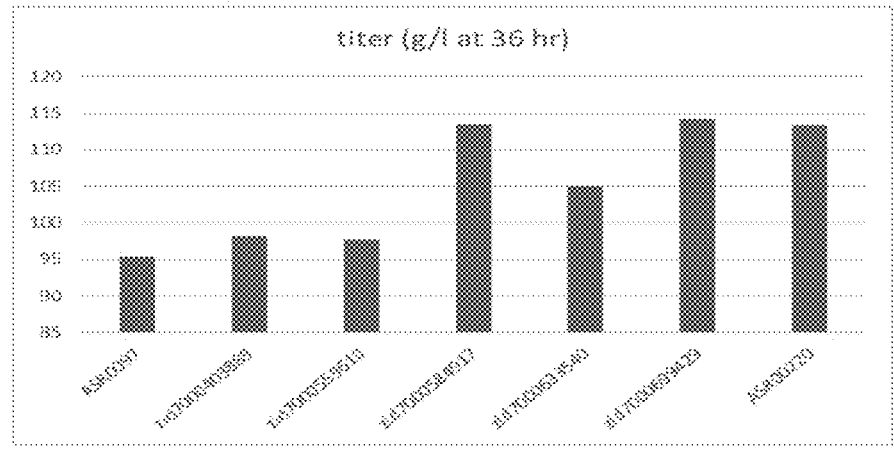
Figure 3A:
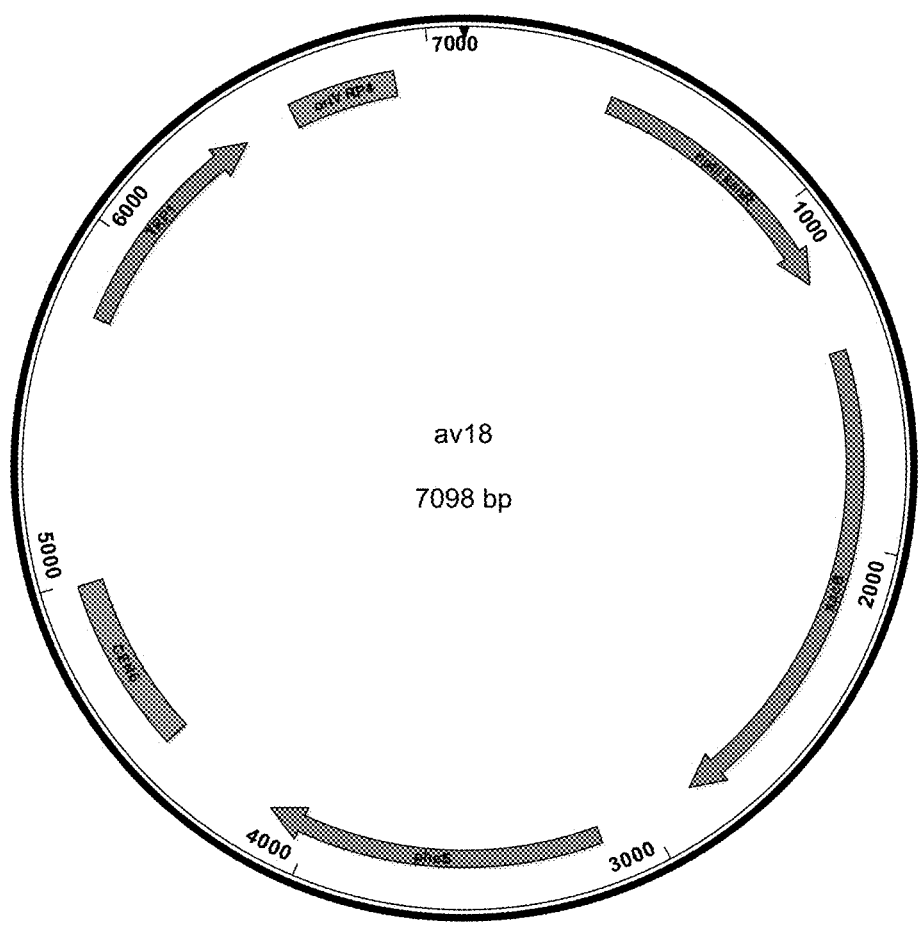
FIG. 3 shows a map of assembly vector plasmids av15 (A—SEQ ID NO: 34); and av18 (B—SEQ ID NO: 35) used to assemble transformation plasmids containing genetic elements used to engineer the strains of the present invention.
Figure 3B:
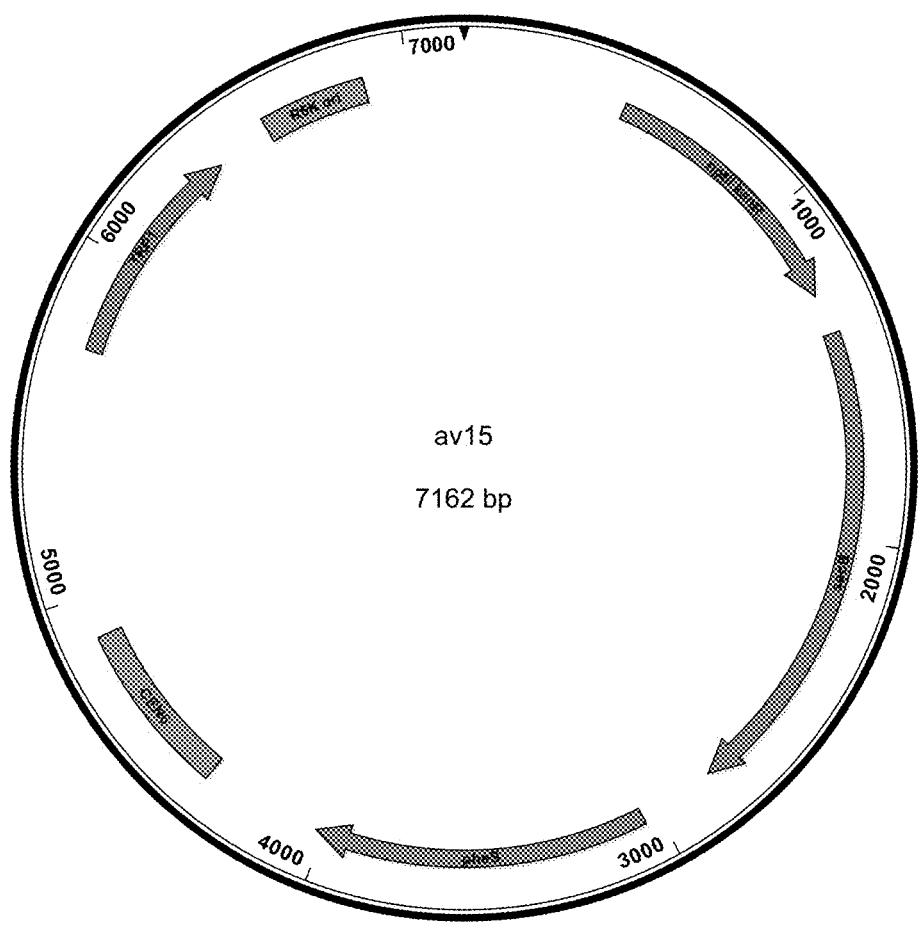

As used herein, the term "engineered" used with respect to a gene means the DNA sequence of some portion of the gene has been altered from its naturalor parental form by insertion, deletion, addition, or substitution of nucleic acids within the gene or introduction of complete substitute genes to accomplish an intended purpose.

As used herein, the term "attenuated" used with respect to expression of a gene in a strain means either (1) the level of expression of a protein encoded by thegene in the strain has been reduced relative to the expression level of the same gene in a parent or wild type strain where the gene has not been attenuated, but the expression level is not inactivated to zero so a detectable level of gene expression remains; or (2) there is a detectable level of enzymatic activity from a protein encoded by the gene that is less than the same enzymatic activity present in a parent or wild type strain having a gene that encodes the same enzymatic activity.

The first type of attenuation may be accomplished by several methods, including but not limited to (a) operably linking the gene to weaker promoter, meaning anon-native promoter that expresses mRNA encoded by gene at a lower level than the native or parent promoter, (b) operably linking the open reading frame of the gene to a weaker ribosome site, meaning the ribosome binding site on the mRNA encoded by gene is less efficient so the protein encoded by the open reading frame is produced at a lower level than from the native or parent ribosome binding site; (c) altering the start codon or other codons in the open reading frame of the gene so the codons are less efficiently utilized by the translational machinery of the strain carrying the gene; (d) in cases where a gene is in an operon or otherwise subject to having its mRNA expressed by read through transcription from a promoter upstream of the gene, introducing a transcriptional terminator sequence upstream of the gene to inhibit read through transcription; or (d) expressing an antisense RNA that would hybridize to mRNA expressed by the native or parent gene at a level lower than the total mRNA expressed from the native or parent gene thereby inhibiting translation of the mRNA.

The second type of attenuation includes the first type, but may further include substitution of the native or parent gene with a non-native or altered gene that encodes the same enzymatic activity, but where the substituted enzyme has reduced kinetic activity relative to the native or parent gene.

In the present case, it has been discovered that attenuation of the ilvA gene and attenuation of the yafV in an *E. coli* strain, each alone and in combination, results in increased threonine production in the strain. These are surprising discoveries given the prior art shows that inactivation of the ilvA leads to increased threonine production and yafV is predicted to encode an omega-amidase and decreasing the levels of this enzyme has no obvious advantage in increasing threonine production.

The ilvA gene encodes an enzyme alternatively called threonine dehydratase or threonine deaminase, which is involved in the synthesis of isoleucine and catalyzes the conversion of threonine to alpha-ketobutyrate. The *E. coli* ilvA gene is encoded by the nucleotide sequence according to SEQ ID NO:26, which encodes the protein according to SEQ ID NO:27. Because the activity degrades threonine, early threonine production strains included mutations that inactivated the ilvA gene, however it was discovered that such strains had poor growth properties. The present inventors began with a prior production strain that had a mutation that inactivated the ilvA gene.

This mutation was repaired to produce strain ASR0097, which has a wild type ilvA gene. To attenuate expression of the ilvA gene, a transcriptional terminator designated herein as TI having a nucleotide sequence according to SEQ ID NO: 12 linked to a weak ribosome binding site from the *E. coli* cro gene designated herein as croRBS having a nucleotide sequence according to SEQ ID NO: 32 was introduced upstream of the open reading frame of the ilvA gene to produce strain 7000403889 as described in more detail hereafter in Example 1. Table 5 below shows that engineered strain 7000403889 had increased productivity and titer of threonine production relative to parent strain ASR0097. It is noted herein that none of the strains have an exogenous cimA gene encoding a citramalate synthase to overcome the problems of reduced growth provided by the attenuated ilvA gene.

The inventors improved strain 7000403889 to further increase threonine production by introducing an exogenous pyruvate carboxylase gene (pyc) from *Corynebacterium glutamicum* designated herein as Cg.pyc. Cg.pyc. has the nucleotide sequence according to SEQ ID NO: 1 which encodes the protein according to SEQ ID NO: 2. To provide enhanced expression of pyruvate carboxylase in the strain, the Cg.pyc. gene was engineered under control of the strong promoter of the focA gene of E coli which the present inventors discovered is a strong constitutive promoter that has the nucleotide sequence according to SEQ ID NO: 6. The Cg pyc gene operably linked to the focA promoter was introduced into the aforementioned strain between the aslA and aslB genes of E coli to generate strain 7000559610, as described in more detail in Example 3. Table 5 below shows that engineered strain 7000559610 had significantly increased yield and measurably higher productivity relative to parent strain 7000403889.

Previous studies had shown that over expression of the rhtC gene in E. coli that encodes a threonine exporter protein by replacing the native promoter with a stronger promoter might enhance yield of or titer of threonine. The rhtC gene is according to SEQ ID NO: 17, which encodes the protein according to SEQ ID NO: 25. As a matter of philosophical inquiry only, the inventors sought to determine if replacing the rhtC promoter in a strain with attenuated ilvA expression and including the pyruvate carboxylase gene from Corynebacterium glutamicum would show an increase in threonine yield. As explained in more detail in Example, 4, the promoter for the E. coli xapR gene (SEQ ID NO: 37) was inserted upstream of the rhtC gene in strain 7000559610 to generate strain 7000584917. As shown in Table 5, strain 7000584917 had a significantly higher threonine titer than its parent strain 7000559610.

The yafV gene encodes an enzyme alternatively called omega-amidase or 2-oxoglutaramate amidase that hydrolyzes alpha-ketoglutaramate to form alpha-ketoglutarate and ammonia. The metabolic function of the gene is not known but is believed involved in generating substrates for metabolic repair. The E. coli yafV gene is encoded by the nucleotide sequence according to SEQ ID NO: 8 which encodes the protein according to SEQ ID NO: 16. The present inventors attenuated expression of the yafV gene present in E. coli by introducing the Tl terminator mentioned above linked to a different and weaker ribosome binding site, namely the ribosome binding site from the E. coli acs gene designated herein as acsRBS having a nucleotide sequence according to SEQ ID NO: 13 inserted upstream of the open reading fame of the yafV gene to produce a strain designated 7000699429 as described in more detail hereafter in Example 2. The parent of strain 7000699429 was a strain designated 7000633540, which was identical in all respects except for the attenuation of the yafV gene. Table 5 below shows that strain 7000699429 had significantly higher yield, productivity and titer in threonine production compared to the parent strain.

The inventors still further improved strain 7000584917 to increase threonine production by introducing the attenuated yafV gene into a derivative of strain 7000584917 having all other engineered elements of that strain mentioned above except also including a repaired leuL gene. Strain 7000584917 had a mutated leuL gene inherited from prior rounds of mutagenesis in one of the ancestor strains. The leuL mutation was repaired to the wild type sequence in strain 7000584917 resulting in strain 7000633540, which Table 5 below shows had a reduced yield, productivity and titer of threonine in comparison to parent strain 7000584917, however the growth rate of strain 7000633540 was better than parent strain 7000584917. The inventors further engineered strain 7000633540 to include attenuation of the yafV gene resulting in strain 7000699429. Table 5 below shows that strain 7000699429 had significantly higher yield, productivity and titer in threonine production compared to the parent strain 7000633540 and grandparent strain 7000584917.

The inventors further improved strain 7000559610 to increase threonine production without substituting the promoter in front of the rhtC gene by introducing a stronger ribosome binding site upstream of the rhtC gene. The strong ribosome binding site used was a consensus E. coli ribosome binding designated herein as RBS5, which is encoded by SEQ ID NO: 23. The inventors removed the xapR promoter and restored the original native promoter for the rhtC gene from strain 7000699429 and inserted RBS5 upstream of the open reading frame of the rhtC gene to generate strain ASR0220 as described in Example 5. Table 5 below shows that engineered strain ASR0220 performed nearly as well as strain 7000699429 with respect to yield, titer and productivity in threonine production.

The following examples describe how the foregoing changes were made to exemplify how one of ordinary skill in the art can make such changes in E. coli to practice the present invention. Each of the examples below involves the amplification of nucleic acid fragments that contained the functional elements of interest, (i.e., promoter, terminator, ribosome binding sites) flanked by primers that hybridized to defined target sequences with the DNA from the genome of a parent E. coli threonine production strain designated ASR0097 used as a template. All strains constructed herein derive from ARS0097 as a parent, grandparent, great grandparent, or great-great grandparent strain. The amplified fragments were assembled into transformation plasmids that were integrated into the strain at the site of the target gene of interest to replace the target gene with the engineered construct. To direct targeting of the gene into the chromosome by recombination, a number of primer sequences were created (e.g., SEQ ID NO: 39-60) that included sequences having homology to terminal portions of the gene target, which are shown in FIG. 4. The transformation plasmids were constructed from the fragments using the yeast assembly method described in Gene (1987) 58(2-3):201-216, which is incorporated herein by reference in its entirety, or by the Gibson assembly method described in Nature Methods (2009), 6:343-345, each of which is incorporated herein by reference in their entirety.

Example 1

Insertion of Tl Terminator and Cro RBS Upstream of ilvA

A nucleic acid sequence comprising terminator, Tl and the ribosomal binding site (RBS) from the cro gene SEQ ID NO: 31 was inserted upstream of the ilvA gene to lower expression of ilvA. Plasmid 13001394600 was constructed using yeast assembly of the following fragments: a downstream homology arm produced by PCR using primers Tl-pR_RBS-ilvA-rev_right_arm_pcr (5'-GCA GGG CTT CCC AAC CTT ACC AGA GGG CGC CCC AGG CCT TTT TCT TCC GGA ATG GTC) (SEQ ID NO: 43) and Tl-pR_RBS-ilvA-fwd_right_arm_pcr (5'-GGG CGG GCC CTC TTG CTT TTC AAT GGT TGC ATG TAC TAA GGA GGT TGT ATG GCT GAC TCG CAA CCC) (SEQ ID NO: 44) and genomic DNA from strain ASR0097 as template; an upstream homology arm produced by PCR using primers Tl-pR_RBS-ilvA-rev_left_arm_pcr (5'-TAC ATG CAA CCA TTG AAA AGC AAG AGG GCC CGC CCC CGA AGG TTC GG GTA TTA ACC CCC CAG TTT CGA TTT ATC G) (SEQ ID NO: 45) and Tl-pR_RBS-ilvA-fwd_left_arm_pcr (5'-AGG TAA GTC AAC TCC TCC GTC AGA GCC AAC CGT TTC ATG ACG CTG GAT ATC GCG A) (SEQ ID NO: 46) using genomic DNA from strain ASR0097 as template; and linearized plasmid av15 which carries the nptll gene conferring kanamycin resistance and the sacB gene conferring sensitivity to growth on sucrose. The resulting plasmid (13001394600) was integrated into the chromosome of strain ASR0097 by single crossover by electroporating the circular plasmid into the cell and selecting kanamycin resistance. The integrant was then grown on sucrose to select for the loss of the sacB gene and loss of the plasmid. Resulting strains were screened for the loss of kanamycin resistance. The loss of the plasmid and the insertion of the Tl terminator and cro RBS 5' of the ilvA was confirmed by PCR. A resulting strain, 7000403889 was selected for further work.

Example 2

Insertion of Tl-acsRBS-yafV

The expression level of yafV was lowered by the insertion of terminator Tl and the ribosomal binding site (RBS) from the acs gene of *E. coli*. Plasmid 13002350086 was constructed using Gibson assembly (Nat Meth (2009), 6:343-345) of the following fragments: a downstream homology arm produced by PCR using primers TlacsRBS-yafV_fwd_left_arm_pcr (5' ACT CCT CCG TCA GAG CCA ACC GTT TGA AAC CAC TGG CAC GTG GAG AAT AAG) (SEQ ID NO: 47) and TlacsRBS-yafV_rev_left_arm_pcr (5'-GGC CCT CTT GCT TTT CAA TTA ACA TCC TAC AAGGAG AAC AAA AGC GTG CCT GGT TTG AAG ATT ACG CTT TTG C) (SEQ ID NO: 48) and genomic DNA from strain ASR0097 as template; an upstream homology arm produced by PCR using primers TlacsRBS-yafV_fwd_right_arm_arm_pcr (5'-GGA TGT TAA TTG AAA AGC AAG AGG GCC CGC CCC CGA AGG TTC GGG GCT GAT ATT GGA AAT ATC TGA TTT GCA AAT TAT CGT GTT ATC) (SEQ ID NO: 49) and TlacsRBS-yafV_rev_right_arm_pcr (5'-CCA ACC TTA CCA GAG GGC GCC CCA GCT GCA AAA CTT CCC GAA CCG CG) (SEQ ID NO: 50) using genomic DNA from strain ASR0097 as template; and linearized plasmid AV18 which carries the nptll gene (conferring kanamycin resistance and the sacB gene conferring sensitivity to growth on sucrose. The resulting plasmid (13002350086) was integrated into the chromosome of strain 633540 by single crossover by electroporating the circular plasmid into the cell and selecting kanamycin resistance. The integrant was then grown on sucrose to select for the loss of the sacB gene and loss of the plasmid. Resulting strains were screened for the loss of kanamycin resistance. The loss of the plasmid and the insertion of Tl-acsRBS-yafV were confirmed by PCR. A resulting strain, 7000699429 was selected for further work.

Example 3

Insertion of PfocA-pycCg10689

A gene encoding pyruvate carboxylase of *Corynebacterium glutamicum* control by the promoter of the PfocA gene was introduced between the aslA and aslB genes of 559610. Plasmid 13003176716 was constructed using yeast assembly (Gene (1987) 58(2-3):201-216) of the following fragments: an upstream homology arm produced by PCR using primers PfocA-Cgl_pyc_fwd_left_arm_pcr (5'-AGT CAA CTC CTC CGT CAG AGC CAA CCG TTT GTT TAT CGC TGG ATG GCC CGC) (SEQ ID NO: 55) and PfocA-Cgl_pyc_rev_left_arm_pcr (5'-ACG AGA TAC TAA CAA AGC ATT ATA GAT GAG AAA TTG ATA TAG ATC ATA TCG AGA TCT GCC TTT GCC GGA TG) (SEQ ID NO: 56) and genomic DNA from strain ASR0097 as template; a downstream homology arm produced by PCR using primers PfocA-Cgl_pyc_fwd-_right_arm_pcr (5'-AGC CCG CAC CTG ACA GTG CGG GCT TTT TTT TTC GACCAA AGG AGC GAT AGC GCC GGC TTA GTC) (SEQ ID NO:59) and PfocA-Cgl_pyc_rev_right_arm_pcr (5'-CCT TAC CAG AGG GCG CCC CAG GTT TCG TCAATC CGG AAG TGG CCC TG) (SEQ ID NO: 60) using genomic DNA from strain ASR0097 as template; the pyc gene of *C. glutamicum* produced via PCR using primers PfocA-Cgl_pyc_fwd_insert_pcr (5'-CTA TAA TGC TTT GTT AGT ATC TCG TCG CCG ACT TAA TAA AGA GAG AGT TAG TAT GTC GAC TCA CAC ATC TTC) (SEQ ID NO: 57) and PfocA-Cgl_pyc_rev_insert_pcr (5'-AAG CCC GCA CTG TCAGGT GCG GGC TTT TTT CTG TGT TTC CTT AGG AAA CGA CGA CGA TCA AG (SEQ ID NO: 58) and a cloned *C. glutamicum* pyc gene as template; and linearized plasmid AV18 which carries the nptll gene conferring kanamycin resistance) and the sacB gene conferring sensitivity to growth on sucrose). The resulting plasmid (13003176716) was integrated into the chromosome of strain ASR0097 by single crossover by electroporating the circular plasmid into the cell and selecting kanamycin resistance. The integrant was then grown on sucrose to select for the loss of the sacB gene and loss of the plasmid. Resulting strains were screened for the loss of kanamycin resistance. The loss of the plasmid and the insertion of PfocA-pycCgl0689 between aslA and aslB was confirmed by PCR. A resulting strain, 7000584917 (was selected for further work.

Example 4

Insertion of Promoter PxapR—in Front of the rhtC Gene

The promoter from the *E. coli* xapR gene, was inserted upstream of rhtC to increase expression of the threonine exporter protein RhtC. Plasmid 13002916394 was constructed using Gibson assembly (Nat Meth (2009), 6:343-345) of the following fragments: a downstream homology arm produced by PCR using primers PxapR-rhtC_fwd_left_arm_pcr (5' ACT CCT CCG TCA GAG CCA ACC GTT TCG CCG CTG GTG CAA T) (SEQ ID NO: 41) and PxapR-rhtC_rev_left_arm_pcr (5'-TTT ATG CCA TGA TAA TTT AAT ACG ATG TAT TTA TTA TAT GGA GCA CTT AAT TAT GTT GAT GTT ATT TCT CAC CGT C) (SEQ ID NO: 42) and genomic DNA from strain ASR0097 as template; an upstream homology arm produced by PCR using primers PxapR-rhtC_fwd_right_arm_pcr (5'-TCG TAT TAA ATT ATC ATG GCA TAA AGT ATT TCA CCA CCA GAT ATC CGA CAT ACA TTT GAC TCG CGG GG) (SEQ ID NO: 40) and PxapR-rhtC_rev_right_arm_pcr (5' CCA ACC TTA CCA GAG GGC GCC CCA GTT CCA GCG CGA TGA CCT) (SEQ ID NO: 39) using genomic DNA from strain ASR0097 as template; and linearized plasmid AV18 (which carries the nptll gene conferring kanamycin resistance and the sacB gene (conferring sensitivity to growth on sucrose. The resulting plasmid (13002916394) was integrated into the chromosome of strain 7000403889 by single crossover by electroporating the circular plasmid into the cell and selecting kanamycin resistance. The integrant was then grown on sucrose to select for the loss of the sacB gene and loss of the plasmid. Resulting strains were screened for the loss of kanamycin resistance. The loss of the plasmid and the insertion of the xapR promoter 5' of the rhtC gene was confirmed by PCR. A resulting strain, 7000559610 was selected for further work.

Example 5

Insertion of rbs5-rhtC

A synthetic ribosomal binding site (RBS) based on the consensus *E. coli* RBS was inserted in upstream of the rhtC gene, replacing the PxapR-rhtC modification made earlier in the strain's development. Plasmid 13003172323 was constructed using yeast assembly (Gene (1987) 58(2-3):201-216) of the following fragments: an upstream homology arm produced by PCR using primers rbs5-rhtC_fwd_left_arm_pcr (5'-ACT CCT CCG TCA GAG CCA ACC GTT TCG CCG CTG GTG CAA TTG ACC) (SEQ ID NO:52) and rbs5-rhtCrev_left_arm_pcr (5'-CGT TTC CCC CGC GAG TCA AAT GTAATTGAA TAAACT AAGGAGGTT AAAGTA TGTTGA TGTTATTTCTCA CCG TCG CCA) (SEQ ID NO: 54) and genomic DNA from strain ASR0097 as template; an upstream homology arm produced by PCR using primers rbs5-rhtC_fwd_right_arm_pcr (5'-TTA ACC TCC TTA GTT TAT TCA ATT ACA TTT GAC TCG CGG GGG AAA CG) (SEQ ID NO: 51) andrbs5-rhtC_rev_left_arm_pcr (5'-CCA ACC TTA CCA GAG GGC GCC CCA GAT TCC AGC GCG ATG ACC TGC A) (SEQ ID NO:53) using genomic DNA from strain ASR0097 as template; and linearized plasmid AV15 which carries the nptII gene (conferring kanamycin resistance) and the sacB gene (conferring sensitivity to growth on sucrose). The resulting plasmid (13003172323) was integrated into the chromosome of strain 7000699429 by single crossover by electroporating the circular plasmid into the cell and selecting kanamycin-resistance. The integrant was then grown on sucrose to select for the loss of the sacB gene and loss of the plasmid. Resulting strains were screened for the loss of kanamycin resistance. The loss of the plasmid and the insertion of the T1 terminator and cro RBS 5' of the ilvA was confirmed by PCR. A resulting strain, ASR0220 (aka 757279; which was placed on deposit at the USDA strain depository as NRRL B-67978) was selected for further work.

Example 6

Measurement of Threonine Titer in Microtiter Plates

Strains were initially evaluated for threonine production by a two-stage cultivation process in microtiter plates. Cells were grown in Medium A and after 24 hours, a 3.3% inoculum was transferred to Medium B and grown for additional 40 h. Culture conditions were 37° C., 1000 rpm (Infors HT incubated shaker). Dextrose was measured by HPLC using a CarboSep CHO 87C FA column and RI detection. Threonine was measured by reverse phase ion pair UHPLC with 1-octanesulfonic acid as the ion pairing agent and a YMC Triart C18 column with detection by UV at 254 nm.

TABLE 1

Media components for plate screening:

| Component | Medium A (2/100 ml) | Medium B (2/100 ml) |
|---|---|---|
| Glucose | 5.23 | 4.29 |
| Ammonium | 0.07 | 0.20 |
| CSL | 0.38 | 0.55 |
| Fe | 5.9E−04 | 5.9E−04 |
| Mn | 7.3E−04 | 7.3E−04 |
| Mg | 0.02 | 0.03 |
| K | 0.07 | 0.07 |

TABLE 2

Average titers obtained in plate screening with various genetic modification(s) in each strain:

| Strain | titer at 40 hr | Modifications to ASR0097 |
|---|---|---|
| ASR0097 | 8.75 | — |
| 7000403889 | 8.74 | T1-PRRBS-ilvA |
| 7000559610 | 9.91 | T1-PRRBS-ilvA, PfocA-Cg_pyc |
| 7000578165 | 10.07 | PfocA-Cg_pyc |
| 7000584917 | 10.22 | T1-PRRBS-ilvA, PfocA-Cg_pyc, PxapR-rhtC |
| 7000625665 | 11.00 | leuL-wt |
| 7000629728 | 10.60 | rbs5-rhtC |
| 7000629740 | 10.51 | PxapR-rhtC |
| 7000633540 | 10.82 | T1-PRRBS-ilvA, PfocA-Cg_pyc, PxapR-rhtC, leuL-wt |
| 7000699429 | 13.04 | T1-PRRBS-ilvA, PfocA-Cg_pyc, PxapR-rhtC, leuL-wt, T1_acsRBS-yafV |
| ASR0220 | 12.91 | T1-PRRBS-ilvA, PfocA-Cg_pyc, leuL-wt, T1_acsRBS-yafV, rbs5-rhtC |

The results shown above are graphically depicted in FIG. 1.

Example 7

Measurement of Yield, Productivity and Titer in 1 Liter Fermentation Vessels Strains were tested in fed batch DAS-GIP fermenters with glucose fed on demand. The three-stage process used for cultivation and fermentation is as follows. 1 frozen vial of strain(s) to be tested is grown in 500 ml of medium Cina 2 L shake flask at 37° C. and 250 rpm for 9 hours. Shake flasks are then used to inoculate 1 L DAS-GIP vessels for the seed stage using medium D at an inoculation ratio of 0.03%. Vessels are run at 39° C. maintaining dissolved oxygen (DO) 2:20% by cascading agitation until a net OD of >18 is achieved. pH is maintained at 6.9 by addition of 21% aqueous ammonia. In the third stage 1 L DAS-GIP fermentation vessels containing medium E are inoculated from the seed vessel(s) at a ratio of 8.3% with a starting volume of 435 ml after inoculation. Vessels are run at 33° C. maintaining DO 2:20% by cascading agitation for 36 h. pH is maintained at 6.9 by on demand addition of 21% aqueous ammonia. Glucose at 58% wt/wt was fed on demand. Residual glucose was measured by HPLC using a CarboSep CHO 87C FA column and an RI detector. Threonine was measured by reverse phase ion pair UHPLC with 1-octanesulfonic acid as the ion pairing agent and a YMC Triart C18 column with detection by UV at 254 nm.

TABLE 3

Composition of media used for evaluation of strains by fermentation

| Component | Medium C (2'100 ml) | Medium D (2'100 ml) | Medium E (2'100 ml) |
| --- | --- | --- | --- |
| Glucose | 0.25 | 6.5 | 0.15 |
| (NH4)2SO4 | NIA | 0.10 | 0.05 |
| CSL | NIA | 1.2 | 1.0 |
| Yeast Extract (Tastone 900) | 3.5 | NIA | NIA |
| FeSO4*7H2O | NIA | 0.003 | 0.003 |
| MnSO4*H2O | NIA | 0.0021 | 0.0021 |
| MgSO4*7H2O | NIA | 0.10 | 0.15 |
| K2HPO4 | 0.25 | NIA | NIA |
| KH2PO4 | NIA | 0.125 | 0.25 |
| NaCl | 0.25 | NIA | NIA |
| Antifoam | NIA | 0.05 | 0.05 |

TABLE 4

Strains and genetic modifications found in strain:

| strain | modifications to ASR0097 |
| --- | --- |
| ASR0097 | — |
| 7000403889 | T1-PRRBS-ilvA |
| 7000559610 | T1-PRRBS-ilvA, PfocA-Cg_pyc |
| 7000584917 | T1-PRRBS-ilvA, PfocA-Cg_pyc, PxapR-rhtC |
| 7000633540 | T1-PRRBS-ilvA, PfocA-Cg_pyc, PxapR-rhtC, leuL-wt |
| 7000699429 | T1-PRRBS-ilvA, PfocA-Cg_pyc, PxapR-rhtC, leuL-wt, T1_acsRBS-yafV |
| ASR00220 | T1-PRRBS-ilvA, PfocA-Cg_pyc, leuL-wt, T1_acsRBS-yafV, rbs5-rhtC |

TABLE 5

Yield (g threonine/g dextrose consumed), productivity (g threonine/liter/hr), and titer (g threonine/liter) of strains as tested in DAS-GIP fermenters:

| strain | yield (g/g at 36 hr) | productivity (g/L/h) | titer (g/l at 36 hr) |
| --- | --- | --- | --- |
| ASR0097 | 0.43 | 2.78 | 95.3 |
| 7000403889 | 0.407 | 2.81 | 98.2 |
| 7000559610 | 0.444 | 2.83 | 97.7 |
| 7000584917 | 0.452 | 3.31 | 113.4 |
| 7000633540 | 0.454 | 3.02 | 105 |
| 7000699429 | 0.519 | 3.34 | 114.2 |
| ASR00220 | 0.523 | 3.14 | 113.3 |

The results shown above are graphically depicted in FIG. 1.

Amino acid and DNA sequences
1. pyc C. glutamicum_cg0791_DNA
(SEQ ID NO: 1)

ATGTCGACTCACACATCTTCAACGCTTCCAGCATTCAAAAAGA

TCTTGGTAGCAAACCGCGGCGAAATCGCGGTCCGTGCTTTCCGTGCA

GCACTCGAAACCGGTGCAGCCACGGTAGCTATTTACCCCCGTGAAGA

TCGGGGATCATTCCACCGCTCTTTTGCTTCTGAAGCTGTCCGCATTGG

TACTGAAGGCTCACCAGTCAAGGCGTACCTGGACATCGATGAAATTA

TCGGTGCAGCTAAAAAAGTTAAAGCAGATGCTATTTACCCGGGATAT

GGCTTCCTGTCTGAAAATGCCCAGCTTGCCCGCGAGTGCGCGGAAAA

CGGCATTACTTTTATTGGCCCAACCCCAGAGGTTCTTGATCTCACCGG

TGATAAGTCTCGTGCGGTAACCGCCGCGAAGAAGGCTGGTCTGCCAG

TTTTGGCGGAATCCACCCCGAGCAAAAACATCGATGACATCGTTAAA

AGCGCTGAAGGCCAGACTTACCCCATCTTTGTAAAGGCAGTTGCCGG

TGGTGGCGGACGCGGTATGCGCTTTGTTTCTTCACCTGATGAGCTCCG

CAAATTGGCAACAGAAGCATCTCGTGAAGCTGAAGCGGCATTCGGCG

ACGGTTCGGTATATGTCGAACGTGCTGTGATTAACCCCCAGCACATT

GAAGTGCAGATCCTTGGCGATCGCACTGGAGAAGTTGTACACCTTTA

TGAACGTGACTGCTCACTGCAGCGTCGTCACCAAAAAGTTGTCGAAA

TTGCGCCAGCACAGCATTTGGATCCAGAACTGCGTGATCGCATTTGT

GCGGATGCAGTAAAGTTCTGCCGCTCCATTGGTTACCAGGGCGCGGG

AACCGTGGAATTCTTGGTCGATGAAAAGGGCAACCACGTTTTCATCG

AAATGAACCCACGTATCCAGGTTGAGCACACCGTGACTGAAGAAGTC

ACCGAGGTGGACCTGGTGAAGGCGCAGATGCGCTTGGCTGCTGGTGC

AACCTTGAAGGAATTGGGTCTGACCCAAGATAAGATCAAGACCCACG

GTGCAGCACTGCAGTGCCGCATCACCACGGAAGATCCAAACAACGGC

TTCCGCCCAGATACCGGAACTATCACCGCGTACCGCTCACCAGGCGG

AGCTGGCGTTCGTCTTGACGGTGCAGCTCAGCTCGGTGGCGAAATCA

CCGCACACTTTGACTCCATGCTGGTGAAAATGACCTGCCGTGGTTCCG

ACTTTGAAACTGCTGTTGCTCGTGCACAGCGCGCGTTGGCTGAGTTCA

CCGTGTCTGGTGTTGCAACCAACATTGGTTTCTTGCGTGCGTTGCTGC

GGGAAGAGGACTTCACTTCCAAGCGCATCGCCACCGGATTTATCGGC

GATCACCCACACCTCCTTCAGGCTCCACCTGCGGATGATGAGCAGGG

ACGCATCCTGGATTACTTGGCAGATGTCACCGTGAACAAGCCTCATG

GTGTGCGTCCAAAGGATGTTGCAGCACCAATCGATAAGCTGCCCAAC

ATCAAGGATCTGCCACTGCCACGCGGTTCCCGTGACCGCCTGAAGCA

GCTTGGCCCAGCCGCGTTTGCTCGTGATCTCCGTGAGCAGGACGCAC

TGGCAGTTACTGATACCACCTTCCGCGATGCACACCAGTCTTTGCTTG

CGACCCGAGTCCGCTCATTCGCACTGAAGCCTGCGGCAGAGGCCGTC

GCAAAGCTGACTCCTGAGCTTTTGTCCGTGGAGGCCTGGGGCGGCGC

GACCTACGATGTGGCGATGCGTTTCCTCTTTGAGGATCCGTGGGACA

GGCTCGACGAGCTGCGCGAGGCGATGCCGAATGTAAACATTCAGATG

CTGCTTCGCGGCCGCAACACCGTGGGATACACCCCGTACCCAGACTC

CGTCTGCCGCGCGTTTGTTAAGGAAGCTGCCACCTCCGGCGTGGACA

TCTTCCGCATCTTCGACGCGCTTAACGACGTCTCCCAGATGCGTCCAG

CAATCGACGCAGTCCTGGAGACCAACACCGCGGTAGCCGAGGTGGCT

ATGGCTTATTCTGGTGATCTCTCTGATCCAAATGAAAAGCTCTACACC

CTGGATTACTACCTAAAGATGGCAGAGGAGATCGTCAAGTCTGGCGC

TCACATTCTGGCCATTAAGGATATGGCTGGTCTGCTTCGCCCAGCTGC

GGTAACCAAGCTGGTCACCGCACTGCGCCGTGAATTCGATCTGCCAG

TGCACGTGCACACCCACGACACTGCGGGTGGCCAGTTGGCTACCTAC

TTTGCTGCAGCTCAAGCTGGTGCAGATGCTGTTGACGGTGCTTCCGCA

-continued

```
CCACTGTCTGGCACCACCTCCCAGCCATCCCTGTCTGCCATTGTTGCT
GCATTCGCGCACACCCGTCGCGATACCGGTTTGAGCCTCGAGGCTGT
TTCTGACCTCGAGCCGTACTGGGAAGCTGTGCGCGGACTGTACCTGC
CATTTGAGTCTGGAACCCCAGGCCCAACCGGTCGCGTCTACCGCCAC
GAAATCCCAGGCGGACAGTTGTCCAACCTGCGTGCACAGGCCACCGC
ACTGGGCCTTGCTGATCGCTTCGAGCTCATCGAAGACAACTACGCAG
CCGTTAATGAGATGCTGGGACGCCCAACCAAGGTCACCCCATCCTCC
AAGGTTGTTGGCGACCTCGCACTCCACCTGGTTGGTGCGGGTGTAGA
TCCAGCAGACTTTGCTGCAGACCCACAAAAGTACGACATCCCAGACT
CTGTCATCGCGTTCCTGCGCGGCGAGCTTGGTAACCCTCCAGGTGGCT
GGCCAGAACCACTGCGCACCCGCGCACTGGAAGGCCGCTCCGAAGG
CAAGGCACCTCTGACGGAAGTTCCTGAGGAAGAGCAGGCGCACCTCG
ACGCTGATGATTCCAAGGAACGTCGCAACAGCCTCAACCGCCTGCTG
TTCCCGAAGCCAACCGAAGAGTTCCTCGAGCACCGTCGCCGCTTCGG
CAACACCTCTGCGCTGGATGATCGTGAATTCTTCTACGGACTGGTCGA
GGGCCGCGAGACTTTGATCCGCCTGCCAGATGTGCGCACCCCACTGC
TTGTTCGCCTGGATGCGATCTCTGAGCCAGACGATAAGGGTATGCGC
AATGTTGTGGCCAACGTCAACGGCCAGATCCGCCCAATGCGTGTGCG
TGACCGCTCCGTTGAGTCTGTCACCGCAACCGCAGAAAAGGCAGATT
CCTCCAACAAGGGCCATGTTGCTGCACCATTCGCTGGTGTTGTCACTG
TGACTGTTGCTGAAGGTGATGAGGTCAAGGCTGGAGATGCAGTCGCA
ATCATCGAGGCTATGAAGATGGAAGCAACAATCACTGCTTCTGTTGA
CGGCAAGATTGAACGCGTTGTGGTTCCTGCTGCAACGAAGGTGGAAG
GTGGCGACTTGATCGTCGTCGTTTCCTAA
```

2. Pyc C. glutamicum_cg0791 protein (SEQ ID NO: 2)

MSTHTSSTLPAFKKILVANRGEIAVRAFRAALETGAATVAIYPRE
DRGSFHRSFASEAVRIGTEGSPVKAYLDIDEIIGAAKKVKADAIYPGYGF
LSENAQLARECAENGITFIGPTPEVLDLTGDKSRAVTAAKKAGLPVLAES
TPSKNIDEIVKSAEGQTYPIFVKAVAGGGRGMRFVASPDELRKLATEAS
REAEAAFGDGAVYVERAVINPQHIEVQILGDHTGEVVHLYERDCSLQRR
HQKVVEIAPAQHLDPELRDRICADAVKFCRSIGYQGAGTVEFLVDEKGN
HVFIEMNPRIQVEHTVTEEVTEVDLVKAQMRLAAGATLKELGLTQDKIK
THGAALQCRITTEDPNNGFRPDTGTITAYRSPGGAGVRLDGAAQLGGEIT
AHFDSMLVKMTCRGSDFETAVARAQRALAEFTVSGVATNIGFLRALLRE
EDFTSKRIATGFIADHPHLLQAPPADDEQGRILDYLADVTVNKPHGVRPK
DVAAPIDKLPNIKDLPLPRGSRDRLKQLGPAAFARDLREQDALAVTDTTF
RDAHQSLLATRVRSFALKPAAEEAVAKLTPELLSVEAWGGATYDVAMRF
LFEDPWDRLDELREAMPNVNIQMLLRGRNTVGYTPYPDSVCRAFVKEA
ASSGVDIFRIFDALNDVSQMRPAIDAVLETNTAVAEVAMAYSGDLSDPN
EKLYTLDYYLKMAEEIVKSGAHILAIKDMAGLLRPAAVTKLVTALRREF

DLPVHVHTHDTAGGQLATYFAAAQAGADAVDGASAPLSGTTSQPSLSAI
VAAFAHTRRDTGLSLEAVSDLEPYWEAVRGLYLPFESGTPGPTGRVYRH
EIPGGQLSNLRAQATALGLADRFELIEDNYAAVNEMLGRPTKVTPSSKV
VGDLALHLVGAGVDPADFAADPQKYDIPDSVIAFLRGELGNPPGGWPEP
LRTRALEGRSEGKAPLTEVPEEEQAHLDADDSKERRNSLNRLLFPKPTEE
FLEHRRRFGNTSALDDREFFYGLVEGRETLIRLPDVRTPLLVRLDAISEPD
DKGMRNVVANVNGQIRPMRVRDRSVESVTATAEKADSSNKGHVAAPF
AGVVTVTVAEGDEVKAGDAVAIIEAMKMEATITASVDGKIDRVVVPAA
TKVEGGDLIVVVS 3. aslB upstream homology arm_DNA (SEQ ID NO: 3)

```
GTTTATCGCTGGATGGCCCGCCTGAGATCCACAATCAATATCGCGTG
ACTAAAGGTGGCAGACCCACGCATAAGCTGGTGATGCGTGCCCTGAC
GCTCCTGCAAAAACATCATGTCGACTATAACGTGCTGGTCTGCGTTA
ATCGCACCAGCGCGCAGCAACCGTTGCAGGTATATGATTTTTTGTGC
GATGCGGGAGTCGAATTCATCCAGTTTATTCCGGTGGTCGAGCGCCT
GGCTGATGAAACAACTGCCCGCGATGGACTTAAGTTACATGCGCCTG
GTGATATTCAGGGTGAGCTAACGGAATGGTCGGTGCGCCCCGAGGAG
TTCGGTGAGTTTCTGGTGGCGATATTCGACCACTGGATCAAACGCGA
CGTCGGCAAGATTTTCGTGATGAATATCGAATGGGCGTTTGCCAATTT
TGTCGGTGCGCCGGGTGCGGTTTGCCATCATCAGCCAACCTGTGGGC
GCTCGGTGATTGTTGAGCACAACGGCGACGTTTACGCCTGTGATCAC
TATGTTTATCCGCAATATCGGCTGGGGAATATGCACCAGCAAACAAT
TGCAGAAATGATCGATTCCCCGCAACAGCAGGCGTTTGGTGAAGATA
AATTTAAGCAGTTACCGGCGCAGTGTCGCAGTTGTAACGTGTTAAAA
GCGTGCTGGGGAGGCTGCCCGAAACACCGCTTCATGCTCGATGCCAG
CGGCAAACCGGGACTGAATTATTTGTGTGCCGGGTATCAGCGTTATTT
CCGCCATCTACCGCCATATCTTAAAGCAATGGCTGATTTGCTGGCGCA
CGGTCGCCCGGCCAGCGACATTATGCATGCGCATTTGCTGGTGGTGA
GTAAGTAGAAATCGGCGGCCGCCTGCGGTTGATTGCGGATGCGGCG
TAAACGCCTTATCCGGCCTACATGATCGTGCAAATTCAATAAATTGC
AGCGTTCTGTAGGCTGGATAAGATGCGTCAGCATCGCATCCGGCAAA
GGCAGATCTC
```

4. aslA downstream homology arm_DNA (SEQ ID NO: 4)

```
AGCGATAGCGCCGGCTTAGTCAGATTTAATCTGCGCGCGTGGTGGAT
ATTTTTTCAGGATCTCCATATACGCGTGCATTTCGGTCTGTAGCGGTA
CACCCATCGGAATATGGCGCACGCCGATGGAGTCGCTTTCCTGCGGA
TCGGTGTAGAGGTTAAACACCGACGATCCCGCCGTTTGCATTACTGT
GCCGGTGAATCCACCCTGATATCCGCTCTGGGTATAAGCGTAAGGTT
GCTGAATCAGGACGTGATACTTGAACTCATCCATACGCACAGCAGCG
AGTTTACCGTTGAGGAAGTAGTGCTCGGCCTTACGGTTAGACTGACC
ATTTGTTCCCAGGAAGAAGGATGTCTGGTCCACACCATCGATAAAGG
```

TGGTTTTCGGCACTAAATTCGCCACTTTCGCTCCAGGATGCCCTGCCA
GATCCAGCGCGGTAGGGAAGAGATCTGCCAGATCGACAATACCGTCA
GATTTACGCGGTTGGATCATCCCTTTCCAGTAAACGAAAGTCGGTAC
GCGAACGCCGCCTTCCCAGGTCGAACCTTTCGCACCACGGAACGGGG
TGCGTCCGTGCGGCGGTACTTCGGCTTCCGGTCCGTTATCGGAGGTAA
AGACGATCAGCGTGTTATCAAGCTGACCGTTTTTCTCCAGTGTTTTAT
ACAGATTAGCGAACACATCGTTCATCTCCACCATGCAGTCGCCATAC
GAGGTGCGTGCCGGAGAGCTACCCGCATATTTCGCATTTGGGTAGTT
ATCGAAGTGGCAGCCACGAGTGCCGTAGTAGAGGAAGAATGGTTTAT
CGCTCTTCGCCATCTTGTCGAGGAACTTAACGCCATAGTCCATCCAGC
GTTGATCCAGATCTTCCATATATTTCGGCGTAATGTCGGCAATGGCCT
GTTGTTCGCCGCCGCGCACCGCATGAACGTCATCTTTGCTGAACGGTA
ATTGCTTGATGTATTCAGAACGGTCCGGACTCAGGGCCACTTCCGGA
TTGACG 5. aslB upstream homology arm-PfocA promoter-
pyc-aslA downstream homology arm_DNA
(SEQ ID NO: 5)
GTTTATCGCTGGATGGCCCGCCTGAGATCCACAATCAATATCGCGTG
ACTAAAGGTGGCAGACCCACGCATAAGCTGGTGATGCGTGCCCTGAC
GCTCCTGCAAAAACATCATGTCGACTATAACGTGCTGGTCTGCGTTA
ATCGCACCAGCGCGCAGCAACCGTTGCAGGTATATGATTTTTTGTGC
GATGCGGGAGTCGAATTCATCCAGTTTATTCCGGTGGTCGAGCGCCT
GGCTGATGAAACAACTGCCCGCGATGGACTTAAGTTACATGCGCCTG
GTGATATTCAGGGTGAGCTAACGGAATGGTCGGTGCGCCCCGAGGAG
TTCGGTGAGTTTCTGGTGGCGATATTCGACCACTGGATCAAACGCGA
CGTCGGCAAGATTTTCGTGATGAATATCGAATGGGCGTTTGCCAATTT
TGTCGGTGCGCCGGGTGCGGTTTGCCATCATCAGCCAACCTGTGGGC
GCTCGGTGATTGTTGAGCACAACGGCGACGTTTACGCCTGTGATCAC
TATGTTTATCCGCAATATCGGCTGGGGAATATGCACCAGCAAACAAT
TGCAGAAATGATCGATTCCCCGCAACAGCAGGCGTTTGGTGAAGATA
AATTTAAGCAGTTACCGGCGCAGTGTCGCAGTTGTAACGTGTTAAAA
GCGTGCTGGGGAGGCTGCCCGAAACACCGCTTCATGCTCGATGCCAG
CGGCAAACCGGGACTGAATTATTTGTGTGCCGGGTATCAGCGTTATTT
CCGCCATCTACCGCCATATCTTAAAGCAATGGCTGATTTGCTGGCGCA
CGGTCGCCCGGCCAGCGACATTATGCATGCGCATTTGCTGGTGGTGA
GTAAGTAGAAATCGGCGGCCGCCTGCGGTTGATTGCCGGATGCGGCG
TAAACGCCTTATCCGGCCTACATGATCGTGCAAATTCAATAAATTGC
AGCGTTCTGTAGGCTGGATAAGATGCGTCAGCATCGCATCCGGCAAA
GGCAGATCTCGATATGATCTATATCAATTTCTCATCTATAATGCTTTG
TTAGTATCTCGTCGCCGACTTAATAAAGAGAGAGTTAGTATGTCGAC
TCACACATCTTCAACGCTTCCAGCATTCAAAAAGATCTTGGTAGCAA
ACCGCGGCGAAATCGCGGTCCGTGCTTTCCGTGCAGCACTCGAAACC
GGTGCAGCCACGGTAGCTATTTACCCCCGTGAAGATCGGGGATCATT
CCACCGCTCTTTTGCTTCTGAAGCTGTCCGCATTGGTACTGAAGGCTC
ACCAGTCAAGGCGTACCTGGACATCGATGAAATTATCGGTGCAGCTA
AAAAAGTTAAAGCAGATGCTATTTACCCGGGATATGGCTTCCTGTCT
GAAAATGCCCAGCTTGCCCGCGAGTGCGCGGAAAACGGCATTACTTT
TATTGGCCCAACCCCAGAGGTTCTTGATCTCACCGGTGATAAGTCTCG
TGCGGTAACCGCCGCGAAGAAGGCTGGTCTGCCAGTTTTGGCGGAAT
CCACCCCGAGCAAAAACATCGATGACATCGTTAAAAGCGCTGAAGGC
CAGACTTACCCCATCTTTGTAAAGGCAGTTGCCGGTGGTGGCGGACG
CGGTATGCGCTTTGTTTCTTCACCTGATGAGCTCCGCAAATTGGCAAC
AGAAGCATCTCGTGAAGCTGAAGCGGCATTCGGCGACGGTTCGGTAT
ATGTCGAACGTGCTGTGATTAACCCCCAGCACATTGAAGTGCAGATC
CTTGGCGATCGCACTGGAGAAGTTGTACACCTTTATGAACGTGACTG
CTCACTGCAGCGTCGTCACCAAAAAGTTGTCGAAATTGCGCCAGCAC
AGCATTTGGATCCAGAACTGCGTGATCGCATTTGTGCGGATGCAGTA
AAGTTCTGCCGCTCCATTGGTTACCAGGGCGCGGGAACCGTGGAATT
CTTGGTCGATGAAAAGGGCAACCACGTTTTCATCGAAATGAACCCAC
GTATCCAGGTTGAGCACACCGTGACTGAAGAAGTCACCGAGGTGGAC
CTGGTGAAGGCGCAGATGCGCTTGGCTGCTGGTGCAACCTTGAAGGA
ATTGGGTCTGACCCAAGATAAGATCAAGACCCACGGTGCAGCACTGC
AGTGCCGCATCACCACGGAAGATCCAAACAACGGCTTCCGCCCAGAT
ACCGGAACTATCACCGCGTACCGCTCACCAGGCGGGAGCTGGCGTTCG
TCTTGACGGTGCAGCTCAGCTCGGTGGCGAAATCACCGCACACTTTG
ACTCCATGCTGGTGAAAATGACCTGCCGTGGTTCCGACTTTGAAACT
GCTGTTGCTCGTGCACAGCGCGCGTTGGCTGAGTTCACCGTGTCTGGT
GTTGCAACCACATTGGTTTCTTGCGTGCGTTGCTGCGGGAAGAGGA
CTTCACTTCCAAGCGCATCGCCACCGGATTTATCGGCGATCACCCACA
CCTCCTTCAGGCTCCACCTGCGGATGATGAGCAGGGACGCATCCTGG
ATTACTTGGCAGATGTCACCGTGAACAAGCCTCATGGTGTGCGTCCA
AAGGATGTTGCAGCACCAATCGATAAGCTGCCCAACATCAAGGATCT
GCCACTGCCACGCGGTTCCCGTGACCGCCTGAAGCAGCTTGGCCCAG
CCGCGTTTGCTCGTGATCTCCGTGAGCAGGACGCACTGGCAGTTACT
GATACCACCTTCCGCGATGCACACCAGTCTTTGCTTGCGACCCGAGTC
CGCTCATTCGCACTGAAGCCTGCGGCAGAGGCCGTCGCAAAGCTGAC
TCCTGAGCTTTTGTCCGTGGAGGCCTGGGCGGCGCGACCTACGATG
TGGCGATGCGTTTCCTCTTTGAGGATCCGTGGGACAGGCTCGACGAG
CTGCGCGAGGCGATGCCGAATGTAAACATTCAGATGCTGCTTCGCGG
CCGCAACACCGTGGGATACACCCCGTACCCAGACTCCGTCTGCCGCG
CGTTTGTTAAGGAAGCTGCCACCTCCGGCGTGGACATCTTCCGCATCT
TCGACGCGCTTAACGACGTCTCCCAGATGCGTCCAGCAATCGACGCA

```
GTCCTGGAGACCAACACCGCGGTAGCCGAGGTGGCTATGGCTTATTC
TGGTGATCTCTCTGATCCAAATGAAAAGCTCTACACCCTGGATTACTA
CCTAAAGATGGCAGAGGAGATCGTCAAGTCTGGCGCTCACATTCTGG
CCATTAAGGATATGGCTGGTCTGCTTCGCCCAGCTGCGGTAACCAAG
CTGGTCACCGCACTGCGCCGTGAATTCGATCTGCCAGTGCACGTGCA
CACCCACGACACTGCGGGTGGCCAGTTGGCTACCTACTTTGCTGCAG
CTCAAGCTGGTGCAGATGCTGTTGACGGTGCTTCCGCACCACTGTCTG
GCACCACCTCCCAGCCATCCCTGTCTGCCATTGTTGCTGCATTCGCGC
ACACCCGTCGCGATACCGGTTTGAGCCTCGAGGCTGTTTCTGACCTCG
AGCCGTACTGGGAAGCTGTGCGCGACTGTACCTGCCATTTGAGTCT
GGAACCCCAGGCCCAACCGGTCGCGTCTACCGCCACGAAATCCCAGG
CGGACAGTTGTCCAACCTGCGTGCACAGGCCACCGCACTGGGCCTTG
CTGATCGCTTCGAGCTCATCGAAGACAACTACGCAGCCGTTAATGAG
ATGCTGGGACGCCCAACCAAGGTCACCCCATCCTCCAAGGTTGTTGG
CGACCTCGCACTCCACCTGGTTGGTGCGGGTGTAGATCCAGCAGACT
TTGCTGCAGACCCACAAAAGTACGACATCCCAGACTCTGTCATCGCG
TTCCTGCGCGGCGAGCTTGGTAACCCTCCAGGTGGCTGGCCAGAACC
ACTGCGCACCCGCGCACTGGAAGGCCGCTCCGAAGGCAAGGCACCTC
TGACGGAAGTTCCTGAGGAAGAGCAGGCGCACCTCGACGCTGATGAT
TCCAAGGAACGTCGCAACAGCCTCAACCGCCTGCTGTTCCCGAAGCC
AACCGAAGAGTTCCTCGAGCACCGTCGCCGCTTCGGCAACACCTCTG
CGCTGGATGATCGTGAATTCTTCTACGGACTGGTCGAGGGCCGCGAG
ACTTTGATCCGCCTGCCAGATGTGCGCACCCCACTGCTTGTTCGCCTG
GATGCGATCTCTGAGCCAGACGATAAGGGTATGCGCAATGTTGTGGC
CAACGTCAACGGCCAGATCCGCCCAATGCGTGTGCGTGACCGCTCCG
TTGAGTCTGTCACCGCAACCGCAGAAAAGGCAGATTCCTCCAACAAG
GGCCATGTTGCTGCACCATTCGCTGGTGTTGTCACTGTGACTGTTGCT
GAAGGTGATGAGGTCAAGGCTGGAGATGCAGTCGCAATCATCGAGG
CTATGAAGATGGAAGCAACAATCACTGCTTCTGTTGACGGCAAGATT
GAACGCGTTGTGGTTCCTGCTGCAACGAAGGTGGAAGGTGGCGACTT
GATCGTCGTCGTTTCCTAAGGAAACACAGAAAAAAGCCCGCACCTGA
CAGTGCGGGCTTTTTTTTCGACCAAAGGAGCGATAGCGCCGGCTTA
GTCAGATTTAATCTGCGCGCGTGGTGGATATTTTTTCAGGATCTCCAT
ATACGCGTGCATTTCGGTCTGTAGCGGTACACCCATCGGAATATGAC
GCACGCCGATGGAGTCGCTTTCCTGCGGATCGGTGTAGAGGTTAAAC
ACCGACGATCCCGCCGTTTGCATTACTGTGCCGGTGAATCCACCCTGA
TATCCGCTCTGGGTATAAGCGTAAGGTTGCTGAATCAGGACGTGATA
CTTGAACTCATCCATACGCACAGCAGCGAGTTTACCGTTGAGGAAGT
AGTGCTCGGCCTTACGGTTAGACTGACCATTTGTTCCCAGGAAGAAG
GATGTCTGGTCCACACCATCGATAAAGGTGGTTTTCGGCACTAAATTC
GCCACTTTCGCTCCAGGATGCCCTGCCAGATCCAGCGCGGTAGGGAA
GAGATCTGCCAGATCGACAATACCGTCAGATTTACGCGGTTGGATCA
TCCCTTTCCAGTAAACGAAAGTCGGTACGCGAACGCCGCCTTCCCAG
GTCGAACCTTTCGCACCACGGAACGGGGTGCGTCCGTGCGGCGGTAC
TTCGGCTTCCGGTCCGTTATCGGAGGTAAAGACGATCAGCGTGTTATC
AAGCTGACCGTTTTTCTCCAGTGTTTTATACAGATTAGCGAACACATC
GTTCATCTCCACCATGCAGTCGCCATACGAGGTGCGTGCCGGAGAGC
TACCCGCATATTTCGCATTTGGGTAGTTATCGAAGTGGCAGCCACGA
GTGCCGTAGTAGAGGAAGAATGGTTTATCGCTCTTCGCCATCTTGTCG
AGGAACTTAACGCCATAGTCCATCCAGCGTTGATCCAGATCTTCCAT
ATATTTCGGCGTAATGTCGGCAATGGCCTGTTGTTCGCCGCCGCGCAC
CGCATGAACGTCATCTTTGCTGAACGGTAATTGCTTGATGTATTCAGA
ACGGTCCGGACTCAGGGCCACTTCCGGATTGACG
```

6. Pfoc_*E. coli*_promoter_DNA
    (SEQ ID NO: 6)
```
GATATGATCTATATCAATTTCTCATCTATAATGCTTTGTTAGTA
TCTCGTCGCCGACTTAATAAAGAGAGAGTTAGT
```

7. Pfoc-pyc promoter-gene_DNA
    (SEQ ID NO: 7)
```
GATATGATCTATATCAATTTCTCATCTATAATGCTTTGTTAGTA
TCTCGTCGCCGACTTAATAAAGAGAGAGTTAGTATGTCGACTCACAC
ATCTTCAACGCTTCCAGCATTCAAAAAGATCTTGGTAGCAAACCGCG
GCGAAATCGCGGTCCGTGCTTTCCGTGCAGCACTCGAAACCGGTGCA
GCCACGGTAGCTATTTACCCCCGTGAAGATCGGGGATCATTCCACCG
CTCTTTTGCTTCTGAAGCTGTCCGCATTGGTACTGAAGGCTCACCAGT
CAAGGCGTACCTGGACATCGATGAAATTATCGGTGCAGCTAAAAAAG
TTAAAGCAGATGCTATTTACCCGGGATATGGCTTCCTGTCTGAAAATG
CCCAGCTTGCCCGCGAGTGCGCGGAAAACGGCATTACTTTTATTGGC
CCAACCCCAGAGGTTCTTGATCTCACCGGTGATAAGTCTCGTGCGGT
AACCGCCGCGAAGAAGGCTGGTCTGCCAGTTTTGGCGGAATCCACCC
CGAGCAAAAACATCGATGACATCGTTAAAAGCGCTGAAGGCCAGAC
TTACCCCATCTTTGTAAAGGCAGTTGCCGGTGGTGGCGGACGCGGTA
TGCGCTTTGTTTCTTCACCTGATGAGCTCCGCAAATTGGCAACAGAAG
CATCTCGTGAAGCTGAAGCGGCATTCGGCGACGGTTCGGTATATGTC
GAACGTGCTGTGATTAACCCCCAGCACATTGAAGTGCAGATCCTTGG
CGATCGCACTGGAGAAGTTGTACACCTTTATGAACGTGACTGCTCAC
TGCAGCGTCGTCACCAAAAAGTTGTCGAAATTGCGCCAGCACAGCAT
TTGGATCCAGAACTGCGTGATCGCATTTGTGCGGATGCAGTAAAGTT
CTGCCGCTCCATTGGTTACCAGGGCGCGGGAACCGTGGAATTCTTGG
TCGATGAAAAGGGCAACCACGTTTTCATCGAAATGAACCCACGTATC
CAGGTTGAGCACACCGTGACTGAAGAAGTCACCGAGGTGGACCTGGT
GAAGGCGCAGATGCGCTTGGCTGCTGGTGCAACCTTGAAGGAATTGG
GTCTGACCCAAGATAAGATCAAGACCCACGGTGCAGCACTGCAGTGC
```

```
CGCATCACCACGGAAGATCCAAACAACGGCTTCCGCCCAGATACCGG

AACTATCACCGCGTACCGCTCACCAGGCGGAGCTGGCGTTCGTCTTG

ACGGTGCAGCTCAGCTCGGTGGCGAAATCACCGCACACTTTGACTCC

ATGCTGGTGAAAATGACCTGCCGTGGTTCCGACTTTGAAACTGCTGTT

GCTCGTGCACAGCGCGCGTTGGCTGAGTTCACCGTGTCTGGTGTTGCA

ACCAACATTGGTTTCTTGCGTGCGTTGCTGCGGGAAGAGGACTTCACT

TCCAAGCGCATCGCCACCGGATTTATCGGCGATCACCCACACCTCCTT

CAGGCTCCACCTGCGGATGATGAGCAGGGACGCATCCTGGATTACTT

GGCAGATGTCACCGTGAACAAGCCTCATGGTGTGCGTCCAAAGGATG

TTGCAGCACCAATCGATAAGCTGCCCAACATCAAGGATCTGCCACTG

CCACGCGGTTCCCGTGACCGCCTGAAGCAGCTTGGCCCAGCCGCGTT

TGCTCGTGATCTCCGTGAGCAGGACGCACTGGCAGTTACTGATACCA

CCTTCCGCGATGCACACCAGTCTTTGCTTGCGACCCGAGTCCGCTCAT

TCGCACTGAAGCCTGCGGCAGAGGCCGTCGCAAAGCTGACTCCTGAG

CTTTTGTCCGTGGAGGCCTGGGGCGGCGCGACCTACGATGTGGCGAT

GCGTTTCCTCTTTGAGGATCCGTGGGACAGGCTCGACGAGCTGCGCG

AGGCGATGCCGAATGTAAACATTCAGATGCTGCTTCGCGGCCGCAAC

ACCGTGGGATACACCCCGTACCCAGACTCCGTCTGCCGCGCGTTTGTT

AAGGAAGCTGCCACCTCCGGCGTGGACATCTTCCGCATCTTCGACGC

GCTTAACGACGTCTCCCAGATGCGTCCAGCAATCGACGCAGTCCTGG

AGACCAACACCGCGGTAGCCGAGGTGGCTATGGCTTATTCTGGTGAT

CTCTCTGATCCAAATGAAAAGCTCTACACCCTGGATTACTACCTAAA

GATGGCAGAGGAGATCGTCAAGTCTGGCGCTCACATTCTGGCCATTA

AGGATATGGCTGGTCTGCTTCGCCCAGCTGCGGTAACCAAGCTGGTC

ACCGCACTGCGCCGTGAATTCGATCTGCCAGTGCACGTGCACACCCA

CGACACTGCGGGTGGCCAGTTGGCTACCTACTTTGCTGCAGCTCAAG

CTGGTGCAGATGCTGTTGACGGTGCTTCCGCACCACTGTCTGGCACCA

CCTCCCAGCCATCCCTGTCTGCCATTGTTGCTGCATTCGCGCACACCC

GTCGCGATACCGGTTTGAGCCTCGAGGCTGTTTCTGACCTCGAGCCGT

ACTGGGAAGCTGTGCGCGGACTGTACCTGCCATTTGAGTCTGGAACC

CCAGGCCCAACCGGTCGCGTCTACCGCCACGAAATCCCAGGCGGACA

GTTGTCCAACCTGCGTGCACAGGCCACCGCACTGGGCCTTGCTGATC

GCTTCGAGCTCATCGAAGACAACTACGCAGCCGTTAATGAGATGCTG

GGACGCCCAACCAAGGTCACCCCATCCTCCAAGGTTGTTGGCGACCT

CGCACTCCACCTGGTTGGTGCGGGTGTAGATCCAGCAGACTTTGCTG

CAGACCCACAAAAGTACGACATCCCAGACTCTGTCATCGCGTTCCTG

CGCGGCGAGCTTGGTAACCCTCCAGGTGGCTGGCCAGAACCACTGCG

CACCCGCGCACTGGAAGGCGCTCCGAAGGCAAGGCACCTCTGACGG

AAGTTCCTGAGGAAGAGCAGGCGCACCTCGACGCTGATGATTCCAAG

GAACGTCGCAACAGCCTCAACCGCCTGCTGTTCCCGAAGCCAACCGA

AGAGTTCCTCGAGCACCGTCGCCGCTTCGGCAACACCTCTGCGCTGG

ATGATCGTGAATTCTTCTACGGACTGGTCGAGGGCCGCGAGACTTTG

ATCCGCCTGCCAGATGTGCGCACCCCACTGCTTGTTCGCCTGGATGCG

ATCTCTGAGCCAGACGATAAGGGTATGCGCAATGTTGTGGCCAACGT

CAACGGCCAGATCCGCCCAATGCGTGTGCGTGACCGCTCCGTTGAGT

CTGTCACCGCAACCGCAGAAAAGGCAGATTCCTCCAACAAGGGCCAT

GTTGCTGCACCATTCGCTGGTGTTGTCACTGTGACTGTTGCTGAAGGT

GATGAGGTCAAGGCTGGAGATGCAGTCGCAATCATCGAGGCTATGAA

GATGGAAGCAACAATCACTGCTTCTGTTGACGGCAAGATTGAACGCG

TTGTGGTTCCTGCTGCAACGAAGGTGGAAGGTGGCGACTTGATCGTC

GTCGTTTCCTAA 8. yafV_E. coli_DNA
                                              (SEQ ID NO: 8)
GTGCCTGGTTTGAAGATTACGCTTTTGCAGCAACCACTGGTGT

GGATGGATGGTCCTGCCAACCTGCGTCATTTTGATCGTCAACTGGAA

GGTATTACCGGGCGCGATGTGATCGTTCTACCGGAGATGTTTACCAG

CGGCTTTGCCATGGAAGCGGCAGCTTCGTCGCTAGCACAAGATGACG

TAGTGAACTGGATGACAGCTAAGGCGCAGCAGTGCAATGCGCTGATT

GCAGGCAGTGTTGCATTACAAACGGAGTCTGGTTCGGTTAACCGCTT

TTTGCTGGTTGAGCCGGGCGGCACGGTACATTTTTATGATAAGCGTCA

TCTGTTCCGCATGGCAGATGAGCATCTACATTATAAAGCGGGCAATG

CGCGAGTGATTGTGGAATGGCGCGGCTGGCGTATTTTGCCGCTGGTG

TGCTACGACTTACGTTTTCCTGTGTGGTCGCGCAATCTCAACGATTAT

GACCTCGCCCTGTACGTCGCCAACTGGCCTGCTCCGCGCTCTCTGCAC

TGGCAGGCATTGCTGACGCCCGCGCGATTGAGAATCAGGCGTATGT

GGCGGGATGCAATCGCGTCGGCAGCGATGGCAACGGCTGCCATTATC

GCGGTGACAGCCGGGTGATTAATCCGCAAGGAGAGATTATCGCTACT

GCCGACGCGCATCAGGCAACGCGCATTGATGCGGAGCTGTCGATGGC

AGCATTGCGGGAATATAGAGAAAAGTTTCCGGCATGGCAGGATGCG

GATGAGTTTAGGTTGTGGTGA 9. yafV downstream homology arm_DNA
                                              (SEQ ID NO: 9)
AAACCACTGGCACGTGGAGAATAAGCTGCACAGGCGTCTGGACGTG

GTAATGAATGAAGACGACTACAAAATAAGAAGAGGAAACGCAGCAG

AATTATTTTCAGGGATACGGCACATTGCTATTAATATTTTGACGAATG

AGAAGGTATTCAAGGCAGGGTTAAGACGTAAGATGCGAAAAGCAGC

CATGGACAGAAACTACCTGGCGTCAGTCCTTGCGGGGAGCGGGCTTT

CGTAGTAATACCCCGACTCTCCCCGTCCTTAAACACAACCCCCACTCA

CCACAACCTAAACTCATCCGCATCCTGCCATGCCGGAAACTTTTCTCT

ATATTCCCGCAATGCTGCCATCGACAGCTCCGCATCAATGCGCGTTGC

CTGATGCGCGTCGGCAGTAGCGATAATCTCTCCTTGCGGATTAATCAC

CCGGCTGTCACCGCGATAATGGCAGCCGTTGCCATCGCTGCCGACGC

GATTGCATCCCGCCACATACGCCTGATTCTCAATCGCGCGGGCCGTC
```

AGCAATGCCTGCCAGTGCAGAGAGCGCGGAGCAGGCCAGTTGGCGA
CGTACAGGGCGAGGTCATAATCGTTGAGATTGCGCGACCACACAGGA
AAACGTAAGTCGTAGCACACCAGCGGCAAAATACGCCAGCCGCGCC
ATTCCACAATCACTCGCGCATTGCCCGCTTTATAATGTAGATGCTCAT
CTGCCATGCGGAACAGATGACGCTTATCATAAAAATGTACCGTGCCG
CCCGGCTCAACCAGCAAAAAGCGGTTAACCGAACCAGACTCCGTTTG
TAATGCAACACTGCCTGCAATCAGCGCATTGCACTGCTGCGCCTTAG
CTGTCATCCAGTTCACTACGTCATCTTGTGCTAGCGACGAAGCTGCCG
CTTCCATGGCAAAGCCGCTGGTAAACATCTCCGGTAGAACGATCACA
TCGCGCCCGGTAATACCTTCCAGTTGACGATCAAAATGACGCAGGTT
GGCAGGACCATCCATCCACACCAGTGGTTGCTGCAAAAGCGTAATCT
TCAAACCAGGCAC 10. yafV upstream homology arm_DNA
(SEQ ID NO: 10)
GCTGATATTGGAAATATCTGATTTGCAAATTATCGTGTTATCGCCAGG
CTTTAGGAGGTTAATAACATGGGCAGGATAAGCTCGGGAGGAATGAT
GTTTAAGGCAATAACGACAGTCGCCGCTCTGGTCATCGCCACCAGTG
CAATGGCGCAGGATGATTTAACCATTAGCAGCCTTGCAAAGGGCGAA
ACCACCAAAGCTGCATTTAATCAGATGGTACAAGGGCATAAGCTGCC
TGCCTGGGTGATGAAAGGCGGTACTTATACTCCCGCACAAACCGTAA
CGTTGGGAGATGAGACGTATCAGGTGATGAGCGCGTGCAAACCGCAT
GACTGTGGCTCGCAACGTATCGCTGTGATGTGGTCCGAGAAATCTAA
TCAGATGACGGGGCTGTTCTCGACTATTGATGAGAAAACGTCGCAAG
AGAAACTCACCTGGCTGAATGTGAACGATGCGCTTTCGATTGATGGT
AAAACGGTGTTGTTCGCGGCGTTGACCGGCAGCCTGGAAAACCATCC
GGATGGCTTTAATTTTAAATAATTAGCGGATAAAGAAACGGAGCCTTT
TCGGCTCCGTTATTCATTTACGCGGCTTCAACTTTCCGCACTTTCTCCG
GCAACTTTACCGGCTTCGTCGCCAGCTCTTCCGGATCAAAGTCATCAA
CGTTAATACTGCGCAGACGGCTTTCTTCAGCTTTCACCAGAATAGCGG
CTTCATCTTTATCAATCAGCCCCTTCACCAGCGCGTTGTGCGCCAGTT
CATCCAGACGGGTAAACGGCAGGTTTTTACCCAGCTCTTTACAGATC
CGCTGATGAATTGGGTCGGCGGCAATCACATCCACCAGCGCCTCTTC
CAGCAAGCCAACCGGATTATGCTCGCTCGGCGTCAGGTACTGACCGC
GACCAATGCGGGAACGGGTGGCGTTCGGCACTTGTAAAATCTTCGCC
ACTTTATGATCCAGCTTGTCAGAAGGTGCCAGATAATGACGTCCGGT
CGGGAAGATCACCACATTCAGCAGCCCGGCAACCACGCGGTTCGGGA
AGTTTTGCA 11. yafV downstream homology arm-acs RBS E. coli-T1-yafV upstream homology arm_DNA
(SEQ ID NO: 11)
AAACCACTGGCACGTGGAGAATAAGCTGCACAGGCGTCTGGACGTG
GTAATGAATGAAGACGACTACAAAATAAGAAGAGGAAACGCAGCAG
AATTATTTTCAGGGATACGGCACATTGCTATTAATATTTTGACGAATG AGAAGGTATTCAAGGCAGGGTTAAGACGTAAGATGCGAAAAGCAGC
CATGGACAGAAACTACCTGGCGTCAGTCCTTGCGGGGAGCGGGCTTT
CGTAGTAATACCCCGACTCTCCCCGTCCTTAAACACAACCCCCACTCA
CCACAACCTAAACTCATCCGCATCCTGCCATGCCGGAAACTTTTCTCT
ATATTCCCGCAATGCTGCCATCGACAGCTCCGCATCAATGCGCGTTGC
CTGATGCGCGTCGGCAGTAGCGATAATCTCTCCTTGCGGATTAATCAC
CCGGCTGTCACCGCGATAATGGCAGCCGTTGCCATCGCTGCCGACGC
GATTGCATCCCGCCACATACGCCTGATTCTCAATCGCGCGGGCCGTC
AGCAATGCCTGCCAGTGCAGAGAGCGCGGAGCAGGCCAGTTGGCGA
CGTACAGGGCGAGGTCATAATCGTTGAGATTGCGCGACCACACAGGA
AAACGTAAGTCGTAGCACACCAGCGGCAAAATACGCCAGCCGCGCC
ATTCCACAATCACTCGCGCATTGCCCGCTTTATAATGTAGATGCTCAT
CTGCCATGCGGAACAGATGACGCTTATCATAAAAATGTACCGTGCCG
CCCGGCTCAACCAGCAAAAAGCGGTTAACCGAACCAGACTCCGTTTG
TAATGCAACACTGCCTGCAATCAGCGCATTGCACTGCTGCGCCTTAG
CTGTCATCCAGTTCACTACGTCATCTTGTGCTAGCGACGAAGCTGCCG
CTTCCATGGCAAAGCCGCTGGTAAACATCTCCGGTAGAACGATCACA
TCGCGCCCGGTAATACCTTCCAGTTGACGATCAAAATGACGCAGGTT
GGCAGGACCATCCATCCACACCAGTGGTTGCTGCAAAAGCGTAATCT
TCAAACCAGGCACGCTTTTGTTCTCCTTGTAGGATGTTAATTGAAAAG
CAAGAGGGCCCGCCCCGAAGGTTCGGGGCTGATATTGGAAATATCT
GATTTGCAAATTATCGTGTTATCGCCAGGCTTTAGGAGGTTAATAACA
TGGGCAGGATAAGCTCGGGAGGAATGATGTTTAAGGCAATAACGAC
AGTCGCCGCTCTGGTCATCGCCACCAGTGCAATGGCGCAGGATGATT
TAACCATTAGCAGCCTTGCAAAGGGCGAAACCACCAAAGCTGCATTT
AATCAGATGGTACAAGGGCATAAGCTGCCTGCCTGGGTGATGAAAGG
CGGTACTTATACTCCCGCACAAACCGTAACGTTGGGAGATGAGACGT
ATCAGGTGATGAGCGCGTGCAAACCGCATGACTGTGGCTCGCAACGT
ATCGCTGTGATGTGGTCCGAGAAATCTAATCAGATGACGGGGCTGTT
CTCGACTATTGATGAGAAAACGTCGCAAGAGAAACTCACCTGGCTGA
ATGTGAACGATGCGCTTTCGATTGATGGTAAAACGGTGTTGTTCGCG
GCGTTGACCGGCAGCCTGGAAAACCATCCGGATGGCTTTAATTTTAA
ATAATTAGCGGATAAAGAAACGGAGCCTTTTCGGCTCCGTTATTCATTT
ACGCGGCTTCAACTTTCCGCACTTTCTCCGGCAACTTTACCGGCTTCG
TCGCCAGCTCTTCCGGATCAAAGTCATCAACGTTAATACTGCGCAGA
CGGCTTTCTTCAGCTTTCACCAGAATAGCGGCTTCATCTTTATCAATC
AGCCCCTTCACCAGCGCGTTGTGCGCCAGTTCATCCAGACGGGTAAA
CGGCAGGTTTTTACCCAGCTCTTTACAGATCCGCTGATGAATTGGGTC
GGCGGCAATCACATCCACCAGCGCCTCTTCCAGCAAGCCAACCGGAT
TATGCTCGCTCGGCGTCAGGTACTGACCGCGACCAATGCGGGAACGG
GTGGCGTTCGGCACTTGTAAAATCTTCGCCACTTTATGATCCAGCTTG -continued

TCAGAAGGTGCCAGATAATGACGTCCGGTCGGGAAGATCACCACATT

CAGCAGCCCGGCAACCACGCGGTTCGGGAAGTTTTGCA

12. T1 terminator_DNA (SEQ ID NO: 12)
CCCGAACCTTCGGGGGCGGGCCCTCTTGCTTTTCAAT 13. acs RBS_E. coli_DNA (SEQ ID NO: 13)
TAACATCCTACAAGGAGAACAAAAG 14. T1 terminator-acs RBS-synthetic_DNA (SEQ ID NO: 14)
CCCGAACCTTCGGGGGCGGGCCCTCTTGCTTTTCAATTAACAT

CCTACAAGGAGAACAAAAG

15. T1-acs RBS-yafV _DNA (SEQ ID NO: 15)
CCCGAACCTTCGGGGGCGGGCCCTCTTGCTTTTCAATTAACATCCT

ACAAGGAGAACAAAAGCGTGCCTGGTTTGAAGATTACGCTTTTGCAGCAA

CCACTGGTGTGGATGGATGGTCCTGCCAACCTGCGTCATTTTGATCGTCA

ACTGGAAGGTATTACCGGGCGCGATGTGATCGTTCTACCGGAGATGTTTA

CCAGCGGCTTTGCCATGGAAGCGGCAGCTTCGTCGCTAGCACAAGATGA

CGTAGTGAACTGGATGACAGCTAAGGCGCAGCAGTGCAATGCGCTGATTG

CAGGCAGTGTTGCATTACAAACGGAGTCTGGTTCGGTTAACCGCTTTTTGC

TGGTTGAGCCGGGCGGCACGGTACATTTTTATGATAAGCGTCATCTGTTC

CGCATGGCAGATGAGCATCTACATTATAAAGCGGGCAATGCGCGAGTGAT

TGTGGAATGGCGCGGCTGGCGTATTTTGCCGCTGGTGTGCTACGACTTAC

GTTTTCCTGTGTGGTCGCGCAATCTCAACGATTATGACCTCGCCCTGTACG

TCGCCAACTGGCCTGCTCCGCGCTCTCTGCACTGGCAGGCATTGCTGAC

GGCCCGCGCGATTGAGAATCAGGCGTATGTGGCGGGATGCAATCGCGTC

GGCAGCGATGGCAACGGCTGCCATTATCGCGGTGACAGCCGGGTGATTA

ATCCGCAAGGAGAGATTATCGCTACTGCCGACGCGCATCAGGCAACGCG

CATTGATGCGGAGCTGTCGATGGCAGCATTGCGGGAATATAGAGAAAGT

TTCCGGCATGGCAGGATGCGGATGAGTTTAGGTTGTGGTGA

16. YafV_E. coli_protein (SEQ ID NO: 16)
MPGLKITLLQQPLVWMDGPANLRHFDRQLEGITGRDVIVLPEMF

TSGFAMEAAASSLAQDDVVNWMTAKAQQCNALIAGSVALQTESGSVN

RFLLVEPGGTVHFYDKRHLFRMADEHLHYKAGNARVIVEWRGWRILPL

VCYDLRFPVWSRNLNDYDLALYVANWPAPRSLHWQALLTARAIENQA

YVAGCNRVGSDGNGCHYRGDSRVINPQGEIIATADAHQATRIDAELSMA

ALREYREKFPAWQDADEFRLW 17. rhtC_E. coli_DNA (SEQ ID NO: 17)
ATGTTGATGTTATTTCTCACCGTCGCCATGGTGCACATTGTGGCGCTT

ATGAGCCCCGGTCCCGATTTCTTTTTTGTCTCTCAGACCGCTGTCAGT

CGTTCCCGTAAAGAAGCGATGATGGGCGTGCTGGGCATTACCTGCGG

CGTAATGGTTTGGGCTGGGATTGCGCTGCTTGGCCTGCATTTGATTAT

CGAAAAAATGGCCTGGCTGCATACGCTGATTATGGTGGGCGGTGGCC

TGTATCTCTGCTGGATGGGTTACCAGATGCTACGTGGTGCACTGAAA

AAAGAGGCGGTTTCTGCACCTGCGCCACAGGTCGAGCTGGCGAAAAG

TGGGCGCAGTTTCCTGAAAGGTTTACTGACCAATCTCGCTAATCCGA

AAGCGATTATCTACTTTGGCTCGGTGTTCTCATTGTTTGTCGGTGATA

ACGTTGGCACTACCGCGCGCTGGGGCATTTTTGCGCTGATCATTGTCG

AAACGCTGGCGTGGTTTACCGTCGTTGCCAGCCTGTTTGCCCTGCCGC

AAATGCGCCGTGGTTATCAACGTCTGGCGAAGTGGATTGATGGTTTT

GCCGGGGCGTTATTTGCCGGATTTGGCATTCATTTGATTATTTCGCGG

TGA

18. PrhtC-rhtC_E. coli_DNA (SEQ ID NO: 18)
GGCGTTGGGATGCGCAAGCTGGAACGCTTTGGCAAACCGTTTATGGC

GCTGATTCGTGCGCATGTTGATGGCGATGACGAAGAGTAGTCAGCAG

CATAAAAAAGTGCCAGTATGAAGACTCCGTAAACGTTTCCCCCGCGA

GTCAAATGTATGTTGATGTTATTTCTCACCGTCGCCATGGTGCACATT

GTGGCGCTTATGAGCCCCGGTCCCGATTTCTTTTTTGTCTCTCAGACC

GCTGTCAGTCGTTCCCGTAAAGAAGCGATGATGGGCGTGCTGGGCAT

TACCTGCGGCGTAATGGTTTGGGCTGGGATTGCGCTGCTTGGCCTGCA

TTTGATTATCGAAAAAATGGCCTGGCTGCATACGCTGATTATGGTGG

GCGGTGGCCTGTATCTCTGCTGGATGGGTTACCAGATGCTACGTGGT

GCACTGAAAAAAGAGGCGGTTTCTGCACCTGCGCCACAGGTCGAGCT

GGCGAAAAGTGGGCGCAGTTTCCTGAAAGGTTTACTGACCAATCTCG

CTAATCCGAAAGCGATTATCTACTTTGGCTCGGTGTTCTCATTGTTTG

TCGGTGATAACGTTGGCACTACCGCGCGCTGGGGCATTTTTGCGCTG

ATCATTGTCGAAACGCTGGCGTGGTTTACCGTCGTTGCCAGCCTGTTT

GCCCTGCCGCAAATGCGCCGTGGTTATCAACGTCTGGCGAAGTGGAT

TGATGGTTTTGCCGGGGCGTTATTTGCCGGATTTGGCATTCATTTGAT

TATTTCGCGGTGA 19. rhtC upstream homology arm_E. coli_DNA (SEQ ID NO: 19)
ATTCCAGCGCGATGACCTGCAAATTGTGGTGGCGACGGTGGCGTTCG

GCATGGGCATCAATAAACCAAACGTTCGCTTCGTGGTCCACTTTGAT

ATTCCGCGCAATATCGAATCCTATTATCAGGAAACCGGACGCGCCGG

GCGTGATGGCCTGCCCGCGGAAGCGATGCTGTTTTACGATCCGGCTG

ATATGGCGTGGCTGCGCCGTTGTCTGGAAGAGAAGCCGCAGGGGCAG

TTGCAGGATATCGAGCGCCACAAACTCAATGCGATGGGCGCGTTTGC

CGAAGCGCAAACTTGCCGTCGTCTGGTATTGCTGAACTATTTTGGCGA

AGGGCGTCAGGAGCCGTGCGGGAACTGCGATATCTGCCTCGATCCGC

CGAAACAGTACGACGGTTCAACCGATGCTCAGATTGCCCTTTCCACC

ATTGGTCGTGTGAATCAGCGGTTTGGGATGGGTTATGTGGTGGAAGT

GATTCGTGGTGCTAATAACCAGCGTATCCGCGACTATGGTCATGACA

AACTGAAAGTCTATGGCATGGGCCGTGATAAAAGCCATGAACATTGG

GTGAGCGTGATCCGCCAGCTGATTCACCTCGGCCTGGTGACGCAAAA

TATTGCCCAGCATTCTGCCCTACAACTGACAGAGGCCGCGCGCCCGG
TGCTGCGCGGCGAATCCTCTTTGCAACTTGCCGTGCCGCGTATCGTGG
CGCTCAAACCGAAAGCGATGCAGAAATCGTTCGGCGGCAACTATGAT
CGCAAACTGTTCGCCAAATTACGCAAACTGCGTAAATCGATAGCCGA
TGAAAGTAATGTCCCGCCGTACGTGGTGTTTAACGACGCAACCTTGA
TTGAGATGGCTGAACAGATGCCGATCACCGCCAGCGAAATGCTCAGC
GTTAACGGCGTTGGGATGCGCAAGCTGGAACGCTTTGGCAAACCGTT
TATGGCGCTGATTCGTGCGCATGTTGATGGCGATGACGAAGAGTAGT
CAGCAGCATAAAAAAGTGCCAGTATGAAGACTCCGTAAACGTTTCCC
CCGCGAGTCAAATGT 20. rhtC downstream homology arm_E. coli_DNA
(SEQ ID NO: 20)
ATGTTGATGTTATTTCTCACCGTCGCCATGGTGCACATTGTGGCGCTT
ATGAGCCCCGGTCCCGATTTCTTTTTTGTCTCTCAGACCGCTGTCAGT
CGTTCCCGTAAAGAAGCGATGATGGGCGTGCTGGGCATTACCTGCGG
CGTAATGGTTTGGGCTGGGATTGCGCTGCTTGGCCTGCATTTGATTAT
CGAAAAAATGGCCTGGCTGCATACGCTGATTATGGTGGGCGGTGGCC
TGTATCTCTGCTGGATGGGTTACCAGATGCTACGTGGTGCACTGAAA
AAAGAGGCGGTTTCTGCACCTGCGCCACAGGTCGAGCTGGCGAAAAG
TGGGCGCAGTTTCCTGAAAGGTTTACTGACCAATCTCGCTAATCCGA
AAGCGATTATCTACTTTGGCTCGGTGTTCTCATTGTTTGTCGGTGATA
ACGTTGGCACTACCGCGCGCTGGGGCATTTTTGCGCTGATCATTGTCG
AAACGCTGGCGTGGTTTACCGTCGTTGCCAGCCTGTTTGCCCTGCCGC
AAATGCGCCGTGGTTATCAACGTCTGGCGAAGTGGATTGATGGTTTT
GCCGGGGCGTTATTTGCCGGATTTGGCATTCATTTGATTATTTCGCGG
TGATGCCAGACGCGTCTTCAGAGTAAGTCGGATAAGGCGTTTACGCC
GCATCCGACATTATTTTTCACGCATGCCTCGCCGATGCTAACAGCGCT
CCCACCAGCATAAACAACGAGCCGAAAATCTTATTCAGCGCCTTCAT
CTGCTTTGGTCCTTTAATCCATAGAGCAATCCGTTGAGCAAGGGTGGC
GTAACCGATCATCACAATAATATCGACCACAATAGTGGTGACGCCGA
GCACGATATACTGCATCAGTTGCGGCTGTTGCGGCATGATGAATTGC
GGAAATAGCGCCGCCAGAAACACAATACTTTTGGGATTGGTGAGATT
CACAAAAACTGCGCGCTGGAACAAATGTCGACGCGATTGAGTAGAG
GCCAGCGATTTAAGGTCAATTGCACCAGCGGCG 21. rhtC upstream homology arm-synthetic RBS-
rhtC downstream homology arm
(SEQ ID NO: 21)
ATTCCAGCGCGATGACCTGCAAATTGTGGTGGCGACGGTGGCGTTCG
GCATGGGCATCAATAAACCAAACGTTCGCTTCGTGGTCCACTTTGAT
ATTCCGCGCAATATCGAATCCTATTATCAGGAAACCGGACGCGCCGG
GCGTGATGGCCTGCCCGCGGAAGCGATGCTGTTTTACGATCCGGCTG
ATATGGCGTGGCTGCGCCGTTGTCTGGAAGAGAAGCCGCAGGGGCAG
TTGCAGGATATCGAGCGCCACAAACTCAATGCGATGGGCGCGTTTGC CGAAGCGCAAACTTGCCGTCGTCTGGTATTGCTGAACTATTTTGGCGA
AGGGCGTCAGGAGCCGTGCGGGAACTGCGATATCTGCCTCGATCCGC
CGAAACAGTACGACGGTTCAACCGATGCTCAGATTGCCCTTTCCACC
ATTGGTCGTGTGAATCAGCGGTTTGGGATGGGTTATGTGGTGGAAGT
GATTCGTGGTGCTAATAACCAGCGTATCCGCGACTATGGTCATGACA
AACTGAAAGTCTATGGCATGGGCCGTGATAAAAGCCATGAACATTGG
GTGAGCGTGATCCGCCAGCTGATTCACCTCGGCCTGGTGACGCAAAA
TATTGCCCAGCATTCTGCCCTACAACTGACAGAGGCCGCGCGCCCGG
TGCTGCGCGGCGAATCCTCTTTGCAACTTGCCGTGCCGCGTATCGTGG
CGCTCAAACCGAAAGCGATGCAGAAATCGTTCGGCGGCAACTATGAT
CGCAAACTGTTCGCCAAATTACGCAAACTGCGTAAATCGATAGCCGA
TGAAAGTAATGTCCCGCCGTACGTGGTGTTTAACGACGCAACCTTGA
TTGAGATGGCTGAACAGATGCCGATCACCGCCAGCGAAATGCTCAGC
GTTAACGGCGTTGGGATGCGCAAGCTGGAACGCTTTGGCAAACCGTT
TATGGCGCTGATTCGTGCGCATGTTGATGGCGATGACGAAGAGTAGT
CAGCAGCATAAAAAAGTGCCAGTATGAAGACTCCGTAAACGTTTCCC
CCGCGAGTCAAATGTAATTGAATAAACTAAGGAGGTTAAAGTATGTT
GATGTTATTTCTCACCGTCGCCATGGTGCACATTGTGGCGCTTATGAG
CCCCGGTCCCGATTTCTTTTTTGTCTCTCAGACCGCTGTCAGTCGTTCC
CGTAAAGAAGCGATGATGGGCGTGCTGGGCATTACCTGCGGCGTAAT
GGTTTGGGCTGGGATTGCGCTGCTTGGCCTGCATTTGATTATCGAAAA
AATGGCCTGGCTGCATACGCTGATTATGGTGGGCGGTGGCCTGTATC
TCTGCTGGATGGGTTACCAGATGCTACGTGGTGCACTGAAAAAAGAG
GCGGTTTCTGCACCTGCGCCACAGGTCGAGCTGGCGAAAAGTGGGCG
CAGTTTCCTGAAAGGTTTACTGACCAATCTCGCTAATCCGAAAGCGA
TTATCTACTTTGGCTCGGTGTTCTCATTGTTTGTCGGTGATAACGTTGG
CACTACCGCGCGCTGGGGCATTTTTGCGCTGATCATTGTCGAAACGCT
GGCGTGGTTTACCGTCGTTGCCAGCCTGTTTGCCCTGCCGCAAATGCG
CCGTGGTTATCAACGTCTGGCGAAGTGGATTGATGGTTTTGCCGGGG
CGTTATTTGCCGGATTTGGCATTCATTTGATTATTTCGCGGTGATGCC
AGACGCGTCTTCAGAGTAAGTCGGATAAGGCGTTTACGCCGCATCCG
ACATTATTTTTCACGCATGCCTCGCCGATGCTAACAGCGCTCCCACCA
GCATAAACAACGAGCCGAAAATCTTATTCAGCGCCTTCATCTGCTTTG
GTCCTTTAATCCATAGAGCAATCCGTTGAGCAAGGGTGGCGTAACCG
ATCATCACAATAATATCGACCACAATAGTGGTGACGCCGAGCACGAT
ATACTGCATCAGTTGCGGCTGTTGCGGCATGATGAATTGCGGAAATA
GCGCCGCCAGAAACACAATACTTTTGGGATTGGTGAGATTCACAAAA
ACTGCGCGCTGGAACAAATGTCGACGCGATTGAGTAGAGGCCAGCG
ATTTAAGGTCAATTGCACCAGCGGCG 22. PrhtC_E. coli_promoter
(SEQ ID NO: 22)
GGCGTTGGGATGCGCAAGCTGGAACGCTTTGGCAAACCGTTTATGGC

GCTGATTCGTGCGCATGTTGATGGCGATGACGAAGAGTAGTCAGCAG

CATAAAAAAGTGCCAGTATGAAGACTCCGTAAACGTTTCCCCCGCGA

GTCAAATGT 23. synthetic RBS_DNA
(SEQ ID NO: 23)
AATTGAATAAACTAAGGAGGTTAAAGT

24. PrhtC-synthetic RBS-rhtC_DNA
(SEQ ID NO: 24)
GGCGTTGGGATGCGCAAGCTGGAACGCTTTGGCAAACCGTTTA

TGGCGCTGATTCGTGCGCATGTTGATGGCGATGACGAAGAGTAGTCA

GCAGCATAAAAAAGTGCCAGTATGAAGACTCCGTAAACGTTTCCCCC

GCGAGTCAAATGTAATTGAATAAACTAAGGAGGTTAAAGTATGTTGA

TGTTATTTCTCACCGTCGCCATGGTGCACATTGTGGCGCTTATGAGCC

CCGGTCCCGATTTCTTTTTTGTCTCTCAGACCGCTGTCAGTCGTTCCCG

TAAAGAAGCGATGATGGGCGTGCTGGGCATTACCTGCGGCGTAATGG

TTTGGGCTGGGATTGCGCTGCTTGGCCTGCATTTGATTATCGAAAAAA

TGGCCTGGCTGCATACGCTGATTATGGTGGGCGGTGGCCTGTATCTCT

GCTGGATGGGTTACCAGATGCTACGTGGTGCACTGAAAAAAGAGGCG

GTTTCTGCACCTGCGCCACAGGTCGAGCTGGCGAAAAGTGGGCGCAG

TTTCCTGAAAGGTTTACTGACCAATCTCGCTAATCCGAAAGCGATTAT

CTACTTTGGCTCGGTGTTCTCATTGTTTGTCGGTGATAACGTTGGCAC

TACCGCGCGCTGGGGCATTTTTGCGCTGATCATTGTCGAAACGCTGGC

GTGGTTTACCGTCGTTGCCAGCCTGTTTGCCCTGCCGCAAATGCGCCG

TGGTTATCAACGTCTGGCGAAGTGGATTGATGGTTTTGCCGGGGCGTT

ATTTGCCGGATTTGGCATTCATTTGATTATTTCGCGGTGA

25. RhtC_E. coli_protein
(SEQ ID NO: 25)
MLMLFLTVAMVHIVALMSPGPDFFFVSQTAVSRSRKEAMMGVL

GITCGVMVWAGIALLGLHLIIEKMAWLHTLIMVGGGLYLCWMGYQML

RGALKKEAVSAPAPQVELAKSGRSFLKGLLTNLANPKAIIYFGSVFSLFV

GDNVGTTARWGIFALIIVETLAWFTVVASLFALPQMRRGYQRLAKWIDG

FAGALFAGFGIHLIISR 26. ilvA_E. coli_DNA
(SEQ ID NO: 26)
ATGGCTGACTCGCAACCCCTGTCCGGTGCTCCGGAAGGTGCCG

AATATTTAAGAGCAGTGCTGCGCGCGCCGGTTTACGAGGCGGCGCAG

GTTACGCCGCTACAAAAAATGGAAAAACTGTCGTCGCGTCTTGATAA

CGTCATTCTGGTGAAGCGCGAAGATCGCCAGCCAGTGCACAGCTTTA

AGCTGCGCGGCGCATACGCCATGATGGCGGGCCTGACGGAAGAACA

GAAAGCGCACGGCGTGATCACTGCTTCTGCGGGTAACCACGCGCAGG

GCGTCGCGTTTTCTTCTGCGCGGTTAGGCGTGAAGGCCCTGATCGTTA

TGCCAACCGCCACCGCCGACATCAAAGTCGACGCGGTGCGCGGCTTC

GGCGGCGAAGTGCTGCTCCACGGCGCGAACTTTGATGAAGCGAAAGC

CAAAGCGATCGAACTGTCACAGCAGCAGGGGTTCACCTGGGTGCCGC

CGTTCGACCATCCGATGGTGATTGCCGGGCAAGGCACGCTGGCGCTG

GAACTGCTCCAGCAGGACGCCCATCTCGACCGCGTATTTGTGCCAGT

CGGCGGCGGCGGTCTGGCTGCTGGCGTGGCGGTGCTGATCAAACAAC

TGATGCCGCAAATCAAAGTGATCGCCGTAGAAGCGGAAGACTCCGCC

TGCCTGAAAGCAGCGCTGGATGCGGGTCATCCGGTTGATCTGCCGCG

CGTAGGGCTATTTGCTGAAGGCGTAGCGGTAAAACGCATCGGTGACG

AAACCTTCCGTTTATGCCAGGAGTATCTCGACGACATCATCACCGTCG

ATAGCGATGCGATCTGTGCGGCGATGAAGGATTTATTCGAAGATGTG

CGCGCGGTGGCGGAACCCTCTGGCGCGCTGGCGCTGGCGGGAATGAA

AAAATATATCGCCCTGCACAACATTCGCGGCGAACGGCTGGCGCATA

TTCTTTCCGGTGCCAACGTGAACTTCCACGGCCTGCGCTACGTCTCAG

AACGCTGCGAACTGGGCGAACAGCGTGAAGCGTTGTTGGCGGTGACC

ATTCCGGAAGAAAAAGGCAGCTTCCTCAAATTCTGCCAACTGCTTGG

CGGGCGTTCGGTCACCGAGTTCAACTACCGTTTTGCCGATGCCAAAA

ACGCCTGCATCTTTGTCGGTGTGCGCCTGAGCCGCGGCCTCGAAGAG

CGCAAAGAAATTTTGCAGATGCTCAACGACGGCGGCTACAGCGTGGT

TGATCTCTCCGACGACGAAATGGCGAAGCTACACGTGCGCTATATGG

TCGGCGGACGTCCATCGCATCCGTTGCAGGAACGCCTCTACAGCTTC

GAATTCCCGGAATCACCGGGCGCGCTGCTGCGCTTCCTCAACACGCT

GGGTACGTACTGGAACATTTCTTTGTTCCACTATCGCAGCCATGGCAC

CGACTACGGGCGCGTACTGGCGGCGTTCGAACTTGGCGACCATGAAC

CGGATTTCGAAACCCGGCTGAATGAGCTGGGCTACGATTGCCACGAC

GAAACCAATAACCCGGCGTTCAGGTTCTTTTTGGCGGGTTAG

27. IlvA_E. coli_protein
(SEQ ID NO: 27)
MADSQPLSGAPEGAEYLRAVLRAPVYEAAQVTPLQKMEKLSSRL

DNVILVKREDRQPVHSFKLRGAYAMMAGLTEEQKAHGVITASAGNHAQ

GVAFSSARLGVKALIVMPTATADIKVDAVRGFGGEVLLHGANFDEAKA

KAIELSQQQGFTWVPPFDHPMVIAGQGTLALELLQQDAHLDRVFVPVGG

GGLAAGVAVLIKQLMPQIKVIAVEAEDSACLKAALDAGHPVDLPRVGLF

AEGVAVKRIGDETFRLCQEYLDDIITVDSDAICAAMKDLFEDVRAVAEPS

GALALAGMKKYIALHNIRGERLAHILSGANVNFHGLRYVSERCELGEQR

EALLAVTIPEEKGSFLKFCQLLGGRSVTEFNYRFADAKNACIFVGVRLSR

GLEERKEILQMLNDGGYSVVDLSDDEMAKLHVRYMVGGRPSHPLQERL

YSFEFPESPGALLRFLNTLGTYWNISLFHYRSHGTDYGRVLAAFELGDHE

PDFETRLNELGYDCHDETNNPAFRFFLAG 28. ilvA upstream homology arm_E. coli_DNA
(SEQ ID NO: 28)
CATGACGCTGGATATCGCGATGGGTGGATCGACTAACACCGTACTTC

ACCTGCTGGCGGCGGCGCAGGAAGCGGAAATCGACTTCACCATGAGT

GATATCGATAAGCTTTCCCGCAAGGTTCCACAGCTGTGTAAAGTTGC

GCCGAGCACCCAGAAATACCATATGGAAGATGTTCACCGTGCTGGTG

GTGTTATCGGTATTCTCGGCGAACTGGATCGCGCGGGGTTACTGAAC

CGTGATGTGAAAAACGTACTTGGCCTGACGTTGCCGCAAACGCTGGA

ACAATACGACGTTATGCTGACCCAGGATGACGCGGTAAAAAATATGT

TCCGCGCAGGTCCTGCAGGCATTCGTACCACACAGGCATTCTCGCAA

GATTGCCGTTGGGATACGCTGGACGACGATCGCGCCAATGGCTGTAT

CCGCTCGCTGGAACACGCCTACAGCAAAGACGGCGGCCTGGCGGTGC

TCTACGGTAACTTTGCGGAAAACGGCTGCATCGTGAAAACGGCAGGC

GTCGATGACAGCATCCTCAAATTCACCGGCCCGGCGAAAGTGTACGA

AAGCCAGGACGATGCGGTAGAAGCGATTCTCGGCGGTAAAGTTGTCG

CCGGAGATGTGGTAGTAATTCGCTATGAAGGCCCGAAAGGCGGTCCG

GGGATGCAGGAAATGCTCTACCCAACCAGCTTCCTGAAATCAATGGG

TCTCGGCAAAGCCTGTGCGCTGATCACCGACGGTCGTTTCTCTGGTGG

CACCTCTGGTCTTTCCATCGGCCACGTCTCACCGGAAGCGGCAAGCG

GCGGCAGCATTGGCCTGATTGAAGATGGTGACCTGATCGCTATCGAC

ATCCCGAACCGTGGCATTCAGTTACAGGTAAGCGATGCCGAACTGGC

GGCGCGTCGTGAAGCGCAGGACGCTCGAGGTGACAAAGCCTGGACG

CCGAAAAATCGTGAACGTCAGGTCTCCTTTGCCCTGCGTGCTTATGCC

AGCCTGGCAACCAGCGCCGACAAAGGCGCGGTGCGCGATAAATCGA

AACTGGGGGGTTAATA 29. ilvA downstream homology arm_E. coli_DNA
(SEQ ID NO: 29)
GGCTGACTCGCAACCCCTGTCCGGTGCTCCGGAAGGTGCCGAATATT

TAAGAGCAGTGCTGCGCGCGCCGGTTTACGAGGCGGCGCAGGTTACG

CCGCTACAAAAAATGGAAAAACTGTCGTCGCGTCTTGATAACGTCAT

TCTGGTGAAGCGCGAAGATCGCCAGCCAGTGCACAGCTTTAAGCTGC

GCGGCGCATACGCCATGATGGCGGGCCTGACGGAAGAACAGAAAGC

GCACGGCGTGATCACTGCTTCTGCGGGTAACCACGCGCAGGGCGTCG

CGTTTTCTTCTGCGCGGTTAGGCGTGAAGGCCCTGATCGTTATGCCAA

CCGCCACCGCCGACATCAAAGTCGACGCGGTGCGCGGCTTCGGCGGC

GAAGTGCTGCTCCACGGCGCGAACTTTGATGAAGCGAAAGCCAAAGC

GATCGAACTGTCACAGCAGCAGGGGTTCACCTGGGTGCCGCCGTTCG

ACCATCCGATGGTGATTGCCGGGCAAGGCACGCTGGCGCTGGAACTG

CTCCAGCAGGACGCCCATCTCGACCGCGTATTTGTGCCAGTCGGCGG

CGGCGGTCTGGCTGCTGGCGTGGCGGTGCTGATCAAACAACTGATGC

CGCAAATCAAAGTGATCGCCGTAGAAGCGGAAGACTCCGCCTGCCTG

AAAGCAGCGCTGGATGCGGGTCATCCGGTTGATCTGCCGCGCGTAGG

GCTATTTGCTGAAGGCGTAGCGGTAAAACGCATCGGTGACGAAACCT

TCCGTTTATGCCAGGAGTATCTCGACGACATCATCACCGTCGATAGC

GATGCGATCTGTGCGGCGATGAAGGATTTATTCGAAGATGTGCGCGC

GGTGGCGGAACCCTCTGGCGCGCTGGCGCTGGCGGGAATGAAAAAA

TATATCGCCCTGCACAACATTCGCGGCGAACGGCTGGCGCATATTCTT

TCCGGTGCCAACGTGAACTTCCACGGCCTGCGCTACGTCTCAGAACG

CTGCGAACTGGGCGAACAGCGTGAAGCGTTGTTGGCGGTGACCATTC

CGGAAGAAAAAGGC 30. ilvA upstream homology arm-T1-cro RBS-ilvA downstream homology arm_DNA
(SEQ ID NO: 30)
CATGACGCTGGATATCGCGATGGGTGGATCGACTAACACCGTACTTC

ACCTGCTGGCGGCGGCGCAGGAAGCGGAAATCGACTTCACCATGAGT

GATATCGATAAGCTTTCCCGCAAGGTTCCACAGCTGTGTAAAGTTGC

GCCGAGCACCCAGAAATACCATATGGAAGATGTTCACCGTGCTGGTG

GTGTTATCGGTATTCTCGGCGAACTGGATCGCGCGGGGTTACTGAAC

CGTGATGTGAAAAACGTACTTGGCCTGACGTTGCCGCAAACGCTGGA

ACAATACGACGTTATGCTGACCCAGGATGACGCGGTAAAAAATATGT

TCCGCGCAGGTCCTGCAGGCATTCGTACCACACAGGCATTCTCGCAA

GATTGCCGTTGGGATACGCTGGACGACGATCGCGCCAATGGCTGTAT

CCGCTCGCTGGAACACGCCTACAGCAAAGACGGCGGCCTGGCGGTGC

TCTACGGTAACTTTGCGGAAAACGGCTGCATCGTGAAAACGGCAGGC

GTCGATGACAGCATCCTCAAATTCACCGGCCCGGCGAAAGTGTACGA

AAGCCAGGACGATGCGGTAGAAGCGATTCTCGGCGGTAAAGTTGTCG

CCGGAGATGTGGTAGTAATTCGCTATGAAGGCCCGAAAGGCGGTCCG

GGGATGCAGGAAATGCTCTACCCAACCAGCTTCCTGAAATCAATGGG

TCTCGGCAAAGCCTGTGCGCTGATCACCGACGGTCGTTTCTCTGGTGG

CACCTCTGGTCTTTCCATCGGCCACGTCTCACCGGAAGCGGCAAGCG

GCGGCAGCATTGGCCTGATTGAAGATGGTGACCTGATCGCTATCGAC

ATCCCGAACCGTGGCATTCAGTTACAGGTAAGCGATGCCGAACTGGC

GGCGCGTCGTGAAGCGCAGGACGCTCGAGGTGACAAAGCCTGGACG

CCGAAAAATCGTGAACGTCAGGTCTCCTTTGCCCTGCGTGCTTATGCC

AGCCTGGCAACCAGCGCCGACAAAGGCGCGGTGCGCGATAAATCGA

AACTGGGGGGTTAATACCCGAACCTTCGGGGGCGGGCCCTCTTGCTT

TTCAATGGTTGCATGTACTAAGGAGGTTGTATGGCTGACTCGCAACC

CCTGTCCGGTGCTCCGGAAGGTGCCGAATATTTAAGAGCAGTGCTGC

GCGCGCCGGTTTACGAGGCGGCGCAGGTTACGCCGCTACAAAAAATG

GAAAAACTGTCGTCGCGTCTTGATAACGTCATTCTGGTGAAGCGCGA

AGATCGCCAGCCAGTGCACAGCTTTAAGCTGCGCGGCGCATACGCCA

TGATGGCGGGCCTGACGGAAGAACAGAAAGCGCACGGCGTGATCAC

TGCTTCTGCGGGTAACCACGCGCAGGGCGTCGCGTTTTCTTCTGCGCG

GTTAGGCGTGAAGGCCCTGATCGTTATGCCAACCGCCACCGCCGACA

TCAAAGTCGACGCGGTGCGCGGCTTCGGCGGCGAAGTGCTGCTCCAC

GGCGCGAACTTTGATGAAGCGAAAGCCAAAGCGATCGAACTGTCAC

AGCAGCAGGGGTTCACCTGGGTGCCGCCGTTCGACCATCCGATGGTG

ATTGCCGGGCAAGGCACGCTGGCGCTGGAACTGCTCCAGCAGGACGC

CCATCTCGACCGCGTATTTGTGCCAGTCGGCGGCGGCGGTCTGGCTG
CTGGCGTGGCGGTGCTGATCAAACAACTGATGCCGCAAATCAAAGTG
ATCGCCGTAGAAGCGGAAGACTCCGCCTGCCTGAAAGCAGCGCTGGA
TGCGGGTCATCCGGTTGATCTGCCGCGCGTAGGGCTATTTGCTGAAG
GCGTAGCGGTAAAACGCATCGGTGACGAAACCTTCCGTTTATGCCAG
GAGTATCTCGACGACATCATCACCGTCGATAGCGATGCGATCTGTGC
GGCGATGAAGGATTTATTCGAAGATGTGCGCGCGGTGGCGGAACCCT
CTGGCGCGCTGGCGCTGGCGGGAATGAAAAAATATATCGCCCTGCAC
AACATTCGCGGCGAACGGCTGGCGCATATTCTTTCCGGTGCCAACGT
GAACTTCCACGGCCTGCGCTACGTCTCAGAACGCTGCGAACTGGGCG
AACAGCGTGAAGCGTTGTTGGCGGTGACCATTCCGGAAGAAAAGG
C

31. T1 terminator-cro RBS_DNA (SEQ ID NO: 31)
CCCGAACCTTCGGGGGCGGGCCCTCTTGCTTTTCAATGGTTGCATGTA
CTAAGGAGGTTGT 32. cro RBS_E. coli_DNA (SEQ ID NO: 32)
GGTTGCATGTACTAAGGAGGTTGT 33. T1-cro RBS-ilvA_DNA (SEQ ID NO: 33)
CCCGAACCTTCGGGGGCGGGCCCTCTTGCTTTTCAATGGTTGC
ATGTACTAAGGAGGTTGTATGGCTGACTCGCAACCCCTGTCCGGTGC
TCCGGAAGGTGCCGAATATTTAAGAGCAGTGCTGCGCGCGCCGGTTT
ACGAGGCGGCGCAGGTTACGCCGCTACAAAAAATGGAAAAACTGTC
GTCGCGTCTTGATAACGTCATTCTGGTGAAGCGCGAAGATCGCCAGC
CAGTGCACAGCTTTAAGCTGCGCGGCGCATACGCCATGATGGCGGGC
CTGACGAAGAACAGAAAGCGCACGGCGTGATCACTGCTTCTGCGGG
TAACCACGCGCAGGGCGTCGCGTTTTCTTCTGCGCGGTTAGGCGTGA
AGGCCCTGATCGTTATGCCAACCGCCACCGCCGACATCAAAGTCGAC
GCGGTGCGCGGCTTCGGCGGCGAAGTGCTGCTCCACGGCGCGAACTT
TGATGAAGCGAAAGCCAAAGCGATCGAACTGTCACAGCAGCAGGGG
TTCACCTGGGTGCCGCCGTTCGACCATCCGATGGTGATTGCCGGGCA
AGGCACGCTGGCGCTGGAACTGCTCCAGCAGGACGCCCATCTCGACC
GCGTATTTGTGCCAGTCGGCGGCGGCGGTCTGGCTGCTGGCGTGGCG
GTGCTGATCAAACAACTGATGCCGCAAATCAAAGTGATCGCCGTAGA
AGCGGAAGACTCCGCCTGCCTGAAAGCAGCGCTGGATGCGGGTCATC
CGGTTGATCTGCCGCGCGTAGGGCTATTTGCTGAAGGCGTAGCGGTA
AAACGCATCGGTGACGAAACCTTCCGTTTATGCCAGGAGTATCTCGA
CGACATCATCACCGTCGATAGCGATGCGATCTGTGCGGCGATGAAGG
ATTTATTCGAAGATGTGCGCGCGGTGGCGGAACCCTCTGGCGCGCTG
GCGCTGGCGGGAATGAAAAAATATATCGCCCTGCACAACATTCGCGG
CGAACGGCTGGCGCATATTCTTTCCGGTGCCAACGTGAACTTCCACG
GCCTGCGCTACGTCTCAGAACGCTGCGAACTGGGCGAACAGCGTGAA
GCGTTGTTGGCGGTGACCATTCCGGAAGAAAAAGGCAGCTTCCTCAA
ATTCTGCCAACTGCTTGGCGGGCGTTCGGTCACCGAGTTCAACTACCG
TTTTGCCGATGCCAAAAACGCCTGCATCTTTGTCGGTGTGCGCCTGAG
CCGCGGCCTCGAAGAGCGCAAAGAAATTTTGCAGATGCTCAACGACG
GCGGCTACAGCGTGGTTGATCTCTCCGACGACGAAATGGCGAAGCTA
CACGTGCGCTATATGGTCGGCGGACGTCCATCGCATCCGTTGCAGGA
ACGCCTCTACAGCTTCGAATTCCCGGAATCACCGGGCGCGCTGCTGC
GCTTCCTCAACACGCTGGGTACGTACTGGAACATTTCTTTGTTCCACT
ATCGCAGCCATGGCACCGACTACGGGCGCGTACTGGCGGCGTTCGAA
CTTGGCGACCATGAACCGGATTTCGAAACCCGGCTGAATGAGCTGGG
CTACGATTGCCACGACGAAACCAATAACCCGGCGTTCAGGTTCTTTTT
GGCGGGTTAG 34. Plasmid AV15_DNA (SEQ ID NO: 34)
CTGGGGCGCCCTCTGGTAAGGTTGGGAAGCCCTGCAAAGTAAACTGG
ATGCCAGGCATCAAATAAAACGAAAGGCTCAGTCGAAAGACTGGGC
CTTTCGTTTTATCTGTTGTTTGTCGGTGAACGCTCTCGCACTAGGACTT
GCCGCGGATACTGCCCCATTACATGAATTGCAGCCTCAGGGACGTCA
GTAGATCATGGAGGTAGGGCATATGTCCTCTGTTGTTAAAATGTGAG
TTCTCAACGAAGCACGAATCGGTCAGAACCTACACTAAGGAGATTTG
GTAGGTGCACGGTTTCTGTCGCATAGACCAGTTCATTTCAGATGTCTG
GCACGTAAGAGGTTCCAACTTTCACCATAATGAAATAAGATCACTAC
CGGGCGTATTTTTTGAGTTATCGAGATTTTCAGGAGCTAAGGAAGCT
AAAATGATTGAACAAGATGGATTGCACGCAGGTTCTCCGGCCGCTTG
GGTGGAGAGGCTATTCGGCTATGACTGGGCACAACAGACAATCGGCT
GCTCTGATGCCGCCGTGTTCCGGCTGTCAGCGCAGGGGCGCCCGGTT
CTTTTTGTCAAGACCGACCTGTCCGGTGCCCTGAATGAACTCCAAGAC
GAGGCAGCGCGGCTATCGTGGCTGGCCACGACGGGCGTTCCTTGCGC
AGCTGTGCTCGACGTTGTCACTGAAGCGGGAAGGGACTGGCTGCTAT
TGGGCGAAGTGCCGGGGCAGGATCTCCTGTCATCTCACCTTGCTCCTG
CCGAGAAAGTATCCATCATGGCTGATGCAATGCGGCGGCTGCATACG
CTTGATCCGGCTACCTGCCCATTCGACCACCAAGCGAAACATCGCAT
CGAGCGAGCACGTACTCGGATGGAAGCCGGTCTTGTCGATCAGGATG
ATCTGGACGAAGAGCATCAGGGGCTCGCGCCAGCCGAACTGTTCGCC
AGGCTCAAGGCGCGGATGCCCGACGGCGAGGATCTCGTCGTGACCCA
TGGCGATGCCTGCTTGCCGAATATCATGGTGGAAAATGGCCGCTTTTC
TGGATTCATCGACTGTGGCCGGCTGGGTGTGGCGGACCGCTATCAGG
ACATAGCGTTGGCTACCCGTGATATTGCTGAAGAGCTTGGCGGCGAA
TGGGCTGACCGCTTCCTCGTGCTTTACGGTATCGCCGCTCCCGATTCG
CAGCGCATCGCCTTCTATCGCCTTCTTGACGAGTTCTTCTGATGATGA
ATGGCAAGGCGGCGCGTAGCCCCCCAACCGAAGTTGAGGGGATTTTT

```
TGGACTATGAGCACGTCCGCGAGGGCGTCCCGGAAAACGATTCCGAA
GCCCAACCTTTCATAGAAGGCGGCGGTGGAATCGAAATCTCGTGATG
GCAGGTTGGGCGTCGCTTGGTCGGTCATTTCGCTCGGTACCCATCGGC
ATTTTCTTTTGCGTTTTTATTTGTTAACTGTTAATTGTCCTTGTTCAAG
GATGCTGTCTTTGAGAACAGATGTTTTCTTGCCTTTGATGTTCAGCAG
GAAGCTCGGCGCAAACGTTGATTGTTTGTCTGCGTAGAATCCTCTGTT
TGTCATATAGCTTGTAATCACGACATTGTTTCCTTTCGCTTGAGGTAC
AGCGAAGTGTGAGTAAGTAAAGGTTACATCGTTAGGATCAAGATCCA
TTTTTAACACAAGGCCAGTTTTGTTCAGCGGCTTGTATGGGCCAGTTA
AAGAATTAGAAACATAACCAAGCATGTAAATATCGTTAGACGTAATG
CCGTCAATCGTCATTTTTGATCCGCGGGAGTCAGTGAACAGGTACCA
TTTGCCGTTCATTTTAAAGACGTTCGCGCGTTCAATTTCATCTGTTACT
GTGTTAGATGCAATCAGCGGTTTCATCACTTTTTTCAGTGTGTAATCA
TCGTTTAGCTCAATCATACCGAGAGCGCCGTTTGCTAACTCAGCCGTG
CGTTTTTTATCGCTTTGCAGAAGTTTTTGACTTTCTTGACGGAAGAAT
GATGTGCTTTTGCCATAGTATGCTTTGTTAAATAAAGATTCTTCGCCT
TGGTAGCCATCTTCAGTTCCAGTGTTTGCTTCAAATACTAAGTATTTG
TGGCCTTTATCTTCTACGTAGTGAGGATCTCTCAGCGTATGGTTGTCG
CCTGAGCTGTAGTTGCCTTCATCGATGAACTGCTGTACATTTTGATAC
GTTTTTCCGTCACCGTCAAAGATTGATTTATAATCCTCTACACCGTTG
ATGTTCAAAGAGCTGTCTGATGCTGATACGTTAACTTGTGCAGTTGTC
AGTGTTTGTTTGCCGTAATGTTTACCGGAGAAATCAGTGTAGAATAA
ACGGATTTTTCCGTCAGATGTAAATGTGGCTGAACCTGACCATTCTTG
TGTTTGGTCTTTTAGGATAGAATCATTTGCATCGAATTTGTCGCTGTC
TTTAAAGACGCGGCCAGCGTTTTTCCAGCTGTCAATAGAAGTTTCGCC
GACTTTTTGATAGAACATGTAAATCGATGTGTCATCCGCATTTTTAGG
ATCTCCGGCTAATGCAAAGACGATGTGGTAGCCGTGATAGTTTGCGA
CAGTGCCGTCAGCGTTTTGTAATGGCCAGCTGTCCCAAACGTCCAGG
CCTTTTGCAGAAGAGATATTTTTAATTGTGGACGAATCAAATTCAGA
AACTTGATATTTTTCATTTTTTTGCTGTTCAGGGATTTGCAGCATATCA
TGGCGTGTAATATGGGAAATGCCGTATGTTTCCTTATATGGCTTTTGG
TTCGTTTCTTTCGCAAACGCTTGAGTTGCGCCTCCTGCCAGCAGTGCG
GTAGTAAAGGTTAATACTGTTGCTTGTTTTGCAAACTTTTTGATGTTC
ATACTCTTCCTTTTTCAATATTATTGAAGCATTTATCAGGGTTATTGTC
TCATGAGCGGATACATATTTGAATGTATTTAGAAAAATAAACAAATA
GGGGTTCCGCGCACATTTCCCCGAAAAGTGCCACCTGACGTCTAAGA
AACCATTATTATCATGAGATTAACCTATAAAAATAGGCGTATCACGA
GGCCCTTTCGTCTTCAAGAATTCTCATGTTTGAGAGCTTATCATCGAT
AAGCTTTAATGCGGTAGTTTATCACAGTTAAATTGCTAACGCAGTCA
GGCACCGTGTATGTCGCATCTTGCAGAATTAGTAGCTTCAGCGAAGG
CCGCGATTTCTCAGGCGAGTGACGTCGCAGCACTGGATAATGTACGT
GTTGAGTACCTGGGAAAGAAGGGACACCTTACTCTTCAAATGACAAC
CCTGCGCGAACTGCCGCCGGAGGAACGCCCCGCAGCAGGAGCGGTA
ATCAATGAGGCAAAGGAGCAAGTACAACAGGCACTGAACGCCCGTA
AGGCTGAGTTGGAATCCGCCGCATTAAACGCGCGCCTTGCTGCGGAA
ACCATTGATGTCTCGCTGCCCGGGCGCCGCATTGAGAATGGAGGCTT
ACACCCAGTGACTCGTACCATCGACCGTATCGAATCTTTCTTTGGCGA
ACTTGGCTTCACTGTGGCAACTGGACCGGAGATTGAGGACGACTACC
ACAATTTCGATGCCTTGAACATTCCCGGTCATCATCCTGCACGCGCCG
ATCATGATACATTCTGGTTTGATACCACCCGTTTGCTTCGTACCCAGA
CAAGCGGTGTCCAAATCCGTACGATGAAGGCTCAGCAACCACCGATC
CGTATCATTGCTCCAGGGCGCGTGTACCGTAACGATTATGACCAGAC
ACATACACCGATGTTTCACCAAATGGAAGGGTTGATTGTGGATACGA
ATATCTCTTTCACGAATCTGAAGGGCACCTTACATGATTTCTTACGCA
ACTTTTTCGAGGAGGACCTTCAAATTCGCTTTCGTCCATCGTACTTCC
CTTTTGCAGAACCTTCGGCTGAAGTGGATGTAATGGGGAAAAACGGT
AAGTGGCTGGAGGTTTTAGGTTGCGGGATGGTTCATCCAAATGTGCT
TCGCAACGTCGGCATCGACCCCGAAGTCTACAGTGGATTCGGATTCG
GGATGGAATGGAACGTCTGACTATGCTTCGTTACGGCGTAACGGAT
TTGCGCTCCTTTTTTGAGAACGATCTTCGTTTTCTGAAGCAATTCAAA
TAAGCATTTTTAGTACGTGCAATAACCACTCTGGTTTTTCCAGGGTGG
TTTTTTGATGCCCTTTTTGGAGTCTTCAACTGAGCCTCGCCCTAGGAA
CTTAAGAGCCTCGCAGAGCAGGATTCCCGTTGAGCACCGCCAGGTGC
GAATAAGGGACAGTGAAGAAGGAACACCCGCTCGCGGGTGGGCCTA
CTTCACCTATCCTGCCCGGCTGACGCCGTTGGATACACCAAGGAAAG
TCTACACGAACCCTTTGGCAAAATCCTGTATATCGTGCGAAAAAGGA
TGGATATACCGAAAAAATCGCTATAATGACCCCGAAGCAGGGTTATG
CAGCGGAAAAGCGGTCCTTTTCATCACGTGCTATAAAAATAATTATA
ATTTAAATTTTTTAATATAAATATATAAATTAAAAATAGAAAGTAAA
AAAAGAAATTAAAGAAAAAATAGTTTTTGTTTTCCGAAGATGTAAAA
GACTCTAGGGGGATCGCCAACAAATACTACCTTTTATCTTGCTCTTCC
TGCTCTCAGGTATTAATGCCGAATTGTTTCATCTTGTCTGTGTAGAAG
ACCACACACGAAAATCCTGTGATTTTACATTTTACTTATCGTTAATCG
AATGTATATCTATTTAATCTGCTTTTCTTGTCTAATAAATATATATGTA
AAGTACGCTTTTTGTTGAAATTTTTTAAACCTTTGTTTATTTTTTTTTC
TTCATTCCGTAACTCTTCTACCTTCTTTATTTACTTTCTAAAATCCAAA
TACAAAACATAAAAATAAATAAACACAGAGTAAATTCCCAAATTATT
CCATCATTAAAAGATACGAGGCGCGTGTAAGTTACAGGCAAGCGATC
CGCGCGTTTCGGTGATGACGGTGAAAACCTCTGACACATGCAGCTCC
CGGAGACGGTCACAGCTTGTCTGTAAGCGGATGCCGGGAGCAGACA
AGCCCGTCAGGGCGCGTCAGCGGGTGTTGGCGGGTGTCGGGGCTGGC
```

```
TTAACTATGCGGCATCAGAGCAGATTGTACTGAGAGTGCACCATACC
ACAGCCGGAAGAGGAGTAGGGAATATTACTGGCTGAAAATAAGTCTT
GAATGAACGTATACGCGTATATTTCTACCAATCTCTCAACACTGAGTA
ATGGTAGTTATAAGAAAGAGACCGAGTTAGGGACAGTTAGAGGCGG
TGGAGATATTCCTTATGGCATGTCTGGCGATGATAAAACTTTTCAAAC
GGCAGCCCCGATCTAAAAGAGCTGACAGGGAAATGGTCAGAAAAAG
AAACGTGCACCCGCCCGTCTGGACGCGCCGCTCACCCGCACGGCAGA
GACCAATCAGTAAAAATCAACGGTTAACGACATTACTATATATATAA
TATAGGAAGCATTTAATAGAACAGCATCGTAATATATGTGTACTTTG
CAGTTATGACGCCAGATGGCAGTAGTGGAAGATATTCTTTATTGAAA
AATAGCTTGTCACCTTACGTACAATCTTGATCCGGAGCTTTTCTTTTTT
TGCCGATTAAGAATTCGGTCGAAAAAGAAAAGGAGAGGGCCAAGA
GGGAGGGCATTGGTGACTATTGAGCACGTGAGTATACGTGATTAAGC
ACACAAAGGCAGCTTGGAGTATGTCTGTTATTAATTTCACAGGTAGTT
CTGGTCCATTGGTGAAAGTTTGCGGCTTGCAGAGCACAGAGGCCGCA
GAATGTGCTCTAGATTCCGATGCTGACTTGCTGGGTATTATATGTGTG
CCCAATAGAAAGAGAACAATTGACCCGGTTATTGCAAGGAAAATTTC
AAGTCTTGTAAAAGCATATAAAAATAGTTCAGGCACTCCGAAATACT
TGGTTGGCGTGTTTCGTAATCAACCTAAGGAGGATGTTTTGGCTCTGG
TCAATGATTACGGCATTGATATCGTCCAACTGCATGGAGATGAGTCG
TGGCAAGAATACCAAGAGTTCCTCGGTTTGCCAGTTATTAAAAGACT
CGTATTTCCAAAAGACTGCAACATACTACTCAGTGCAGCTTCACAGA
AACCTCATTCGTTTATTCCCTTGTTTGATTCAGAAGCAGGTGGGACAG
GTGAACTTTTGGATTGGAACTCGATTTCTGACTGGGTTGGAAGGCAA
GAGAGCCCCGAAAGCTTACATTTTATGTTAGCTGGTGGACTGACGCC
AGAAAATGTTGGTGATGCGCTTAGATTAAATGGCGTTATTGGTGTTG
ATGTAAGCGGAGGTGTGGAGACAAATGGTGTAAAAGACTCTAACAA
AATAGCAAATTTCGTCAAAAATGCTAAGAAATAGGTTATTACTGAGT
AGTATTTATTTAAGTATTGTTTGTGCACTTGCCTGCAGGCCTTTTGAA
AAGCAAGCATAAAAGATCTAAACATAAAATCTGTAAAATAACAAGA
TGTAAAGATAATGCTAAATCATTTGGCTTTTTGATTGATTGTACAGGC
CCTGGCTTGTTGTCCACAACCGTTAAACCTTAAAAGCTTAAAAGCCT
TATATATTCTTTTTTTTCTTATAAAACTTAAAACCTTAGAGGCTATTTA
AGTTGCTGATTTATATTAATTTTATTGTTCAAACATGAGAGCTTAGTA
CGTGAAACATGAGAGCTTAGTACGTTAGCCATGAGGGTTTAGTTCGT
TAGCCATGAGGGTTTAGTTCGTTAAACATGAGAGCTTAGTACGTTAA
ACATGAGAGCTTAGTACGTGAAACATGAGAGCTTAGTACGTACTATC
AACAGGTTGAACTGCTGATCTTCTATTCACACGCAATCAACAGGCAG
GATAATCGCTGGTAAGGTCAGTGCTTTCTTCAGGTAGTAGAGATACA
```
```
ATAGTTCCCAACGATAGGTGGCAGATTTCACTTTACAGACCGACTGG
TTCAGAAGCGTAGATAATAGCCCGTGTTTTCCAATAAGGGATAGTGT
AGGTAAGTCAACTCCTCCGTCAGAGCCAACCGTTT
```

35. Plasmid AV18_DNA (SEQ ID NO: 35)
```
CTGGGGCGCCCTCTGGTAAGGTTGGGAAGCCCTGCAAAGTAAACTGG
ATGCCAGGCATCAAATAAAACGAAAGGCTCAGTCGAAAGACTGGGC
CTTTCGTTTTATCTGTTGTTTGTCGGTGAACGCTCTCTACTAGAGTCAC
ACTGGCTCACCTTCGGGTGGGCCTTTCTGCGTTTATAGCACTAGGACT
TGCCGCGGATACTGCCCCATTACATGAATTGCAGCCTCAGGGACGTC
AGTAGATCATGGAGGTAGGGCATATGTCCTCTGTTGTTAAAATGTGA
GTTCTCAACGAAGCACGAATCGGTCAGAACCTACACTAAGGAGATTT
GGTAGGTGCACGGTTTCTGTCGCATAGACCAGTTCATTTCAGATGTCT
GGCACGTAAGAGGTTCCAACTTTCACCATAATGAAATAAGATCACTA
CCGGGCGTATTTTTTGAGTTATCGAGATTTTCAGGAGCTAAGGAAGCT
AAAATGATTGAACAAGATGGATTGCACGCAGGTTCTCCGGCCGCTTG
GGTGGAGAGGCTATTCGGCTATGACTGGGCACAACAGACAATCGGCT
GCTCTGATGCCGCCGTGTTCCGGCTGTCAGCGCAGGGGCGCCCGGTT
CTTTTTGTCAAGACCGACCTGTCCGGTGCCCTGAATGAACTCCAAGAC
GAGGCAGCGCGGCTATCGTGGCTGGCCACGACGGGCGTTCCTTGCGC
AGCTGTGCTCGACGTTGTCACTGAAGCGGGAAGGGACTGGCTGCTAT
TGGGCGAAGTGCCGGGGCAGGATCTCCTGTCATCTCACCTTGCTCCTG
CCGAGAAAGTATCCATCATGGCTGATGCAATGCGGCGGCTGCATACG
CTTGATCCGGCTACCTGCCCATTCGACCACCAAGCGAAACATCGCAT
CGAGCGAGCACGTACTCGGATGGAAGCCGGTCTTGTCGATCAGGATG
ATCTGGACGAAGAGCATCAGGGGCTCGCGCCAGCCGAACTGTTCGCC
AGGCTCAAGGCGCGGATGCCCGACGGCGAGGATCTCGTCGTGACCCA
TGGCGATGCCTGCTTGCCGAATATCATGGTGGAAAATGGCCGCTTTTC
TGGATTCATCGACTGTGGCCGGCTGGGTGTGGCGGACCGCTATCAGG
ACATAGCGTTGGCTACCCGTGATATTGCTGAAGAGCTTGGCGGCGAA
TGGGCTGACCGCTTCCTCGTGCTTTACGGTATCGCCGCTCCCGATTCG
CAGCGCATCGCCTTCTATCGCCTTCTTGACGAGTTCTTCTGATGATGA
ATGGCAAGGCGGCGCGTAGCCCCCCAACCGAAGTTGAGGGGATTTTT
TTGACAATTAATCATCCGGCTCGTAATTTATGTGGATCTTAATCATGC
TAAGGAGGTTTTCTAATGATGAAGATCAAAAAGTTTGCAAAACAAGC
AACAGTATTAACCTTTACTACCGCACTGCTGGCAGGAGGCGCAACTC
AAGCGTTTGCGAAAGAAACGAACCAAAAGCCATATAAGGAAACATA
CGGCATTTCCCATATTACACGCCATGATATGCTGCAAATCCCTGAACA
GCAAAAAAATGAAAAATATCAAGTTTCTGAATTTGATTCGTCCACAA
TTAAAAATATCTCTTCTGCAAAAGGCCTGGACGTTTGGGACAGCTGG
CCATTACAAAACGCTGACGGCACTGTCGCAAACTATCACGGCTACCA
```

-continued

```
CATCGTCTTTGCATTAGCCGGAGATCCTAAAAATGCGGATGACACAT
CGATTTACATGTTCTATCAAAAAGTCGGCGAAACTTCTATTGACAGCT
GGAAAAACGCTGGCCGCGTCTTTAAAGACAGCGACAAATTCGATGCA
AATGATTCTATCCTAAAAGACCAAACACAAGAATGGTCAGGTTCAGC
CACATTTACATCTGACGGAAAAATCCGTTTATTCTACACTGATTTCTC
CGGTAAACATTACGGCAAACAAACACTGACAACTGCACAAGTTAACG
TATCAGCATCAGACAGCTCTTTGAACATCAACGGTGTAGAGGATTAT
AAATCAATCTTTGACGGTGACGGAAAAACGTATCAAAATGTACAGCA
GTTCATCGATGAAGGCAACTACAGCTCAGGCGACAACCATACGCTGA
GAGATCCTCACTACGTAGAAGATAAAGGCCACAAATACTTAGTATTT
GAAGCAAACACTGGAACTGAAGATGGCTACCAAGGCGAAGAATCTT
TATTTAACAAAGCATACTATGGCAAAAGCACATCATTCTTCCGTCAA
GAAAGTCAAAAACTTCTGCAAAGCGATAAAAAACGCACGGCTGAGT
TAGCAAACGGCGCTCTCGGTATGATTGAGCTAAACGATGATTACACA
CTGAAAAAAGTGATGAAACCGCTGATTGCATCTAACACAGTAACAGA
TGAAATTGAACGCGCGAACGTCTTTAAAATGAACGGCAAATGGTACC
TGTTCACTGACTCCCGCGGATCAAAAATGACGATTGACGGCATTACG
TCTAACGATATTTACATGCTTGGTTATGTTTCTAATTCTTTAACTGGCC
CATACAAGCCGCTGAACAAAACTGGCCTTGTGTTAAAAATGGATCTT
GATCCTAACGATGTAACCTTTACTTACTCACACTTCGCTGTACCTCAA
GCGAAAGGAAACAATGTCGTGATTACAAGCTATATGACAAACAGAG
GATTCTACGCAGACAAACAATCAACGTTTGCGCCGAGCTTCCTGCTG
AACATCAAAGGCAAGAAAACATCTGTTGTCAAAGACAGCATCCTTGA
ACAAGGACAATTAACAGTTAACAAATAAAAACGCAAAAGAAAATGC
CGATGGGTACCGAGCGAAATGACCGACCAAGCGACGCCCAACCTGC
CATCACGAGATTTCGATTCCACCGCCGCCTTCTATGAAAGGTTGGGCT
TCGGAATCGTTTTCCGGGACGCCCTCGCGGACGTGCTCATAGTCCAG
GCGGTGTTGACATAAATACCACTGGCGGTGATACTGAGCACATCAGC
AGGTCACACAGGAAAGTACTAGATGTCGCATCTTGCAGAATTAGTAG
CTTCAGCGAAGGCCGCGATTTCTCAGGCGAGTGACGTCGCAGCACTG
GATAATGTACGTGTTGAGTACCTGGGAAGAAGGGACACCTTACTCT
TCAAATGACAACCCTGCGCGAACTGCCGCCGGAGGAACGCCCCGCAG
CAGGAGCGGTAATCAATGAGGCAAAGGAGCAAGTACAACAGGCACT
GAACGCCCGTAAGGCTGAGTTGGAATCCGCCGCATTAAACGCGCGCC
TTGCTGCGGAAACCATTGATGTCTCGCTGCCCGGGCGCCGCATTGAG
AATGGAGGCTTACACCCAGTGACTCGTACCATCGACCGTATCGAATC
TTTCTTTGGCGAACTTGGCTTCACTGTGGCAACTGGACCGGAGATTGA
GGACGACTACCACAATTTCGATGCCTTGAACATTCCCGGTCATCATCC
TGCACGCGCCGATCATGATACATTCTGGTTTGATACCACCCGTTTGCT
TCGTACCCAGACAAGCGGTGTCCAAATCCGTACGATGAAGGCTCAGC
AACCACCGATCCGTATCATTGCTCCAGGGCGCGTGTACCGTAACGAT
TATGACCAGACACATACACCGATGTTTCACCAAATGGAAGGGTTGAT
TGTGGATACGAATATCTCTTTCACGAATCTGAAGGGCACCTTACATG
ATTTCTTACGCAACTTTTTCGAGGAGGACCTTCAAATTCGCTTTCGTC
CATCGTACTTCCCTTTTGCAGAACCTTCGGCTGAAGTGGATGTAATGG
GGAAAAACGGTAAGTGGCTGGAGGTTTTAGGTTGCGGGATGGTTCAT
CCAAATGTGCTTCGCAACGTCGGCATCGACCCCGAAGTCTACAGTGG
ATTCGGATTCGGGATGGGAATGGAACGTCTGACTATGCTTCGTTACG
GCGTAACGGATTTGCGCTCCTTTTTTGAGAACGATCTTCGTTTTCTGA
AGCAATTCAAATAAGCATTTTTAGTACGTGCAATAACCACTCTGGTTT
TTCCAGGGTGGTTTTTGATGCCCTTTTTGGAGTCTTCAACTGAGCCT
CGCAGAGCAGGATTCCCGTTGAGCACCGCCAGGTGCGAATAAGGGA
CAGTGAAGAAGGAACACCCGCTCGCGGGTGGGCCTACTTCACCTATC
CTGCCCGGCTGACGCCGTTGGATACACCAAGGAAAGTCTACACGAAC
CCTTTGGCAAAATCCTGTATATCGTGCGAAAAAGGATGGATATACCG
AAAAAATCGCTATAATGACCCCGAAGCAGGGTTATGCAGCGGAAAA
GCTCCCCGAAAAGTGCCACCTGGGTCCTTTTCATCACGTGCTATAAAA
ATAATTATAATTTAAATTTTTTAATATAAATATATAAATTAAAAATAG
AAAGTAAAAAAGAAATTAAAGAAAAAATAGTTTTTGTTTTCCGAAG
ATGTAAAAGACTCTAGGGGGATCGCCAACAAATACTACCTTTTATCT
TGCTCTTCCTGCTCTCAGGTATTAATGCCGAATTGTTTCATCTTGTCTG
TGTAGAAGACCACACACGAAAATCCTGTGATTTTACATTTTACTTATC
GTTAATCGAATGTATATCTATTTAATCTGCTTTTCTTGTCTAATAAATA
TATATGTAAAGTACGCTTTTTGTTGAAATTTTTTAAACCTTTGTTTATT
TTTTTTTTCTTCATTCCGTAACTCTTCTACCTTCTTTATTTACTTTCTAA
AATCCAAATACAAAACATAAAAATAAATAAACACAGAGTAAATTCC
CAAATTATTCCATCATTAAAAGATACGAGGCGCGTGTAAGTTACAGG
CAAGCGATCCGTCTAAGAAACCATTATTATCATGACATTAACCTATA
AAAATAGGCGTATCACGAGGCCCTTTCGTCTCGCGCGTTTCGGTGAT
GACGGTGAAAACCTCTGACACATGCAGCTCCCGGAGACGGTCACAGC
TTGTCTGTAAGCGGATGCCGGGAGCAGACAAGCCCGTCAGGGCGCGT
CAGCGGGTGTTGGCGGGTGTCGGGCTGGCTTAACTATGCGGCATCA
GAGCAGATTGTACTGAGAGTGCACCATACCACAGCCGGAAGAGGAG
TAGGGAATATTACTGGCTGAAAATAAGTCTTGAATGAACGTATACGC
GTATATTTCTACCAATCTCTCAACACTGAGTAATGGTAGTTATAAGAA
AGAGACCGAGTTAGGGACAGTTAGAGGCGGTGGAGATATTCCTTATG
GCATGTCTGGCGATGATAAAACTTTTCAAACGGCAGCCCCGATCTAA
AAGAGCTGACAGGGAAATGGTCAGAAAAAGAAACGTGCACCCGCCC
GTCTGGACGCGCCGCTCACCCGCACGGCAGAGACCAATCAGTAAAAA
TCAACGGTTAACGACATTACTATATATATAATATAGGAAGCATTTAA
TAGAACAGCATCGTAATATATGTGTACTTTGCAGTTATGACGCCAGA
```

-continued
TGGCAGTAGTGGAAGATATTCTTTATTGAAAAATAGCTTGTCACCTTA
CGTACAATCTTGATCCGGAGCTTTTCTTTTTTTGCCGATTAAGAATTC
GGTCGAAAAAGAAAAGGAGAGGGCCAAGAGGGAGGGCATTGGTG
ACTATTGAGCACGTGAGTATACGTGATTAAGCACACAAAGGCAGCTT
GGAGTATGTCTGTTATTAATTTCACAGGTAGTTCTGGTCCATTGGTGA
AAGTTTGCGGCTTGCAGAGCACAGAGGCCGCAGAATGTGCTCTAGAT
TCCGATGCTGACTTGCTGGGTATTATATGTGTGCCCAATAGAAAGAG
AACAATTGACCCGGTTATTGCAAGGAAAATTTCAAGTCTTGTAAAAG
CATATAAAAATAGTTCAGGCACTCCGAAATACTTGGTTGGCGTGTTTC
GTAATCAACCTAAGGAGGATGTTTTGGCTCTGGTCAATGATTACGGC
ATTGATATCGTCCAACTGCATGGAGATGAGTCGTGGCAAGAATACCA
AGAGTTCCTCGGTTTGCCAGTTATTAAAAGACTCGTATTTCCAAAGA
CTGCAACATACTACTCAGTGCAGCTTCACAGAAACCTCATTCGTTTAT
TCCCTTGTTTGATTCAGAAGCAGGTGGGACAGGTGAACTTTTGGATTG
GAACTCGATTTCTGACTGGGTTGGAAGGCAAGAGAGCCCCGAAAGCT
TACATTTTATGTTAGCTGGTGGACTGACGCCAGAAAATGTTGGTGAT
GCGCTTAGATTAAATGGCGTTATTGGTGTTGATGTAAGCGGAGGTGT
GGAGACAAATGGTGTAAAAGACTCTAACAAAATAGCAAATTTCGTCA
AAAATGCTAAGAAATAGGTTATTACTGAGTAGTATTTATTTAAGTATT
GTTTGTGCACTTGCCTGCAGGCCTTTTGAAAAGCAAGCATAAAAGAT
CTAAACATAAAATCTGTAAAATAACAAGATGTAAAGATAATGCTAAA
TCATTTGGCTTTTTGATTGATTGTACAGGCCCTGGCTTGTTGTCCACA
ACCGTTAAACCTTAAAAGCTTTAAAAGCCTTATATATTCTTTTTTTCT
TATAAAACTTAAAACCTTAGAGGCTATTTAAGTTGCTGATTTATATTA
ATTTTATTGTTCAAACATGAGAGCTTAGTACGTGAAACATGAGAGCT
TAGTACGTTAGCCATGAGGGTTTAGTTCGTTAGCCATGAGGGTTTAGT
TCGTTAAACATGAGAGCTTAGTACGTTAAACATGAGAGCTTAGTACG
TGAAACATGAGAGCTTAGTACGTACTATCAACAGGTTGAACTGCTGA
TCTTCGGCATCAAATAAAACGAAAGGCTCAGTCGAAAGACTGGGCCT
TTCGTTTTATCTGTTGTTTGTCGGTGAACGCTCTCCTGAGTAGGACAA
ATCCGCCGCCCTAGATATTCACACGCAATCAACAGGCAGGATAATCG
CTGGTAAGGTCAGTGCTTTCTTCAGGTAGTAGAGATACAATAGTTCCC
AACGATAGGTGGCAGATTTCACTTTACAGACCGACTGGTTCAGAAGC
GTAGATAATAGCCCGTGTTTTCCAATAAGGGATAGTGTAGGTAAGTC
AACTCCTCCGTCAGAGCCAACCGTTT 36. rhtC upstream homology arm-PxapR-rhtC-
downstream homology arm_DNA
(SEQ ID NO: 36)
ATTCCAGCGCGATGACCTGCAAATTGTGGTGGCGACGGTGGCGTTCG
GCATGGGCATCAATAAACCAAACGTTCGCTTCGTGGTCCACTTTGAT
ATTCCGCGCAATATCGAATCCTATTATCAGGAAACCGGACGCGCCGG
GCGTGATGGCCTGCCCGCGGAAGCGATGCTGTTTTACGATCCGGCTG ATATGGCGTGGCTGCGCCGTTGTCTGGAAGAGAAGCCGCAGGGGCAG
TTGCAGGATATCGAGCGCCACAAACTCAATGCGATGGGCGCGTTTGC
CGAAGCGCAAACTTGCCGTCGTCTGGTATTGCTGAACTATTTTGGCGA
AGGGCGTCAGGAGCCGTGCGGGAACTGCGATATCTGCCTCGATCCGC
CGAAACAGTACGACGGTTCAACCGATGCTCAGATTGCCCTTTCCACC
ATTGGTCGTGTGAATCAGCGGTTTGGGATGGGTTATGTGGTGGAAGT
GATTCGTGGTGCTAATAACCAGCGTATCCGCGACTATGGTCATGACA
AACTGAAAGTCTATGGCATGGGCCGTGATAAAAGCCATGAACATTGG
GTGAGCGTGATCCGCCAGCTGATTCACCTCGGCCTGGTGACGCAAAA
TATTGCCCAGCATTCTGCCCTACAACTGACAGAGGCCGCGCGCCCGG
TGCTGCGCGGCGAATCCTCTTTGCAACTTGCCGTGCCGCGTATCGTGG
CGCTCAAACCGAAAGCGATGCAGAAATCGTTCGGCGGCAACTATGAT
CGCAAACTGTTCGCCAAATTACGCAAACTGCGTAAATCGATAGCCGA
TGAAAGTAATGTCCCGCCGTACGTGGTGTTTAACGACGCAACCTTGA
TTGAGATGGCTGAACAGATGCCGATCACCGCCAGCGAAATGCTCAGC
GTTAACGGCGTTGGGATGCGCAAGCTGGAACGCTTTGGCAAACCGTT
TATGGCGCTGATTCGTGCGCATGTTGATGGCGATGACGAAGAGTAGT
CAGCAGCATAAAAAAGTGCCAGTATGAAGACTCCGTAAACGTTTCCC
CCGCGAGTCAAATGTATGTCGGATATCTGGTGGTGAAATACTTTATG
CCATGATAATTTAATACGATGTATTTATTATATGGAGCACTTAATTAT
GTTGATGTTATTTCTCACCGTCGCCATGGTGCACATTGTGGCGCTTAT
GAGCCCCGGTCCCGATTTCTTTTTTGTCTCTCAGACCGCTGTCAGTCG
TTCCCGTAAAGAAGCGATGATGGGCGTGCTGGGCATTACCTGCGGCG
TAATGTTTGGGCTGGGATTGCGCTGCTTGGCCTGCATTTGATTATCG
AAAAAATGGCCTGGCTGCATACGCTGATTATGGTGGGCGGTGGCCTG
TATCTCTGCTGGATGGGTTACCAGATGCTACGTGGTGCACTGAAAAA
AGAGGCGGTTTCTGCACCTGCGCCACAGGTCGAGCTGGCGAAAAGTG
GGCGCAGTTTCCTGAAAGGTTTACTGACCAATCTCGCTAATCCGAAA
GCGATTATCTACTTTGGCTCGGTGTTCTCATTGTTTGTCGGTGATAAC
GTTGGCACTACCGCGCGCTGGGGCATTTTTGCGCTGATCATTGTCGAA
ACGCTGGCGTGGTTTACCGTCGTTGCCAGCCTGTTTGCCCTGCCGCAA
ATGCGCCGTGGTTATCAACGTCTGGCGAAGTGGATTGATGGTTTTGCC
GGGGCGTTATTTGCCGGATTTGGCATTCATTTGATTATTTCGCGGTGA
TGCCAGACGCGTCTTCAGAGTAAGTCGGATAAGGCGTTTACGCCGCA
TCCGACATTATTTTTCACGCATGCCTCGCCGATGCTAACAGCGCTCCC
ACCAGCATAAACAACGAGCCGAAAATCTTATTCAGCGCCTTCATCTG
CTTTGGTCCTTTAATCCATAGAGCAATCCGTTGAGCAAGGGTGGCGT
AACCGATCATCACAATAATATCGACCACAATAGTGGTGACGCCGAGC
ACGATATACTGCATCAGTTGCGGCTGTTGCGGCATGATGAATTGCGG

```
AAATAGCGCCGCCAGAAACACAATACTTTTGGGATTGGTGAGATTCA

CAAAAACTGCGCGCTGGAACAAATGTCGACGCGATTGAGTAGAGGC

CAGCGATTTAAGGTCAATTGCACCAGCGGCG

37. PxapR promoter_E. coli_DNA
                                        (SEQ ID NO: 37)
ATGTCGGATATCTGGTGGTGAAATACTTTATGCCATGATAATTTAATA

CGATGTATTTATTATATGGAGCACTTAATT

38. PxapR-rhtC_DNA
                                        (SEQ ID NO: 38)
ATGTCGGATATCTGGTGGTGAAATACTTTATGCCATGATAATTTAATA

CGATGTATTTATTATATGGAGCACTTAATTATGTTGATGTTATTTCTC

ACCGTCGCCATGGTGCACATTGTGGCGCTTATGAGCCCCGGTCCCGA

TTTCTTTTTTGTCTCTCAGACCGCTGTCAGTCGTTCCCGTAAAGAAGC

GATGATGGGCGTGCTGGGCATTACCTGCGGCGTAATGGTTTGGGCTG

GGATTGCGCTGCTTGGCCTGCATTTGATTATCGAAAAAATGGCCTGG

CTGCATACGCTGATTATGGTGGGCGGTGGCCTGTATCTCTGCTGGATG

GGTTACCAGATGCTACGTGGTGCACTGAAAAAAGAGGCGGTTTCTGC

ACCTGCGCCACAGGTCGAGCTGGCGAAAAGTGGGCGCAGTTTCCTGA

AAGGTTTACTGACCAATCTCGCTAATCCGAAAGCGATTATCTACTTTG

GCTCGGTGTTCTCATTGTTTGTCGGTGATAACGTTGGCACTACCGCGC

GCTGGGGCATTTTTGCGCTGATCATTGTCGAAACGCTGGCGTGGTTTA

CCGTCGTTGCCAGCCTGTTTGCCCTGCCGCAAATGCGCCGTGGTTATC

AACGTCGGCGAAGTGGATTGATGGTTTTGCCGGGGCGTTATTTGCC

GGATTTGGCATTCATTTGATTATTTCGCGGTGA
```

---

The invention claimed is:

1. An *Escherichia coli* (*E coli*) strain useful for the production of threonine by fermentation comprising attenuated expression of a yafV gene relative to a parent strain.

2. The *E. coli* strain of claim 1 further comprising an exogenous pyruvate carboxylase gene operably linked to a promoter to express pyruvate carboxylase in the strain.

3. The *E. coli* strain of claim 2 wherein the exogenous pyruvate carboxylase gene is from *Corynebacterium glutamicum* that encodes the amino acid sequence according to SEQ ID NO:2.

4. The *E. coli* strain of claim 1 further engineered to overexpress a threonine exporter gene in a cell relative to a threonine exporter gene.

5. The *E. coli* strain of claim 4 wherein in the overexpressed threonine exporter gene comprises a non-native promoter operably linked to the gene.

6. The *E. coli* strain of claim 4 wherein the threonine exporter gene is an endogenous rhtC gene encoding a protein according to SEQ ID NO:25.

7. The *E. coli* strain of claim 6 wherein the endogenous rhtC gene comprises a non-native ribosome binding site that causes the overexpression of the gene.

8. The *E. coli* strain of claim 7 wherein the non-native ribosome binding site is according to SEQ ID NO:23.

9. The *E. coli* strain of claim 1 wherein the strains are further engineered to have attenuated expression of an ilvA gene.

10. The *E. coli* strain of claim 9 wherein the ilvA gene has a non-native ribosome binding site inserted upstream of an open reading frame of the gene.

11. The *E. coli* strain of claim 10 wherein the non-native ribosome binding site is according to SEQ ID NO:32.

12. The *E. coli* strain of claim 9 wherein the ilvA gene comprises a transcriptional terminator sequence inserted upstream of a translational start site of the gene.

13. The *E. coli* strain of claim 12 wherein the transcriptional terminator is according to SEQ ID NO:12.

14. The *E. coli* strain of claim 9 wherein the ilvA gene includes a transcriptional terminator sequence inserted upstream of the translational start site of the gene and a non-native ribosome binding site inserted upstream of the open reading frame of the gene.

15. The *E. coli* strain of claim 1 wherein the yafV gene has a non-native ribosome binding site inserted upstream of the open reading frame of the gene.

16. The *E. coli* strain of claim 15 wherein the non-native ribosome binding site is according to SEQ ID NO:13.

17. The *E. coli* strain of claim 1 wherein the yafV gene includes a transcriptional terminator sequence inserted upstream of the translational start site of the gene.

18. The *E. coli* strain of claim 17 wherein the transcriptional terminator is according to SEQ ID NO: 12.

19. The *E. coli* strain of claim 1 wherein the yafV gene includes a transcriptional terminator sequence inserted upstream of the translational start site of the gene and a non-native ribosome binding site inserted upstream of the open reading frame of the gene.

20. The *E. coli* strain of claim 9 wherein each of ilvA gene and the yafV gene has a non-native ribosome binding site inserted upstream of the open reading frame of the gene.

21. The *E. coli* strain of claim 9 wherein each of the ilvA gene and the yafV genes have a transcriptional terminator sequence inserted upstream of the translational start site of the gene.

22. The *E. coli* strain of claim 9 wherein where each of the ilvA gene and the yafV genes have a transcriptional terminator sequence inserted upstream of the translational start site of the gene and a non-native ribosome binding site inserted upstream of the open reading frame of the gene.

23. The *E. coli* strain of claim 9 wherein the strain further includes (a) an exogenous pyruvate carboxylase gene operably linked to a promoter to be expressed pyruvate carboxylase in the strain and; (b) a rhtC threonine exporter gene engineered to be overexpressed in the strain.

24. The *E. coli* strain of claim 23 wherein the rhtC threonine exporter gene is engineered to contain a non-native ribosome binding site that causes the overexpression in the strain.

25. The *E. coli* strain of claim 23 wherein the non-native ribosome binding site is according to SEQ ID NO:13.

* * * * *